(12) United States Patent
Matsuoka et al.

(10) Patent No.: US 6,720,433 B2
(45) Date of Patent: Apr. 13, 2004

(54) ETHYLAMINE DERIVATIVES

(75) Inventors: Hiroharu Matsuoka, Shizuoka (JP); Tsutomu Sato, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/356,558

(22) Filed: Feb. 3, 2003

(65) Prior Publication Data

US 2003/0176643 A1 Sep. 18, 2003

Related U.S. Application Data

(62) Division of application No. 09/787,674, filed as application No. PCT/JP99/05215 on Sep. 24, 1999, now Pat. No. 6,586,630.

(30) Foreign Application Priority Data

Sep. 24, 1998 (JP) ............................................ 10-307784

(51) Int. Cl.$^7$ ...................... C07D 307/38; A61K 31/38
(52) U.S. Cl. ...................... 549/479; 514/357; 514/415; 514/445; 546/336; 548/491
(58) Field of Search .................... 548/491; 549/479; 514/415, 445, 357; 546/336

(56) References Cited

FOREIGN PATENT DOCUMENTS

| EP | 0 647 656 A1 | 8/1994 |
|---|---|---|
| JP | 07138284 | 5/1995 |
| JP | 10-182479 | 7/1998 |
| JP | 10-182479 A | 7/1998 |
| WO | WO 94/03483 A1 | 2/1994 |
| WO | WO 94/11018 A1 | 5/1994 |
| WO | WO 9411018 | 5/1994 |
| WO | WO 96/40208 A1 | 12/1996 |
| WO | WO 0097889 | 1/1997 |
| WO | WO 97/00889 A1 | 1/1997 |
| WO | WO 97/48713 A1 | 12/1997 |
| WO | WO 0999053 | 2/1999 |
| WO | WO 99/21846 A1 | 5/1999 |

OTHER PUBLICATIONS

Kevin T. Chapman, et al. "Inhibition of matrix metalloproteinase by N–carboxyalkyl peptides" J. Med. Chem (1993), vol. 36, No. 26, pp. 4293–4301.

Daniela Pinzani, et al. "Glycosyl derivatives of NK2 tachykinin receptor antagonists", Bioorganic & Medicinal Chemistry Letters (1996), Vol 6, No. 4, pp. 367–372.

Colette T., et al. "Selective ligands for the $\mu$, $\delta$ and k opioid receptors identified from a single mixture based tetrapeptide positional scanning combinatorial library" The Journal of Biological Chemistry (Jul., 1998), vol. 273, No. 30, pp. 18848–18856.

Inge Depoortere et al. "Antagonistic properties of [Phe$^3$, Leu$^{13}$] porcine motilin", European Journal of Pharmacology 286 (1995) 241–247.

Hisanori Takanashi et al. "GMMM–109: A Novel, Selective Motilin Receptor Antagonist in the Smooth Muscle of the Rabbit Small Intestine", The Journal of Pharmacology And Experimental Therapeutics, vol 273, No. 2 pp. 624–628, 1995.

P. Poitras et al. "Motilin Synthetic Analogues And Motilin Receptor Antagonists", Biochemical and Biophysical Research Communications, vol. 205, No. 1, 1994 pp. 449–454.

Colette et al, J. Biol. Chem., vol. 178, n.30, pp. 18848–18856., 1998.

Pinzani et al, Chemistry Letters, vol. 6, n. 4, pp. 367–372, 1996.

Chapman et al, J. Med. Chem. vol. 36, n. 26, 1993.

*Primary Examiner*—Shailendra Kumar
(74) *Attorney, Agent, or Firm*—Browdy and Neimark, P.L.L.C.

(57) ABSTRACT

Ethylamine derivatives that function as a motilin receptor antagonist and are useful as medicines are represented by the general formula (1):

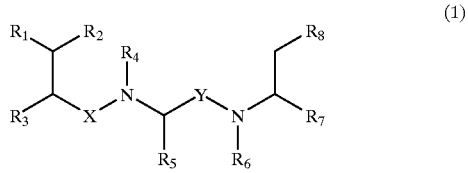

wherein $R_1$ represents a phenyl group or the like, $R_2$ represents a hydrogen atom and the like, $R_3$ represents a hydrogen atom and the like, $R_4$ represents a hydrogen atom and the like, $R_5$ represents an alkyl group and the like, $R_7$ represents a hydrogen atom and the like and $R_8$ represents a heterocyclic ring and the like; or a hydrate or pharmaceutically acceptable salt thereof.

15 Claims, No Drawings

ETHYLAMINE DERIVATIVES

RELATED APPLICATIONS

This is a division of parent application Ser. No. 09/787,674, nationalized Mar. 21, 2001 now U.S. Pat. No. 6,586,630, of which the international application PCT/JP99/05215 was filed on Sep. 24, 1999, which designated the United States, and which application was not published in the English language.

TECHNICAL FIELD

This invention relates to ethylamine derivatives that function as a motilin receptor antagonist and that are useful as medicines.

BACKGROUND ART

Motilin, which is one of the gastrointestinal hormones, is a straight-chained peptide consisting of 22 amino acids and is well known to be responsible for regulating the motility of the gastrointestinal tract in animals including human. It has been reported that exogenously administered motilin causes contractions in humans and dogs that are similar to interdigestive migrating contractions, thus promoting gastric emptying (Itoh et al., Scand. J. Gastroenterol., 11, 93–110 (1976); Peeters et al., Gastroenterology 102, 97–101 (1992)). Hence, erythromycin derivatives which are an agonist of motilin are under development as an gastrointestinal tract motor activity enhancer (Satoh et al., J. Pharmacol. Exp. Therap., 271, 574–579 (1994); Lartey et al., J. Med. Chem., 38, 1793–1798 (1995); Drug of the Future, 19, 910–912 (1994)).

Peptide and polypeptide derivatives have been reported as antagonists of motilin receptors (Depoortere et al., Eur. J. Pharmacol., 286, 241–247 (1995); Poitras et al., Biochem. Biophys. Res. Commun., 205, 449–454 (1994); Takanashi et al., J. Pharmacol. Exp. Ther., 273, 624–628 (1995)). These derivatives are used as a pharmacological tool in the study of the action of motilin on the motility of the gastrointestinal tract and in the research and development of medicines in the field of the art contemplated by the invention.

Motilin receptors had been known to occur principally in the duodenum but recently it has been shown that they also occur in the large intestine, or the lower part of the gastrointestinal tract (William et al., Am. J. Physiol., 262, G50–G55 (1992)), and this indicates the possibility that motilin is involved not only in the motility of the upper part of the gastrointestinal tract but also in the motility of its lower part.

Reports have also been made of the cases of hypermotilinemia in patients with irritable bowel syndrome who were manifesting diarrhea and in patients with irritable bowel syndrome who were under stress (Preston et al., Gut, 26, 1059–1064 (1985); Fukudo et al., Tohoku J. Exp. Med., 151, 373–385 (1987)) and this suggests the possibility that increased blood motilin levels are involved in the disease. Other diseases that have been reported to involve hypermotilinemia include crohn's disease, ulcerative colitis, pancreatitis, diabetes mellitus, obesity, malabsorption syndrome, bacterial diarrhea, atrophic gastritis and postgastroenterectomy syndrome. The antagonists of motilin receptors have the potential to ameliorate irritable bowel syndrome and other diseased states accompanied by increased blood motilin levels.

DISCLOSURE OF INVENTION

An object of the present invention is to provide ethylamine derivatives that function as an antagonist of motilin receptors and which are useful as medicines.

The present inventors conducted repeated intensive studies in an attempt to develop compounds having an outstanding motilin receptor antagonistic action. As a result, they found that ethylamine derivatives represented by the general formula (1) were an excellent antagonist of motilin receptors. The present invention has been accomplished on the basis of this finding.

Thus, the present invention provides compounds represented by the general formula (1):

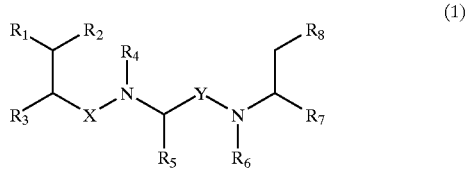

wherein $R_1$ is an optionally substituted phenyl group, an optionally substituted heterocyclic ring, a straight-chained or branched alkenyl group having 2–6 carbon atoms or a straight-chained or branched alkynyl group having 2–6 carbon atoms;

$R_2$ is a hydrogen atom, an optionally substituted straight-chained or branched alkyl group having 1–3 carbon atoms, an amino group or a hydroxy group;

$R_3$ is a hydrogen atom, an optionally substituted straight-chained or branched alkyl group having 1–3 carbon atoms, an optionally substituted amino group or a hydroxy group;

$R_4$ is a hydrogen atom, a methyl group or an ethyl group;

$R_5$ is an optionally substituted straight-chained or branched alkyl group having 1–6 carbon atoms, a cycloalkyl group having 3–7 carbon atoms or an optionally substituted phenyl group;

$R_6$ is a hydrogen atom, a methyl group or an ethyl group;

$R_7$ is a hydrogen atom, an optionally substituted straight-chained or branched alkyl group having 1–3 carbon atoms or —CO—N($R_9$)$R_{10}$;

$R_8$ is an optionally substituted heterocyclic ring having 3–9 carbon atoms or the general formula (2)

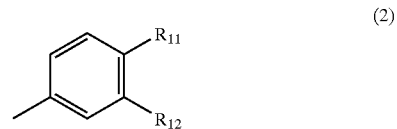

$R_9$ and $R_{10}$, which may be the same or different, each represent a hydrogen atom or an optionally substituted straight-chained or branched alkyl group having 1–3 carbon atoms;

$R_{11}$ is a hydroxy group or a halogen atom;

$R_{12}$, in the case where $R_{11}$ is a hydroxy group, represents a substituted straight-chained or branched alkyl group having 1–6 carbon atoms, a substituted straight-chained or branched alkenyl group having 2–6 carbon atoms, a substituted straight-chained or branched alkynyl group having 2–6 carbon atoms, a straight-chained or branched acyl group having 2–6 carbon atoms, a straight-chained or branched alkylsulfonyl group having 1–5 carbon atoms or an amino group mono- or di-substituted with straight-chained or branched alkyl groups having 1–5 carbon atoms, and $R_{12}$, when $R_{11}$ is a halogen atom, represents an optionally substituted straight-chained or branched alkyl group having 1–6 carbon atoms, an optionally substituted straight-chained or branched alkenyl group having 2–6 carbon atoms, an optionally substituted straight-chained or branched alkynyl group having 2–6 carbon atoms, a straight-chained or branched acyl group having 2–6 carbon atoms, a straight-chained or branched alkylsulfonyl group having 1–5 carbon atoms or an amino group mono- or di-substituted with straight-chained or branched alkyl groups having 1–5 carbon atoms;

X is a carbonyl group or a methylene group; and
Y is a carbonyl group or a methylene group;
or hydrates or pharmaceutically acceptable salts thereof.

The present invention also provides a medicine containing a compound of the general formula (1) as an active ingredient. Further, the present invention provides a motilin receptor antagonist composition containing the compound. The present invention also provides a gastrointestinal motility suppressor agent containing the compound as an active ingredient. Further, the present invention provides a therapeutic of hypermotilinemia containing the compound as an active ingredient.

In the definition of the compounds represented by the general formula (1), exemplary substituents for the optionally substituted phenyl group as $R_1$ include a halogen atom, a hydroxy group, an amino group, a carboxyl group and a methyl group, with a halogen atom and a hydroxy group, particularly a fluorine atom, being preferred.

The optionally substituted phenyl group as $R_1$ is exemplified by a phenyl group optionally substituted with one or more of the above substituents, which may be the same or different; examples include a phenyl group, a para-fluorophenyl group and a para-hydroxyphenyl group, with a phenyl group and a para-fluorophenyl group being particularly preferred.

The heterocyclic ring of the optionally substituted heterocyclic ring as $R_1$ is exemplified by aliphatic or aromatic 5- to 10-membered monocyclic or fused rings containing at least one hetero atom selected from among O, N and S; specific examples include 2-pyridyl, 3-pyridyl, 4-pyridyl, 2-thiazolyl, 2-oxazolyl and 3-indolyl groups.

Exemplary substituents for the optionally substituted heterocyclic ring as $R_1$ include a halogen atom, a hydroxy group, an amino group, a carboxyl group and a straight-chained or branched alkyl group having 1–3 carbon atoms.

Examples of the optionally substituted heterocyclic ring as $R_1$ are 2-pyridyl, 3-pyridyl, 4-pyridyl, 2-thiazolyl, 2-oxazolyl and 3-indolyl groups and the like.

Preferred examples of the straight-chained or branched alkenyl group having 2–6 carbon atoms as $R_1$ are straight-chained or branched alkenyl groups having 4–6 carbon atoms.

Preferred examples of the straight-chained or branched alkynyl group having 2–6 carbon atoms as $R_1$ are straight-chained or branched alkynyl groups having 3–6 carbon atoms.

While $R_1$ has the definitions set forth above, $R_1$ is preferably a phenyl group, a para-fluorophenyl group, a para-hydroxyphenyl group, a 2-pyridyl group, a 2-thiazolyl group or a 3-indolyl group.

In its definition of $R_2$, the alkyl group of the optionally substituted straight-chained or branched alkyl group having 1–3 carbon atoms is preferably a methyl group.

Exemplary substituents for the optionally substituted straight-chained or branched alkyl group having 1–3 carbon atoms as $R_2$ include a halogen atom with a fluorine atom being preferred. The alkyl group may optionally have one or more of these substituents, which may be the same or different.

The optionally substituted straight-chained or branched alkyl group having 1–3 carbon atoms as $R_2$ is preferably a methyl group, an ethyl group, a fluoromethyl group or a trifluoromethyl group, with a methyl group being particularly preferred.

While $R_2$ has the definitions set forth above, $R_2$ is preferably a hydrogen atom or a methyl group.

In its definition of $R_3$, the optionally substituted straight-chained or branched alkyl group having 1–3 carbon atoms is preferably a methyl group.

Exemplary substituents for the optionally substituted straight-chained or branched alkyl group having 1–3 carbon atoms as $R_3$ include a halogen atom with a fluorine atom being preferred. The alkyl group may optionally have one or more of these substituents, which may be the same or different.

The optionally substituted straight-chained or branched alkyl group having 1–3 carbon atoms as $R_3$ is preferably a methyl group or a trifluoromethyl group, with a methyl group being particularly preferred.

Exemplary substituents for the optionally substituted amino group as $R_3$ include a straight-chained or branched alkyl group having 1–3 carbon atoms, with a methyl group being preferred. The amino group may optionally have one or more of these substituents, which may be the same or different.

The optionally substituted amino group as $R_3$ is preferably an amino group, a methylamino group, a dimethylamino group or an ethylamino group, and among them, an amino group and a methylamino group are preferred, with an amino group being particularly preferred.

While $R_3$ has the definitions set forth above, $R_3$ is preferably a hydrogen atom or an amino group.

$R_4$ is preferably a hydrogen atom or a methyl group.

In its definition of $R_5$, the alkyl group of the optionally substituted straight-chained or branched alkyl group having 1–6 carbon atoms is preferably a methyl group, an ethyl group, an isopropyl group, an isobutyl group, a sec-butyl group, a tert-butyl group, a 3-pentyl group or a neopentyl group.

Exemplary substituents for the optionally substituted straight-chained or branched alkyl group having 1–6 carbon atoms as $R_5$ include a phenyl group, a toly group, a para-hydroxyphenyl group, a para-fluorophenyl group, a cycloalkyl group having 3–7 carbon atoms and a halogen atom, with a phenyl group, a cyclohexyl group and a fluorine atom being preferred.

The optionally substituted straight-chained or branched alkyl group having 1–6 carbon atoms as $R_5$ is preferably a methyl group, an isopropyl group, an isobutyl group, a sec-butyl group, a tert-butyl group, a 3-pentyl group, a neopentyl group, a 1,1,1,3,3,3-hexafluoro-2-propyl group, a benzyl group, a para-hydroxybenzyl group or a cyclohexylmethyl group.

The cycloalkyl group having 3–7 carbon atoms as $R_5$ is preferably a cyclopentyl group or a cyclohexyl group.

Exemplary substituents for the optionally substituted phenyl group as $R_5$ include a hydroxy group, an amino group, a methyl group, an ethyl group and a halogen atom.

The optionally substituted phenyl group as $R_5$ is preferably a phenyl group.

While $R_5$ has the definitions set forth above, $R_5$ is preferably a methyl group, an isopropyl group, an isobutyl group, a sec-butyl group, a tert-butyl group, a 3-pentyl group, a neopentyl group, a 1,1,1,3,3,3-hexafluoro-2-propyl group, a cyclohexyl group, a phenyl group, a benzyl group, a para-hydroxybenzyl group or a cyclohexylmethyl group.

$R_6$ is preferably a hydrogen atom or a methyl group.

In its definition of $R_7$, the alkyl group of the optionally substituted straight-chained or branched alkyl group having 1–3 carbon atoms is preferably a methyl group.

Exemplary substituents for the optionally substituted straight-chained or branched alkyl group having 1–3 carbon atoms as $R_7$ include an amino group, a methylamino group, a dimethylamino group, a hydroxy group, methoxy group and a halogen atom, with an amino group being preferred. The alkyl group may optionally have one or more of these substituents, which may be the same or different.

The optionally substituted straight-chained or branched alkyl group having 1–3 carbon atoms as $R_7$ is preferably a methyl group or an aminomethyl group, with a methyl group being particularly preferred.

In its definition of $R_9$ and $R_{10}$ in —CO—N($R_9$)$R_{10}$ as $R_7$, the optionally substituted straight-chained or branched alkyl group having 1–3 carbon atoms is preferably a methyl group or an ethyl group, with a methyl group being more preferred.

While $R_7$ has the definitions set forth above, $R_7$ is preferably a methyl group, a carbamoyl group, a methylcarbamoyl group or a dimethylcarbamoyl group.

The heterocyclic ring of the optionally substituted heterocyclic ring having 3–9 carbon atoms as $R_8$ is exemplified by aliphatic or aromatic 5- to 10-membered monocyclic or fused rings containing at least one hetero atom selected from among O, N and S; specific examples include indole, indoline, indolinone, benzofuran, 2,3-dihydrobenzofuran, furan, thiophene, pyrrole, oxazoline, thiazoline, imidazole, pyridine and pyrimidine, with indole, indoline, indolinone, furan and pyridine being preferred.

Exemplary substituents for the optionally substituted heterocyclic ring having 3–9 carbon atoms as $R_8$ include: a straight-chained or branched alkyl group having 1–4 carbon atoms which may be substituted with a halogen atom, a hydroxy group, etc., as exemplified by a methyl group, an ethyl group, an isopropyl group, a tert-butyl group, a trifluoromethyl group and a hydroxymethyl group; a carboxyl group; a carbamoyl group; a sulfamoyl group; and a hydroxy group. Among them, a methyl group and a tert-butyl group are preferred. The heterocyclic ring may optionally have one or more of these substituents, which may be the same or different.

The optionally substituted heterocyclic ring having 3–9 carbon atoms as RB is preferably a 3-methylindol-5-yl group, a 3,3-dimethylindolin-5-yl group, a 3,3-dimethylindolinon-5-yl group, a 5-tert-butyl-4-carbamoylfuran-2-yl group, a 5-tert-butyl-4-sulfamoylfuran-2-yl group, a 5-tert-butyl-4-hydroxymethylfuran-2-yl group, a 2-tert-butyl-pyridin-4-yl group or a 5-tert-butyl-4-carboxyfuran-2-yl group.

In its definition of $R_{11}$ in general formula (2) as $R_8$, a hydroxy group and a fluorine atom are preferable.

When $R_{11}$ in general formula (2) as $R_8$ is a hydroxy group, the alkyl group of the substituted straight-chained or branched alkyl group having 1–6 carbon atoms as $R_{12}$ in general formula (2) is preferably a straight-chained or branched alkyl group having 1–4 carbon atoms; specific examples include an isopropyl group and a tert-butyl group.

When $R_{11}$ in general formula (2) as $R_8$ is a hydroxy group, the alkenyl group of the substituted straight-chained or branched alkenyl group having 2–6 carbon atoms as $R_{12}$ in general formula (2) is preferably a branched alkenyl group having 3–5 carbon atoms.

When $R_{11}$ in general formula (2) as $R_8$ is a hydroxy group, the alkynyl group of the substituted straight-chained or branched alkynyl group having 2–6 carbon atoms as $R_{12}$ in general formula (2) is preferably a straight-chained or branched alkynyl group having 3–5 carbon atoms.

When $R_{11}$ in general formula (2) as $R_8$ is a hydroxy group, the substituents for the substituted straight-chained or branched alkyl group having 1–6 carbon atoms, the substituted straight-chained or branched alkenyl group having 2–6 carbon atoms and the substituted straight-chained or branched alkynyl group having 2–6 carbon atoms as $R_{12}$ in general formula (2) are preferably a halogen atom, with a fluorine atom being particularly preferred. The alkyl, alkenyl and alkynyl groups may optionally have one or more of these substituents, which may be the same or different.

When $R_{11}$ in general formula (2) as $R_8$ is a hydroxy group, the substituted straight-chained or branched alkyl group having 1–6 carbon atoms as $R_{12}$ in general formula (2) is preferably a perfluoroisopropyl group, a 1,3-difluoro-2-propyl group or a perfluoro-tert-butyl group, with the perfluoroisopropyl group being more preferred.

When $R_{11}$ in general formula (2) as $R_8$ is a hydroxy group, the substituted straight-chained or branched alkenyl group having 2–6 carbon atoms as $R_{12}$ in general formula (2) is preferably a branched alkenyl group which has 3–5 carbon atoms and which is substituted with at least one fluorine atom.

When $R_{11}$ in general formula (2) as $R_8$ is a hydroxy group, the substituted straight-chained or branched alkynyl group having 2–6 carbon atoms as $R_{12}$ in general formula (2) is a straight-chained or branched alkynyl group which has 3–5 carbon atoms and which is substituted with at least one fluorine atom.

When $R_{11}$ in general formula (2) as $R_8$ is a hydroxy group or a halogen atom, the straight-chained or branched acyl group having 2–6 carbon atoms as $R_{12}$ in general formula (2) is preferably an acetyl group, a propionyl group, a butyryl group, an isobutyryl group or a pivaloyl group.

When $R_{11}$ in general formula (2) as $R_8$ is a hydroxy group or a halogen atom, the straight-chained or branched alkylsulfonyl group having 1–6 carbon atoms as $R_{12}$ in general formula (2) is preferably a methanesulfonyl group, an ethanesulfonyl group, an isopropylsulfonyl group or a tert-butylsulfonyl group.

When $R_{11}$ in general formula (2) as $R_8$ is a hydroxy group or a halogen atom, the amino group mono- or di-substituted with a straight-chained or branched alkyl group having 1–5 carbon atoms as $R_{12}$ in general formula (2) is preferably a dimethylamino group, an ethylmethylamino group, a diethylamino group, an isopropylamino group, an ispropylmethylamino group, a tert-butylamino group, a tert-butylmethylamino group, a sec-butylamino group, a sec-butylmethylamino group, an isobutylamino group or an isobutylmethylamino group.

When $R_{11}$ in general formula (2) as $R_8$ is a halogen atom, the alkyl group of the optionally substituted straight-chained or branched alkyl group having 1–6 carbon atoms as $R_{12}$ in general formula (2) is preferably a straight-chained or branched alkyl group having 1–4 carbon atoms, as specifically exemplified by an isopropyl group and a tert-butyl group.

When $R_{11}$ in general formula (2) as $R_8$ is a halogen atom, the alkenyl group of the optionally substituted straight-chained or branched alkenyl group having 2–6 carbon atoms as $R_{12}$ in general formula (2) is preferably a branched alkenyl group having 3–5 carbon atoms.

When $R_{11}$ in general formula (2) as $R_8$ is a halogen atom, the alkynyl group of the optionally substituted straight-chained or branched alkynyl group having 2–6 carbon atoms as $R_{12}$ in general formula (2) is preferably a straight-chained or branched alkynyl group having 3–5 carbon atoms.

When $R_{11}$ in general formula (2) as $R_8$ is a halogen atom, the substituents for the optionally substituted straight-chained or branched alkyl group having 1–6 carbon atoms, the optionally substituted straight-chained or branched alkenyl group having 2–6 carbon atoms and the optionally substituted straight-chained or branched alkynyl group having 2–6 carbon atoms as $R_{12}$ in general formula (2) are preferably a halogen atom, with a fluorine atom being particularly preferred. The alkyl, alkenyl and alkynyl groups may optionally have one or more of these substituents, which may be the same or different.

When $R_{11}$ in general formula (2) as $R_8$ is a halogen atom, the optionally substituted straight-chained or branched alkyl group having 1–6 carbon atoms as $R_{12}$ in general formula (2) is preferably an isopropyl group, a tert-butyl group, a perfluoroisopropyl group, a 1,3-difluoro-2-propyl group or a perfluoro-tert-butyl group, with a tert-butyl group being particularly preferred.

When $R_{11}$ in general formula (2) as $R_8$ is a halogen atom, the optionally substituted straight-chained or branched alkenyl group having 2–6 carbon atoms as $R_{12}$ in general formula (2) is preferably a unsubstituted branched alkenyl group having 3–5 carbon atoms.

When $R_{11}$ in general formula (2) as $R_8$ is a halogen atom, the optionally substituted straight-chained or branched alkynyl group having 2–6 carbon atoms as $R_{12}$ in general formula (2) is preferably a unsubstituted straight-chained or branched alkynyl group having 3–5 carbon atoms.

While $R_8$ has the definitions set forth above, $R_8$ is preferably a 3-acetyl-4-hydroxyphenyl group, a 4-hydroxy-3-propionylphenyl group, a 3-butyryl-4-hydroxyphenyl group, a 4-hydroxy-3-perfluoroisopropylphenyl group, a 3-dimethylamino-4-hydroxyphenyl group, a 3-tert-butyl-4-fluorophenyl group, a 3-methylindol-5-yl group, a 3,3-dimethylindolin-5-yl group, a 3,3-dimetylinidolinon-5-yl group, a 5-tert-butyl-4-carbamoylfuran-2-yl group, a 5-tert-butyl-4-sulfamoylfuran-2-yl group, a 5-tert-butyl-4-hydroxymethylfuran-2-yl group, a 2-tert-butyl-pyridin-4-yl group, a 5-tert-butyl-4-carboxyfuran-2-yl group, with a 3-butyryl-4-hydroxyphenyl group, a 3-tert-butyl-4-fluorophenyl group, a 3-metylindol-5-yl group and a 5-tert-butyl-4-carboxyfuran-2-yl group being particularly preferred.

X is preferably a carbonyl group or a methylene group.
Y is preferably a carbonyl group or a methylene group.
Preferred examples of the compounds of the general formula (1)

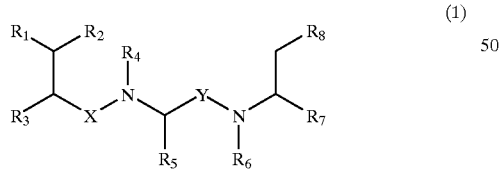

wherein $R_1$, $R_2$, $R_3$, $R_4$, $R_5$, $R_6$, $R_7$, $R_8$, X and Y have the same meanings as defined above include Phe-N-Me-Val-Phe(3-acetyl-4-hydroxy)-NH$_2$, Phe-N-Me-Val-Phe(4-hydroxy-3-propionyl)-NH$_2$, Phe-N-Me-Val-Phe(4-hydroxy-3-isobutyryl)-NH$_2$, Phe-N-Me-Val-[3-(5-tert-butyl-4-sulfamoyl-2-furyl)]Ala-NH$_2$, Phe-N-Me-Val-[3-(3-methylindol-5-yl)]Ala-NH$_2$, Phe-N-Me-Val-N-Me-[3-(3-methylindol-5-yl)]Ala-NH$_2$, Phe-N-Me-Val-Phe(3-tBu-4-F)-NH$_2$, Phe-N-Me-Val-N-Me-Phe(3-tBu-4-F)-NH$_2$ and Phe-N-Me-Val-N-Me-Phe(4-hydroxy-3-isobutyryl)-NH$_2$ and more preferred examples are Phe-N-Me-Val-Phe(4-hydroxy-3-isobutyryl)-NH$_2$, Phe-N-Me-Val-[3-(3-methylindol-5-yl)]Ala-NH$_2$, Phe-N-Me-Val-N-Me-[3-(3-methylindol-5-yl)]Ala-NH$_2$, Phe-N-Me-Val-Phe(3-tBu-4-F)-NH$_2$, Phe-N-Me-Val-N-Me-Phe(3-tBu-4-F)-NH$_2$ and Phe-N-Me-Val-N-Me-Phe(4-hydroxy-3-isobutyryl)-NH$_2$.

Salt-forming acids include inorganic acids such as hydrochloric acid, hydrobromic acid, hydroiodic acid, sulfuric acid and phosphoric acid, as well as organic acids such as acetic acid, oxalic acid, maleic acid, fumaric acid, citric acid, tartaric acid, methanesulfonic acid and trifluoroacetic acid.

The compounds of the present invention can occur as optical isomers and the respective optical isomers and mixtures thereof are all included within the scope of the invention.

The compounds of the present invention can also be obtained as hydrates.

On the pages that follow, the present invention is described more specifically and the amino acids that constitute peptides, the amino acids protected by protecting groups, the protecting groups and reagents are represented by the following abbreviations:

Ala: alanine, Val: valine, Phe: phenylalanine, Z: benzyloxycarbonyl, Boc: tert-butoxycarbonyl, BOP: benzotriazol-1-yl-oxy-tris(dimethylamino)phosphonium hexafluorophosphate, PyCIU: chloro-N,N,N',N'-bis(tetramethylene)formamidinium hexafluorophosphate, DIC: N,N'-diisopropylcarbodiimide, HOBT: 1-hydroxylbenzotriazole monohydrate, NMM: N-methylmorpholine, TEA: triethylamine, DIEA: diisopropylethylamine, TFA: trifluoroacetic acid, THF: tetrahydrofuran, DMF: N,N-dimethyiformamide and CMPI: 2-chloro-1-methylpyridinium iodide.

The subject application claims priority on the basis of Japanese Patent Application No. 10-307784 and all disclosures in its specification shall be incorporated herein by reference.

BEST MODE FOR CARRYING OUT THE INVENTION

The compounds represented by the general formula (1)

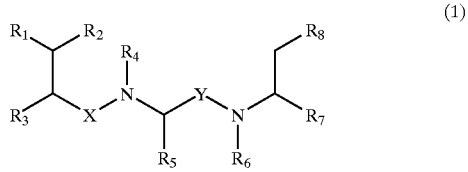

wherein $R_1$, $R_2$, $R_3$, $R_4$, $R_5$, $R_6$, $R_7$, $R_8$, X and Y have the same meanings as defined above can basically be produced by binding Compound (I), Compound (II) and Compound (III), which are represented by the following formulae and in which functional groups other than those involved in bond formation are protected as required:

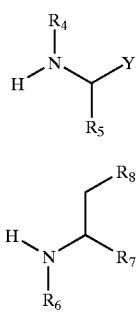

The compound of the general formula (1) may be produced by first binding Compound (II) and Compound (III) and then binding the resultant compound with Compound (I). Alternatively, the compound of formula the (1) may be produced by first binding Compound (I) and Compound (II) and then binding the resultant compound with Compound (III).

The compounds of the present invention may be produced by either the solid-phase process or the liquid-phase process. In the production by the solid-phase process, an automatic organic synthesizer can be used but it may be replaced by the manual procedure.

Almost all amino acids that are used for the production of the compounds of the present invention are commercially available and readily purchasable. Those which are not commercially available can be produced by well-known established methods such as the Strecker synthesis, the Bucherer method, the acetamido malonic ester method, the method of alkylating an amino group protected glycine ester and the Z-α-phosphonoglycine trimethylester method.

Compound (I), if it has a functional group such as an amino group and a hydroxy group, with the functional group being protected, is a carboxylic acid (X is —$CO_2H$), an aldehyde (X is —CHO), an alkylhalide (X is —$CH_2$—Hal), a sulfonate (X is —$CH_2$—$OSO_2R$) or the like. In this case, bond can be formed by reacting X of Compound (I) with the amino group of Compound (II).

Compound (II) can in almost all cases be derived from an α-amino acid and Y is a carboxyl group (—$CO_2H$), a formyl group (—CHO), a halomethyl group (—$CH_2$—Hal), a sulfonyloxymethyl group ($RSO_2O$—$CH_2$—) or the like. The amino group of Compound (II) is reacted with X of Compound (I) to form bond and Y of Compound (II) is reacted with the amino group of Compound (III) to form bond.

Compound (III) is an ethylamine derivative and can be derived from an amino acid if $R_7$ is not hydrogen. If $R_7$ is hydrogen, Compound (III) can be synthesized by introducing an amino group to, for example, $R_8$—$CH_2CHO$, which may be obtained from $R_8$—CHO via, for example, a homologation reaction. The amino group of Compound (III) is reacted with Y of Compound (II) to form bond.

When X or Y is a carboxyl group, various methods known in peptide synthesis may be used to activate the carboxyl group for condensation with the amino group and such methods include the use of BOP, the use of PyClU, the use of bromotripyrrolidino phosphonium hexafluorophosphate (PyBrop), the use of chlorotripyrrolidino phosphonium hexafluorophosphate (PyClop), the use of O-(7-azabenzotriazol-1-yl)-1,1,3,3-tetramethyluronium hexafluorophosphate (HATU), the use of DIC, the use of N-ethyl-N'-3-dimethylaminopropyl carbodiimide (WSCI), the use of dicyclohexyl carbodiimide (DCC), the use of diphenylphosphorylazide (DPPA), the combination of one of these reagents with HOBT or N-hydroxysuccinimide (HONSu), the mixed acid anhydride method using isobutyl chloroformate or the like, the method of changing the carboxyl group to a pentafluorophenyl ester (OPfp), a p-nitrophenyl ester (ONP) or an N-hydroxysuccinimide ester (OSu), and the combination of one of these methods with HOBT. If necessary, a base such as TEA, DIEA, NMM or 4-dimethylaminopyridine (DMAP) may be added to accelerate the reaction.

A compound in which X or Y is a methylene group can be synthesized from an aldehyde by a conventional reductive bond forming reaction with an amino group or from a halide or sulfonate by substitution reaction with an amino group.

The compounds of the present invention can also be produced by applying the specific methods of production to be described in the examples that follow.

EXAMPLES

On the pages that follow, the production of the compounds of the invention is described more specifically by reference to examples, to which the invention is by no means limited.

In order to demonstrate the utility of the compounds of the invention, typical examples of them were subjected to pharmacological tests on the motilin receptor antagonistic action and the results are described under Tests. The chemical structural formulae or chemical names of the compounds produced in the examples are set forth in Tables A-1 to A-4.

TABLE A-1

| Ex. No. | Structural Formula or Chemical Name |
|---|---|
| 1 | Phe-N-Me-Val-Phe(3-acetyl-4-hydroxy)-$NH_2$ |
| 2 | Phe-N-Me-Val-Phe(4-hydroxy-3-propionyl)-$NH_2$ |
| 3 | Phe-N-Me-Val-Phe(4-hydroxy-3-isobutyryl)-$NH_2$ |
| 4 | Phe-N-Me-Val-[3-(5-tert-butyl-4-sulfamoyl-2-furyl)]Ala-$NH_2$ |
| 5 | Phe-N-Me-Val-[3-(3-methylindol-5-yl)]Ala-$NH_2$ |
| 6 | Phe-N-Me-Val-N-Me-[3-(3-methylindol-5-yl]Ala-$NH_2$ |
| 7 | Phe-N-Me-Val-Phe(3-tBu-4-F)-$NH_2$ |
| 8 | Phe-N-Me-Val-N-Me-Phe(3-tBu-4-F)-$NH_2$ |
| 9 | Phe-N-Me-Val-N-Me-Phe(4-hydroxy-3-isobutyryl)-$NH_2$ |
| 10 | Phe-N-Me-Val-N-Me-[3-(5-tert-butyl-4-hydroxymethylfuran-2-yl)]Ala-$NH_2$ |
| 11 | Phe-N-Me-Val-Tyr(3-$NMe_2$)-$NH_2$ |
| 12 | Phe-N-Me-Val-N-Me-[3-(5-tert-butyl-4-carboxyfuran-2-yl)]Ala-$NH_2$ |
| 13 | Phe-N-Me-Val-N-Me-[3-(5-tert-butyl-4-carbamoylfuran-2-yl)]Ala-$NH_2$ |
| 14 | Phe-N-Me-Val-N-Me-Tyr(3-iso-$C_3F_7$)-$NH_2$ |

TABLE A-2

| Ex. No. | Structural Formula |
|---|---|
| 1 | |
| 2 | |
| 3 | |
| 4 | |
| 5 | |
| 6 | |

TABLE A-3

| Ex. No. | Structural Formula |
|---|---|
| 7 | (Phe-N(CH₃)-Val-NH-CH(CH₂-[4-F,3-t-Bu-C₆H₃])-C(O)NH₂) |
| 8 | (Phe-N(CH₃)-Val-N(CH₃)-CH(CH₂-[4-F,3-t-Bu-C₆H₃])-C(O)NH₂) |

TABLE A-4

| Ex. No. | Structural Formula |
|---|---|
| 9 | (Phe-N(CH₃)-Val-N(CH₃)-CH(CH₂-[4-OH,3-(isobutyryl)-C₆H₃])-C(O)NH₂) |
| 10 | (Phe-N(CH₃)-Val-N(CH₃)-CH(CH₂-[5-t-Bu-4-(hydroxymethyl)-furan-2-yl])-C(O)NH₂) |
| 11 | (Phe-N(CH₃)-Val-N(CH₃)-CH(CH₂-[4-OH,3-NMe₂-C₆H₃])-C(O)NH₂) |

TABLE A-4-continued

| Ex. No. | Structural Formula |
|---|---|
| 12 | (structure: Phe-N-Me-Val-N-Me-[3-(2-t-Bu-furan-3-carboxylic acid-5-ylmethyl)]-Ala-NH₂) |
| 13 | (structure: Phe-N-Me-Val-N-Me-[3-(2-t-Bu-furan-3-carboxamide-5-ylmethyl)]-Ala-NH₂) |
| 14 | (structure: Phe-N-Me-Val-N-Me-[3-(4-hydroxy-3-(bis-trifluoromethyl-fluoro)phenylmethyl)]-Ala-NH₂) |

In the following examples, mass spectra (MS) were taken by EI-MS using SHIMADZU GCMS-QP5050A.

NMR was measured by the following method a or b.

a method: JEOL JNM-EX-270 (270 MHz) was used as a measuring instrument.

b method: Varian MERCURY 300 (300 MHz) was used as a measuring instrument.

Example 1
Phe-N-Me-Val-Phe(3-acetyl-4-hydroxy)-NH₂

(1) Synthesis of N-Me-Val-Phe(3-acetyl-4-hydroxy)-NH₂

To a mixture of L-3-(3-acetyl-4-hydroxyphenyl)alanine hydrochloride (J. Org. Chem., 52, 5283 (1987)) (0.40 g, 1.54 mmol), sodium carbonate (0.69 g, 6.47 mmol), 1,4-dioxane (4 ml) and water (6 ml), benzyl chloroformate (0.26 ml, 1.85 mmol) was added under cooling with ice, followed by stirring for 2 hours at room temperature. The mixture was mixed with water and washed with methylene chloride; the aqueous layer was acidified by adding a 5N aqueous HCl solution and extracted with methylene chloride. The organic layer was dried over anhydrous magnesium sulfate and evaporated to remove the solvent under reduced pressure, giving N-benzyloxycarbonyl-L-3-(3-acetyl-4-hydroxyphenyl)alanine (0.37 g, 67%).

To a solution of the thus obtained compound (0.36 g, 1.0 mmol) in DMF (4 ml), NMM (0.13 ml, 1.20 mmol) and then ethyl chloroformate (0.11 ml, 1.20 mmol) were added under cooling with ice. After stirring for 20 min., gaseous ammonia was blown into the mixture for 25 min. After being returned to room temperature and left standing for a while, the mixture was mixed with a saturated aqueous NaHCO₃ solution and extracted with ethyl acetate. The organic layer was washed with water and saturated brine, dried over anhydrous magnesium sulfate and evaporated to remove the solvent under reduced pressure, giving N-benzyloxycarbonyl-L-3-(3-acetyl-4-hydroxyphenyl)alaninamide (162 mg, 45%).

To a solution of the thus obtained compound (0.16 g, 0.449 mmol) in methylene chloride (2 ml), a 33% solution of hydrogen bromide-acetic acid (2 ml) was added under cooling with ice, followed by stirring for 1 hour at room temperature. The reaction mixture was evaporated under reduced pressure; to a solution of the thus obtained residue (0.16 g), Z-N-Me-Val-OH (143 mg, 0.539 mmol), HOBT (89 mg, 0.584 mmol) and NMM (0.074 ml, 0.674 mmol) in DMF (2 ml), DIC (0.091 ml, 0.584 mmol) was added under cooling with ice. The resulting mixture was stirred for 20 hours at room temperature, mixed with NMM (0.074 ml, 0.674 mol) and stirred for further 5 hours. The reaction mixture was diluted with ethyl acetate and washed with a saturated aqueous NaHCO₃ solution, water and saturated brine in that order. The organic layer was dried over anhydrous magnesium sulfate and evaporated to remove the solvent under reduced pressure; the thus obtained residue was subjected to silica gel column chromatography (developing solvent: chloroform:methanol:aqueous ammonia=50:1:0.1) to give Z-N-Me-Val-Phe(3-acetyl-4-hydroxy)-NH₂ (172 mg, 82%).

To a solution of the thus obtained compound (165 mg, 0.351 mmol) in methylene chloride (2 ml), a 33% solution of hydrogen bromide-acetic acid (2 ml) was added under cooling with ice, followed by stirring for 100 min. at room temperature. The reaction mixture was evaporated under reduced pressure; the thus obtained residue was mixed with water, extracted with chloroform, dried over anhydrous magnesium sulfate and evaporated to remove the solvent under reduced pressure; the thus obtained residue was subjected to silica gel column chromatography (developing solvent: chloroform:methanol:aqueous ammonia=40:1:0.1) to give the titled compound (62 mg, 30%).

NMR (method a, CDCl$_3$): δ 0.71(3H,d,J=6.9 Hz), 0.86 (3H,d,J=6.9 Hz), 1.90–2.02(1H,m), 2.32(3H,s), 2.62(3H,s), 2.76(1H,d,J=4.6 Hz), 3.01(1H,dd,J=8.1,14.2 Hz), 3.14(1H, dd,J=6.8,14.2 Hz), 4.69(1H,dd,J=7.9,15.2 Hz), 5.55(1H, brs),6.30(1H,brs), 6.91(1H,d,J=8.6 Hz), 7.36(1H,dd,J=2.0, 8.6 Hz), 7.61(1H,d,J=2.0 Hz), 7.76(1H,d,J=8.3 Hz), 12.2 (1H,s)

(2) Synthesis of Phe-N-Me-Val-Phe(3-acetyl-4-hydroxy)-NH$_2$

To a solution of N-Me-Val-Phe(3-acetyl-4-hydroxy)-NH$_2$ (60 mg, 0.179 mmol), Boc-Phe-OH (119 mg, 0.447 mmol) and HOBT (55 mg, 0.358 mmol) in DMF 2 ml, DIC (0.056 ml, 0.358 mmol) was added under cooling with ice, followed by stirring for overnight at room temperature. The reaction mixture was diluted with ethyl acetate and washed with a saturated aqueous NaHCO$_3$ solution, water and saturated brine in that order. The organic layer was dried over anhydrous magnesium sulfate and evaporated to remove the solvent under reduced pressure; the thus obtained residue was subjected to silica gel column chromatography (developing solvent: chloroform:methanol:aqueous ammonia=60:1:0.1) to give Boc-Phe-N-Me-Val-Phe(3-acetyl-4-hydroxy)-NH$_2$(63 mg, 60%).

To a solution of the thus obtained compound (60 mg, 0.103 mmol) in methylene chloride (1 ml), TFA (0.5 ml) was added, followed by stirring for 15 min. at room temperature. The reaction mixture was evaporated under reduced pressure; the thus obtained residue was mixed with a 4N HCl/1,4-dioxane solution (2 ml) and evaporated to remove the solvent under reduced pressure. The thus obtained residue was mixed with ether and filtered to collect the insoluble matter, giving a hydrochloride of the titled compound (50 mg, 94%).

EI-MS:482(M$^+$-HCl) NMR (method a, CDCl$_3$): δ 0.61–0.93(6H,m), 1.9–2.1(1H,m), 2.32(9/5H,s), 2.43(6/5H, s), 2.6–3.1(3H,m), 3.2–3.7(2H,m), 3.57(3H,s), 4.3–4.5(3H, m), 4.65(1H,d,J=11.2 Hz), 6.71(1H,d,J=7.6 Hz), 6.84(1H,d, J=8.6 Hz), 7.0–7.6(6H,m), 7.97(1H,d,J=11.8 Hz), 8.29(3H, brs), 8.77(1H,brs), 11.8(1H,s)

Example 2

Phe-N-Me-Val-Phe(4-hydroxy-3-propionyl)-NH$_2$ (1) Synthesis of N-benzyloxycarbonyl-L-3-(4-hydroxy-3-propionylphenyl)alaninamide To a solution of L-tyrosine (1.45 g, 8.0 mmol) in nitrobenzene (30 ml), anhydrous aluminum chloride (4.23 g, 31.5 mmol) was added, followed by stirring at room temperature for 40 min. The mixture was mixed with propionyl chloride (0.83 ml, 9.6 mmol) and stirred at 100° C. for 6 hours. After being returned to room temperature, the reaction mixture was poured into a mixture of ice water (50 ml) and concentrated hydrochloric acid (8 ml) under stirring. The aqueous layer was separated from the organic layer, washed with ethyl acetate and concentrated to approximately 20 ml under reduced pressure. The concentrated aqueous layer was cooled with ice, and filtered to collect the thus formed precipitate, which was dried to give L-3-(4-hydroxy-3-propionylphenyl)alanine hydrochloride (1.98 g, 90%).

To a mixture of the thus obtained compound (1.98 g, 7.23 mmol), sodium carbonate (3.83 g, 36.2 mmol), 1,4-dioxane (12 ml) and water (18 ml), benzyl chloroformate (1.14 ml, 7.96 mmol) was added under cooling with ice, followed by stirring for 2 hours at room temperature. The mixture was mixed with water and washed with methylene chloride; the aqueous layer was acidified by adding concentrated hydrochloric acid and extracted with methylene chloride. The organic layer was dried over anhydrous magnesium sulfate and evaporated to remove the solvent under reduced pressure to give N-benzyloxycarbonyl-L-3-(4-hydroxy-3-propionylphenyl)alanine (1.75 g, 65%).

To a solution of the thus obtained compound (1.75 g, 4.72 mmol) in DMF (15 ml), NMM (0.62 ml, 5.66 mmol) was added under cooling with ice, followed by the addition of ethyl chloroformate (0.54 ml, 5.66 mmol). After stirring for 25 min., gaseous ammonia was blown into the mixture for 40 min. The mixture was returned to room temperature, left standing as it was for a while, mixed with a saturated NaHCO$_3$ solution and extracted with ethyl acetate. The organic layer was washed with water and saturated brine, dried over anhydrous magnesium sulfate and evaporated to remove the solvent under reduced pressure to give the titled compound (1.07 mg, 61%).

NMR (method a, DMSO-d$_6$): δ 1.08(3H,t,J=7.3 Hz), 2.70(1H,dd,J=11.2,13.2 Hz), 2.94–3.08(3H,m), 4.10–4.14 (1H,m), 4.93(2H,dd,J=12.0,20.3 Hz), 6.87(1H,d,J=8.3 Hz), 7.08(1H,s), 7.20–7.34(5H,m), 7.41(1H,s), 7.45(1H,d,J=8.3 Hz) 7.83(1H,s), 11.9(1H,s)

(2) Synthesis of N-Me-Val-Phe(4-hydroxy-3-propionyl)-NH$_2$

To a solution of N-benzyloxycarbonyl-L-3-(4-hydroxy-3-propionylphenyl)alaninamide (0.50 g, 1.35 mmol) in methanol (13 ml), 10% palladium-carbon (0.05 g) was added, followed by stirring for 2.5 hours in a hydrogen atmosphere. After removing the catalyst by filtration, the filtrate was concentrated and the thus obtained residue was subjected to silica gel column chromatography (developing solvent: chloroform:methanol:aqueous ammonia=20:1:0.1) to give L-3-(4-hydroxy-3-propionylphenyl)alaninamide (0.23 g, 72%).

To a solution of the thus obtained compound (0.22 g, 0.931 mmol), Z-N-Me-Val-OH (296 mg, 1.12 mmol) and HOBT (185 mg, 1.21 mmol) in DMF (4 ml), DIC (0.19 ml, 1.21 mmol) was added under cooling with ice, followed by stirring for overnight at room temperature. The reaction mixture was diluted with ethyl acetate and washed with a saturated aqueous NaHCO$_3$ solution, water and saturated brine in that order. The organic layer was dried over anhydrous magnesium sulfate and evaporated to remove the solvent under reduced pressure; the thus obtained residue was subjected to silica gel column chromatography (developing solvent ethyl acetate:n-hexane=2:1) to give Z-N-Me-Val-Phe(4-hydroxy-3-propionyl)-NH$_2$(0.42 g, 93%).

To a solution of the thus obtained compound (0.41 g, 0.848 mmol) in methanol (8 ml), 10% palladium-carbon (0.05 g) was added, followed by stirring for 2 hours in a hydrogen atmosphere. After removing the catalyst from the reaction mixture by filtration, the filtrate was concentrated to give the titled compound (0.31 g, quant.).

NMR (method a, DMSO-d$_6$): δ 0.69(3H,t,J=6.6 Hz), 0.74(3H,d,J=6.9 Hz), 1.12(3H,t,J=7.3 Hz), 1.57–1.70(1H, m), 1.97(3H,s), 2.76(1H,dd,10.0,13.5 Hz), 2.96(1H,dd,J= 4.3,13.5 Hz), 3.08(2H,q,J=7.3 Hz), 3.60–3.68(1H,m), 4.54–4.62(1H,m), 5.47(1H,d,J=6.9 Hz), 6.84(1H,m), 7.06 (1H,s), 7.39(1H,dd,J=2.0,8.6 Hz), 7.46(1H,s), 7.78(1H,d,J= 1.7 Hz), 7.93(1H,d,J=8.9 Hz), 11.80(1H,brs)

(3) Synthesis of Phe-N-Me-Val-Phe(4-hydroxy-3-propionyl)-$NH_2$
(A) and (B)

To a solution of N-Me-Val-Phe(4-hydroxy-3-propionyl)-$NH_2$ (0.30 g, 0.859 mmol) and Boc-Phe-OH (342 mg, 1.29 mmol) in methylene chloride (6 ml), BOP (646 mg, 1.46 mmol) and TEA (0.30 ml, 2.15 mmol) were added in that order under cooling with ice, followed by stirring for overnight at room temperature. The reaction mixture was diluted with methylene chloride and washed with a saturated aqueous $NaHCO_3$ solution and water. The organic layer was dried over anhydrous magnesium sulfate and evaporated to remove the solvent under reduced pressure; the thus obtained residue was subjected to silica gel column chromatography (developing solvent: ethyl acetate:n-hexane= 2:1) to give Boc-Phe-N-Me-Val-Phe(4-hydroxy-3-propionyl)-$NH_2$ (280 mg, 55%).

To a solution of the thus obtained compound (275 mg, 0.461 mmol) in methylene chloride (3 ml), TFA (1.5 ml) was added, followed by stirring for 20 min. at room temperature. The reaction mixture was evaporated under reduced pressure; the thus obtained residue was mixed with a saturated aqueous $NaHCO_3$ solution, extracted with methylene chloride, dried over anhydrous magnesium sulfate and evaporated to remove the solvent under reduced pressure; the thus obtained residue was subjected to silica gel column chromatography (developing solvent: chloroform:methanol:aqueous ammonia=40:1:0.1) to give Phe-N-Me-Val-Phe(4-hydroxy-3-propionyl)-$NH_2$ (138 mg, 60%) as a mixture of diastereoisomers. The mixture of diastereoisomers was subjected to HPLC (HPLC: Gilson 306, column: YMC-Pack ODS (120 angstrom, 250×20 mm I.D.), eluting solvent: 0.1% TFA, the linear gradient is made by distilled water and 0.1% TFA acetonitrile (35–50% acetonitrile, 45 min., flow rate 10 ml/min, detection at 280 nm (UV))) for further purification to give TFA salts of the titled compounds, A (86 mg) being eluted first and then B (27 mg).

(A)

EI-MS: 479($M^{+-17}$) NMR (method a, DMSO-$d_6$): δ 0.74 (3H,d,J=6.3 Hz), 0.89(3H,d,J=6.3 Hz), 1.08(3H,t,J=7.3 Hz), 1.91–2.08(1H,m), 2.39(3H,s), 2.63(1H,dd,J=8.4,13.7 Hz), 2.80–3.04(3H,m), 3.07(2H,q,J=7.3 Hz), 4.32–4.43(1H,m), 4.64(1H,d,J=10.9 Hz), 6.76–6.90(2H,m), 7.02–7.50(6H,m), 7.91(1H,s), 8.1–8.3(3H,m), 11.8(1H,s)

(B)

EI-MS:479($M^{+-17}$) NMR(method a, DMSO-$d_6$): δ 0.56 (9/5H,d,J=6.6 Hz), 0.81(6/5H,d,J=6.6 Hz), 0.84(9/5H,d,J= 6.6 Hz), 0.97(6/5H,d,J=6.6 Hz), 1.02(6/5H,d,J=7.3 Hz), 1.12(9/5H,t,J=7.3 Hz), 1.95–2.30(1H,m), 2.5–2.6(1H,m), 2.7–3.0(3H,m), 3.10(2H,q,J=7.3 Hz), 4.12(2/5H,d,J=10.6 Hz), 4.35–4.78(2H,m), 4.51(3/5H,d,J=10.6 Hz), 6.55(1/2H, d,J=8.3 Hz), 6.82–6.95(3/2H,m), 7.02–7.41(5H,m), 7.64(1/ 2H,s), 7.74(1/2H,s), 7.87–8.10(3/2H,m), 8.17(1H,brs), 8.42 (1/2H,d,J=7.6 Hz), 11.6(2/5H,s), 11.8(3/5H,s)

Example 3

Phe-N-Me-Val-Phe(4-hydroxy-3-isobutyryl)-$NH_2$ (1) Synthesis of N-benzyloxycarbonyl-L-3-(4-hydroxy-3-isobutyrylphenyl)alaninamide To a solution of L-tyrosine (1.45 g, 8.0 mmol) in nitrobenzene (35 ml), anhydrous aluminum chloride (4.23 g, 31.5 mmol) was added, followed by stirring at room temperature for 45 min. The mixture was mixed with isobutyryl chloride (1.0 ml, 9.6 mmol) and stirred at 100° C. for 6 hours. The reaction mixture was returned to room temperature and then poured into a mixture of ice water (50 ml) and concentrated hydrochloric acid (8 ml) under stirring. The aqueous layer was separated from the organic layer, washed with ethyl acetate and concentrated under reduced pressure. The concentrated aqueous layer was cooled with ice, filtered to collect the thus formed precipitate, which was dried to give L-3-(4-hydroxyphenyl-3-isobutyryl)alanine hydrochloride (1.43 g).

To a mixture of the thus obtained compound (1.40 g, 4.86 mmol), sodium carbonate (2.69 g, 25.4 mmol), 1,4-dioxane (12 ml) and water (18 ml), benzyl chloroformate (0.76 ml, 5.35 mmol) was added under cooling with ice, followed by stirring for 100 min. at room temperature. The mixture was mixed with water and washed with methylene chloride; the aqueous layer was acidified by adding concentrated hydrochloric acid and extracted with methylene chloride. The organic layer was dried over anhydrous magnesium sulfate and evaporated to remove the solvent under reduced pressure, giving N-benzyloxycarbonyl-L-3-(4-hydroxyphenyl-3-isobutyryl-)alanine (1.85 g).

To a solution of the thus obtained compound (1.78 g, 4.62 mmol) in DMF (15 ml), NMM (0.61 ml, 5.55 mmol) and then ethyl chloroformate (0.53 ml, 5.55 mmol) were added under cooling with ice. After stirring for 30 min., gaseous ammonia was blown into the mixture for 30 min. The mixture was returned to room temperature, left standing for a while, mixed with a saturated aqueous $NaHCO_3$ solution and extracted with ethyl acetate. The organic layer was washed with water and saturated brine, dried over anhydrous magnesium sulfate and evaporated to remove the solvent under reduced pressure; the thus obtained residue was subjected to silica gel column chromatography (developing solvent: ethyl acetate:n-hexane=2:1) to give the titled compound (0.40 g, 13%, in 3 steps).

NMR (method a, $CDCl_3$): δ 1.21(6H,d,J=6.6 Hz), 3.05 (2H,d,J=6.6 Hz), 3.55(1H,m), 4.41(1H,m), 5.08(2H,dd,J= 12.2,14.2 Hz), 5.37(1H,d,J=7.9 Hz), 5.53(1H,brs), 5.85(1H, brs), 6.92(1H,d,J=8.6 Hz), 7.26–7.44(6H,m), 7.61(1H,s), 12.4(1H,s)

(2) Synthesis of N-Me-Val-Phe(4-hydroxy-3-isobutyryl)-$NH_2$

To a solution of N-benzyloxycarbonyl-L-3-(4-hydroxy-3-isobutyrylphenyl)alaninamide (0.40 g, 1.04 mmol) in methylene chloride (3 ml), a solution of 33% hydrogen bromide-acetic acid (3 ml) was added under cooling with ice, followed by stirring for 1.5 hours at room temperature. The reaction mixture was mixed with methanol and evaporated under reduced pressure; to a solution of the thus obtained residue, Z-N-Me-Val-OH (331 mg, 1.25 mmol), HOBT (207 mg, 1.35 mmol) and NMM (0.29 ml, 2.60 mmol) in DMF (5 ml), DIC (0.21 ml, 1.35 mmol) was added under cooling with ice, followed by stirring for overnight at room temperature. The mixture was mixed with NMM (0.29 ml, 2.60 mmol) and 2 hours after that, mixed with Z-N-Me-Val-OH (160 mg) and DIC (0.10 ml), followed by stirring for further 4 hours. The reaction mixture was diluted with ethyl acetate and washed with a saturated aqueous $NaHCO_3$ solution, water and saturated brine in that order. The organic layer was dried over anhydrous magnesium sulfate and evaporated to remove the solvent under reduced pressure; the thus obtained residue was subjected to silica gel column chromatography (developing solvent: ethyl acetate:n-hexane= 2:1) to give Z-N-Me-Val-Phe(4-hydroxy-3-isobutyryl)-$NH_2$ (0.45 g, 83%, in 2 steps).

To a solution of the thus obtained compound (0.43 g, 0.865 mmol) in methanol (8 ml), 10% palladium-carbon (0.06 g) was added, followed by stirring for 4 hours in a hydrogen atmosphere. After removing the catalyst from the reaction mixture by filtration, the filtrate was concentrated to give the titled compound (0.32 g, quant.).

NMR (method a, CDCl$_3$): δ 0.71(3H,t,J=6.6 Hz), 0.86 (3H,d,J=6.9 Hz), 1.24(6H,d,J=6.9 Hz), 1.93–1.99(1H,m), 2.31(3H,s), 2.76(1H,d,J=4.6 Hz), 3.02(1H,dd,J=7.7,14.3 Hz), 3.14(1H,dd,J=7.1,14.0 Hz), 3.55–3.65(1H,m), 4.65 (1H,dd,J=7.7,15.3 Hz), 5.38(1H,brs), 6.20(1H,brs), 6.93 (1H,d,J=8.6 Hz), 7.35(1H,dd,J=2.0,8.6 Hz), 7.67(1H,d,J= 2.0 Hz), 7.73(1H,d,J=8.2 Hz), 12.4(1H,s)

(3) Synthesis of Phe-N-Me-Val-Phe(4-hydroxy-3-isobutyryl)-NH$_2$

To a solution of N-Me-Val-Phe(4-hydroxy-3-isobutyryl)-NH$_2$ (0.31 g, 0.853 mmol) and Boc-Phe-OH (340 mg, 1.28 mmol) in methylene chloride (7 ml), BOP (641 mg, 1.45 mmol) and TEA (0.30 ml, 2.13 mmol) were added in that order under cooling with ice, followed by stirring for overnight at room temperature. The reaction mixture was diluted with methylene chloride and washed with a saturated aqueous NaHCO$_3$ solution and water. The organic layer was dried over anhydrous magnesium sulfate and evaporated to remove the solvent under reduced pressure; the thus obtained residue was subjected to silica gel column chromatography (developing solvent: ethyl acetate:n-hexane= 2:1) to give Boc-Phe-N-Me-Val-Phe(4-hydroxy-3-isobutyryl)-NH$_2$ (304 mg, 58%).

To a solution of the thus obtained compound (300 mg, 0.491 mmol) in methylene chloride (3 ml), TFA (1.5 ml) was added, followed by stirring for 20 min. at room temperature. The reaction mixture was evaporated under reduced pressure; the thus obtained residue was mixed with a saturated aqueous NaHCO$_3$ solution, extracted with methylene chloride, dried over anhydrous magnesium sulfate and evaporated to remove the solvent under reduced pressure. The thus obtained residue was subjected to silica gel column chromatography (developing solvent: chloroform:methanol:aqueous ammonia=40:1:0.1) to give the titled compound (165 mg, 66%).
EI-MS:510(M$^+$)

NMR (method a, CDCl$_3$): δ 0.74(9/5H,d,J=6.9 Hz) 0.82 (6/5H,d,J=6.6 Hz), 0.90(6/5H,d,J=6.9 Hz), 0.94(9/5H,d,J= 6.6 Hz), 1.24(3H,d,J=6.6 Hz), 1.25(3H,d,J=6.6 Hz), 2.20–2.45(1H,m), 2.48–3.12(22/5H,m), 2.72(9/5H,s), 2.86 (6/5H,s), 3.21(3/5H,dd,J=4.7,13.7 Hz), 3.53–3.94(2H,m), 3.96(3/5H,d,J=10.9 Hz), 4.39(2/5H,d,J=11.2 Hz), 4.57–4.66 (1H,m), 5.30(3/5H,brs), 5.42(2/5H,brs), 5.77(3/5H,brs), 5.94(2/5H,brs), 6.84(2/5H,d,J=7.2 Hz), 6.93(2/5H,d,J=8.2 Hz), 6.95(3/5H,d,J=8.6 Hz), 7.12–7.35(6H,m), 7.60(3/5H, s), 7.69(2/5H,s), 9.28(3/5H,d,J=7.9 Hz), 12.4(2/5H,s), 12.5 (3/5H,s)

Example 4
Phe-N-Me-Val-[3-(5-tert-butyl-4-sulfamoyl-2-furyl)]Ala-NH$_2$ (1) Synthesis of Methyl Ester of 5-tert-butyl-4-sulfamoyl-furan-2-carboxylic acid To a solution of methyl ester of 5-tert-butyl-furan-2-carboxylic acid (14.4 g) in chloroform (80 ml), chlorosulfuric acid (6.3 ml) was added, followed by stirring for 7 hours at 80° C. The pH of the reaction mixture was adjusted to 8 by the addition of a 10% aqueous sodium hydroxide solution. The solvent of the reaction mixture was distilled off and the thus obtained residue was mixed with thionyl chloride (60 ml) and DMF (0.5 ml) followed by stirring at 80° C. for 3 hours. The solvent of the reaction mixture was distilled off and the thus obtained residue was mixed with chloroform (50 ml), to which mixture aqueous ammonia (20 ml) was added dropwise under cooling with ice. The reaction mixture was extracted with ethyl acetate and washed with saturated brine. The organic layer was dried over magnesium sulfate and evaporated under reduced pressure to remove the solvent; the thus obtained residue was subjected to silica gel column chromatography (developing solvent: n-hexane:ethyl acetate=2:1) to give the titled compound (2.01 g, 10%).

NMR (method a, CDCl$_3$): δ 1.52(9H,s), 3.89(3H,s), 4.91 (2H,brs), 7.41(1H,s)

(2) Synthesis of 2-tert-butyl-5-hydroxymethyl-furan-3-sulfonamide

Under cooling with ice, a solution of methyl ester of 5-tert-butyl-4-sulfamoyl-furan-2-carboxylic acid (1.90 g) in THF (20 ml) was added dropwise to a suspension of lithium aluminum hydride (0.55 g) in THF (10 ml) over 35 min., followed by stirring for 2 hours. The reaction mixture was diluted with n-hexane, mixed with saturated aqueous ammonium chloride (5 ml) and filtered on Celite, being washed with ethyl acetate. The filtrate was dried over magnesium sulfate and evaporated to remove the solvent; the thus obtained residue was subjected to silica gel column chromatography (developing solvent: n-hexane:ethyl acetate= 1:1) to give the titled compound (1.66 g, 98%).

NMR (b method, CDCl$_3$): δ 1.45(9H,s), 2.31(1H,brs), 4.54(2H,brs), 5.12(2H,brs), 6.57(1H,s)

(3) Synthesis of 2-tert-butyl-5-formyl-furan-3-sulfonamide

At room temperature, 1,1,1-triacetoxy-1,1-dihydro-1,2-benziodoxol-3(1H)-one (0.60 g) was added to a solution of 2-tert-butyl-5-hydroxymethyl-furan-3-sulfonamide (0.30 g) in methylene chloride (10 ml), followed by stirring for 25 min. The reaction mixture was mixed with a 20% aqueous sodium thiosulfate solution, extracted with methylene chloride. The organic layer was washed with a saturated aqueous sodium bicarbonate solution, dried over magnesium sulfate and evaporated under reduced pressure to remove the solvent; the thus obtained residue was subjected to silica gel column chromatography (developing solvent: n-hexane:ethyl acetate=2:1) to give the titled compound (267 mg, 90%).

NMR (method a, CDCl$_3$): δ 1.53(9H,s), 5.18(2H,brs), 7.51(1H,s), 9.56(1H,s)

(4) Synthesis of Methyl Ester of 2-benzyloxycarbonylamino-3-(5-tert-butyl-4-sulfamoyl-2-furyl)acrylic acid At −78° C., (±)-Z-α-phosphonoglycine trimethyl ester (383 mg) was added to a suspension of potassium tert-butoxide (130 mg) in methylene chloride (1.5 ml), followed by stirring for 20 min. To the mixture, a solution of 2-tert-butyl-5-formyl-furan-3-sulfonamide (267 mg) in methylene chloride (4 ml) was added, followed by stirring for 10 min. at −78° C. and then for 2 hours at room temperature. The reaction mixture was mixed with water and extracted with methylene chloride. The organic layer was dried over magnesium sulfate and evaporated under reduced pressure to remove the solvent; the thus obtained residue was subjected to silica gel column chromatography (developing solvent: n-hexane:ethyl acetate=1:1) to give the titled compound (402 mg, 79%).

NMR (method a, CDCl$_3$): δ 1.44(9H,s), 3.80(3H,s), 5.14 (2H,s), 5.18(2H,brs), 6.79(1H,s), 6.87(1H,s), 7.01(1H,s), 7.34(5H,m)

(5) Synthesis of Methyl Ester of 2-amino-3-(5-tert-butyl-4-sulfamoyl-2-furyl)propionic acid To a solution of methyl ester of 2-benzyloxycarbonylamino-3-(5-tert-butyl-4-sulfamoyl-2-furyl)acrylic acid (402 mg) in methanol (5 ml), 20% palladium hydroxide-carbon (0.05 g) was added, followed by stirring for 5 hours at room temperature in a hydrogen atmosphere. The reaction mixture was filtered, being washed with methanol, and the filtrate was evaporated under reduced pressure to remove the solvent. The thus obtained residue was subjected to silica gel column chromatography (developing solvent: chloroform:methanol:aqueous ammonia=100:10:1) to give the titled compound (241 mg, 86%).

NMR (b method, CDCl$_3$): δ 1.43(9H,s), 2.95(1H,dd,J=15.3,6.9), 3.04(1H,dd,J=15.3,5.2), 3.76(3H,s), 3.77(1H,m), 6.43(1H,s)

(6) Synthesis of Z-Phe-N-Me-Val-OH

To a solution of Z-Phe-N-Me-Val-OMe (3.39 g) in dioxane (40 ml), 2N NaOH (4 ml) was added, followed by stirring for 2 hours at 50° C. The reaction mixture was mixed with water and washed with methylene chloride. The aqueous layer was adjusted to pH3 by the addition of 10% hydrochloric acid and extracted with ethyl acetate. The organic layer was dried over sodium sulfate and evaporated under reduced pressure to remove the solvent; the thus obtained residue was subjected to silica gel column chromatography (developing solvent: methylene chloride:methanol=95:5) to give the titled compound (3.03 g, 92%).

NMR (method a, CDCl$_3$): δ 0.65(3/4H,d,J=6.6), 0.78(9/4H,d,J=6.9), 1.01(3H,d,J=6.6), 2.11–2.32(1H,m), 2.79(9/4H,s), 2.89(3/4H,s), 2.90–3.16(2H,m), 4.18(3/4H,d,J=9.6), 4.73(9/4H,d,J=10.6), 4.87–5.12(1H,m), 5.07(2H,s), 5.71(9/4H,d,J=8.6), 5.80(3/4H,d,J=8.6), 7.17–7.37(10H,m)

(7) Synthesis of Z-Phe-N-Me-Val-[3-(5-tert-butyl-4-sulfamoyl-2-furyl)]Ala-OMe

To a solution of Z-Phe-N-Me-Val-OH (359 mg), methyl ester of 2-amino-3-(5-tert-butyl-4-sulfamoyl-2-furyl) propionic acid (241 mg) and HOBT (134 mg) in DMF (6 ml), DIC (0.13 ml) was added under cooling with ice, followed by stirring for 14.5 hours at room temperature. The reaction mixture was mixed with a saturated aqueous NaHCO$_3$ and extracted with ether. The organic layer was washed with a saturated aqueous NH$_4$Cl and saturated brine in that order. The organic layer was dried over sodium sulfate and evaporated under reduced pressure to remove the solvent; the thus obtained residue was subjected to silica gel column chromatography (developing solvent: n-hexane:ethyl acetate=1:1) to give four diastereoisomers A, B, C and D of the titled compound, a mixture AB (176 mg, 32%) being eluted first and then a mixture CD (228 mg, 41%).

(8) Synthesis of Z-Phe-N-Me-Val-[3-(5-tert-butyl-4-sulfamoyl-2-furyl)]Ala-NH$_2$ (AB)

To a solution of Z-Phe-N-Me-Val-[3-(5-tert-butyl-4-sulfamoyl-2-furyl)]Ala-OMe (AB) (176 mg) in methanol (2 ml), aqueous ammonia (1 ml) was added at room temperature, followed by stirring for 16.5 hours. The reaction mixture was mixed with water and extracted with ethyl acetate. The organic layer was washed with saturated brine, dried over sodium sulfate and evaporated under reduced pressure to remove the solvent; the thus obtained residue was subjected to silica gel column chromatography (developing solvent: n-hexane:ethyl acetate=1:3) to give the titled compound (120 mg, 70%).

(9) Synthesis of Z-Phe-N-Me-Val-[3-(5-tert-butyl-4-sulfamoyl-2-furyl)]Ala-NH$_2$ (CD)

To a solution of Z-Phe-N-Me-Val-[3-(5-tert-butyl-4-sulfamoyl-2-furyl)]Ala-OMe (CD) (226 mg) in methanol (2 ml), aqueous ammonia (1 ml) was added at room temperature, followed by stirring for 21 hours. The reaction mixture was mixed with water and extracted with ethyl acetate. The organic layer was washed with saturated brine, dried over sodium sulfate and evaporated under reduced pressure to remove the solvent; the thus obtained residue was subjected to silica gel column chromatography (developing solvent: n-hexane:ethyl acetate=1:4) to give the titled compound (175 mg, 79%).

(10) Synthesis of Phe-N-Me-Val-[3-(5-tert-butyl-4-sulfamoyl-2-furyl)]Ala-NH$_2$ (A) and (B)

To a mixture of Z-Phe-N-Me-Val-[3-(5-tert-butyl-4-sulfamoyl-2-furyl)]Ala-NH$_2$ (AB) (120 mg) in methanol (1 ml), 20% palladium hydroxide-carbon (0.05 g) was added, followed by stirring at room temperature for 2.5 hours in a hydrogen atmosphere. The reaction mixture was filtered, being washed with methanol, and the filtrate was evaporated under reduced pressure to remove the solvent. The thus obtained residue was subjected to silica gel column chromatography (developing solvent: chloroform:methanol:aqueous ammonia=100:10:1) to give two diastereoisomers A and B of Phe-N-Me-Val-[3-(5-tert-butyl-4-sulfamoyl-2-furyl)]Ala-NH$_2$, A (37 mg, 38%) being eluted first and then B (49 mg, 51%).

(A)

EI-MS:549(M$^+$) NMR (method a, CDCl$_3$): δ 0.69(3H,d, J=6.6), 0.92(3H,d,J=6.3), 1.40(9H,s), 2.24–2.34(1H,m), 2.61(3H,s), 2.81–3.16(4H,m), 3.72–3.78(1H,m), 4.00(1H, brd,J=10.9), 4.76–4.79(1H,m), 5.97(1H,brs), 6.21(1H,s), 6.50(1H,brs), 7.15–7.30(5H,m), 9.24(1H,brd,J=7.9)

(B)

EI-MS:549(M$^+$) NMR (method a, CDCl$_3$): δ 0.70(3H,d, J=6.6), 0.90(3H,d,J=6.3), 1.39(9H,s), 2.19–2.23(1H,m), 2.4–3.17(4H,m), 2.92(3H,s), 4.21–4.26(1H,m), 4.54(1H,d, J=10.9), 4.78–4.86(1H,m), 6.24(1H,s), 6.37(1H,brs), 6.56 (1H,brs), 7.17–7.34(5H,m)

(11) Synthesis of Phe-N-Me-Val-[3-(5-tert-butyl-4-sulfamoyl-2-furyl)]Ala-NH$_2$ (C) and (D)

To a solution of Z-Phe-N-Me-Val-[3-(5-tert-butyl-4-sulfamoyl-2-furyl)]Ala-NH$_2$ (CD) (175 mg) in methanol (1 ml), 20% palladium hydroxide-carbon (0.05 g) was added, followed by stirring at room temperature for 19 hours in a hydrogen atmosphere. The reaction mixture was filtered, being washed with methanol and the filtrate was evaporated under reduced pressure to remove the solvent. The thus obtained residue was subjected to silica gel column chromatography (developing solvent: chloroform:methanol:aqueous ammonia=100:10:1) to give the two diastereoisomers of Phe-N-Me-Val-[3-(5-tert-butyl-4-sulfamoyl-2-furyl)]Ala-NH$_2$, C (54 mg, 39%) being eluted first and then D (60 mg, 43%).

(C)

EI-MS:549(M$^+$) NMR (method a, CDCl$_3$): δ 0.70(3/2H, d,J=6.6), 0.79(3H,d,J=6.3), 0.88(3/2H,d,J=6.3), 1.36(9/2H, s), 1.40(9/2H,s), 2.17–2.28(1H,m), 2.50–3.16(4H,m), 2.70 (3/2H,s), 2.98(3/2H,s), 3.72–3.80(1/2H,m), 3.89–3.98(1H, m), 4.29(1/2H,d,J=10.9), 4.53–4.61(1/2H,m), 4.76–4.82(1/2H,m), 6.37(1/2H,s), 6.41(1H,brs), 6.49(1/2H,s), 6.67(1/2H, brs), 6.74(1/2H,brs), 7.11–7.28(5H,m), 7.69(1/2H,brd,J=8.3), 9.36(1/2H,brd,J=7.6)

(D)

EI-MS: 549(M$^+$) NMR (method a, CDCl$_3$): δ 0.57(3H,d, J=6.3), 0.81(3H,d,J=6.3), 1.41(9H,s), 2.05–2.20(1H,m), 2.68–2.76(1H,m), 2.87(3H,s), 2.88–2.96(1H,m), 3.05–3.10 (2H,m), 3.97–4.03(1H,m), 4.47(1H,brd,J=10.9), 6.63–6.72 (1H,m), 6.47(1H,s), 6.58(1H,brs), 6.81(1H,brs), 7.13–7.27 (5H,m), 7.35(1H,brd,J=8.3)

Example 5

Phe-N-Me-Val-[3-(3-methylindol-5-yl)]Ala-NH$_2$ (1) Synthesis of 5-carboethoxy-3-methylindole To a solution of 2-bromo-4-carboethoxy-N-allylaniline (J. Org. Chem., 45, 2710(1980)) (650 mg, 2.29 mmol) in acetonitrile (10 ml), tetrakis(triphenylphosphine)palladium (0) (132 mg, 0.114 mmol), palladium (II) acetate (25.7 mg, 0.114 mmol) and TEA (0.413 ml, 2.98 mmol) were added and stirred overnight in a sealed tube at 100° C. After filtering the reaction mixture, the filtrate was evaporated under reduced pressure; the thus obtained residue was subjected to silica gel column chromatography (developing solvent: ethyl acetate:n-hexane=1:2) to give the titled compound (340 mg, 73%).

NMR (method a, CDCl$_3$): δ 1.43(3H,t,J=7.2 Hz), 2.37 (3H,s), 4.41(2H,q,J=7.2 Hz), 7.03(1H,s), 7.34(1H,d,J=8.6 Hz), 7.91(1H,dd,J=1.3,8.6 Hz), 8.08(1H,brs), 8.36(1H,s)

(2) Synthesis of 5-carboethoxy-3-methyl-1-(2,4,6-trimethylbenzenesulfonyl)indole To a solution of 5-carboethoxy-3-methylindole (601 mg, 2.96 mmol) in DMF, sodium hydride (178 mg, 4.45 mmol) and 2,4,6-trimethylbenzenesulfonyl chloride (971 mg, 4.44 mmol) were added under cooling with ice, followed by stirring for 30 min. The reaction mixture was mixed with a saturated aqueous NH$_4$Cl solution, and extracted with ethyl acetate. The organic layer was washed with water and saturated brine. The organic layer was dried over magnesium sulfate and evaporated under reduced pressure to remove the solvent; the thus obtained residue was subjected to silica gel column chromatography (developing solvent: ethyl acetate:n-hexane=1:5) to give the titled compound (1.02 g, 90%).

NMR (method a, CDCl$_3$): δ 1.40(3H,t,J=7.0Hz), 2.29(3H, s), 2.32(3H,s), 2.52(6H,s), 4.38(2H,q,J=6.9 Hz), 6.95(2H,s), 7.35(1H,s), 7.41(1H,d,J=8.9 Hz), 7.90(1H,dd,J=1.4,8.9 Hz), 8.24(1H,s)

(3) Synthesis of 5-bromomethyl-3-methyl-1-(2,4,6-trimethylbenzenesulfonyl)indole Under cooling with ice, 5-carboethoxy-3-methyl-1-(2,4,6-trimethylbenzenesulfonyl)indole (1.13 g, 2.94 mmol) was added to a solution of lithium aluminum hydride (223 mg, 5.88 mmol) in THF (10 ml), followed by stirring for 1 hour. The reaction mixture was mixed with ethyl acetate and a 2N aqueous HCl solution and extracted with chloroform. The organic layer was washed with water and saturated brine, dried over magnesium sulfate and evaporated to remove the solvent. The thus obtained residue was dissolved in methylene chloride (20 ml) and mixed with triphenylphosphine (1.06 g, 4.04 mmol) and carbon tetrabromide (1.34 g, 4.04 mmol) under cooling with ice, followed by stirring for 1 hour. The reaction mixture was evaporated to remove the solvent; the thus obtained residue was subjected to silica gel column chromatography (developing solvent: ethyl acetate:n-hexane=1:5) to give the titled compound (1.12 g, 94%).

NMR (method a, CDCl$_3$): δ 2.27(3H,s), 2.29(3H,s), 2.54 (6H,s), 4.61(2H,s), 6.96(2H,s), 7.20–7.38(3H,m), 7.52(1H, s)

(4) Synthesis of N-[Bis(methylthio)methylene]-3-[3-methyl-1-(2,4,6-trimethylbenzenesulfonyl)Indol-5-yl]Ala-OEt At −78° C. in a nitrogen atmosphere, a solution of ethyl ester of N-[bis(methylthio)methylene]glycine (Angew. Chem. Internat. Edit., 14, 426(1975)) (743 mg, 3.59 mmol) in THF (6 ml) was added to a solution of potassium t-butoxide (403 mg, 3.59 mmol) in THF (15 ml), followed by stirring for 15 min. The mixture was further mixed with a solution of 5-bromomethyl-3-methyl-1-(2,4,6-trimethylbenzenesulfonyl)indole (1.12 g, 2.76 mmol) in THF (6 ml) and stirred for 3 hours at room temperature. Under cooling with ice, the mixture was mixed with a saturated aqueous NH$_4$Cl solution and extracted with ethyl acetate. The organic layer was washed with water and saturated brine, dried over magnesium sulfate and evaporated under reduced pressure to remove the solvent; the thus obtained residue was subjected to silica gel column chromatography (developing solvent: ethyl acetate:n-hexane= 1:4) to give the titled compound (1.41 g, 96%).

NMR (method a, CDCl$_3$): δ 1.15(3H,t,J=7.2 Hz), 2.24 (3H,s), 2.28(3H,s), 2.39(3H,s), 2.41(3H,s), 2.52(6H,s), 3.17 (1H,d,J=6.3 Hz), 3.26(1H,d,J=6.3 Hz), 4.10(2H,q,J=7.2 Hz), 4.58(1H,t,J=6.3 Hz), 6.94(2H,s), 7.06(2H,d,J=8.6 Hz), 7.20–7.30(2H,m), 7.33(1H,s)

(5) Synthesis of N-Me-Val-[3-[3-methyl-1-(2,4,6-trimethylbenzenesulfonyl)Indol-5-yl]]Ala-NH$_2$ To a solution of N-[bis(methylthio)methylene]-3-[3-methyl-1-(2,4,6-trimethylbenzenesulfonyl)indol-5-yl]Ala-OEt (1.41 g, 2.65 mmol) in 1,4-dioxane (25 ml), 2N hydrochloric acid (15 ml) was added, followed by stirring overnight at room temperature, Under cooling with ice, the mixture was mixed with a saturated aqueous NaHCO$_3$ solution and extracted with chloroform. The organic layer was washed with water and saturated brine, dried over magnesium sulfate and evaporated under reduced pressure to remove the solvent. The thus obtained residue was dissolved in methylene chloride (30 ml) and mixed with Z-N-Me-Val-OH (912 mg, 3.44 mmol), BOP (1.52 g, 3.44 mmol) and DIEA (0.600 ml, 3.44 mmol) under cooling with ice, followed by stirring for 2 hours at room temperature. The reaction mixture was mixed with water and extracted with methylene chloride. The organic layer was washed with water and saturated brine, dried over magnesium sulfate and evaporated under reduced pressure to remove the solvent; the thus obtained residue was subjected to silica gel column chromatography (developing solvent: ethyl acetate:n-hexane=1:2) to give Z-N-Me-Val-[3-[3-methyl-1-(2,4,6-trimethylbenzenesulfonyl)indol-5-yl]]Ala-OEt (1.32 g, 74%).

To a solution of the thus obtained compound (1.32 g, 1.96 mmol) in methanol (20 ml), concentrated aqueous ammonia (10 ml) was added, followed by stirring at room temperature overnight. The reaction mixture was evaporated, extracted with chloroform. The organic layer was washed with water and saturated brine, dried over magnesium sulfate and evaporated under reduced pressure to remove the solvent; the thus obtained residue was subjected to silica gel column chromatography (developing solvent: chloroform:methanol=20:1) to give Z-N-Me-Val-[3-[3-methyl-1-(2,4,6-trimethylbenzenesulfonyl)indol-5-yl]]Ala-NH$_2$ (690 mg, 55%).

To a solution of the thus obtained compound (690 mg, 1.07 mmol) in methanol (10 ml), 10% palladium-carbon (200 mg) was added, followed by stirring in a hydrogen atmosphere at room temperature overnight. After filtering the reaction mixture, the filtrate was concentrated under reduced pressure; the thus obtained residue was subjected to silica gel column chromatography (developing solvent: chloroform:methanol=10:1) to give two diastereoisomers A and B of the titled compound, A (275 mg, 50%) being eluted first and then B (228 mg, 42%).

(A)

NMR (method a, CDCl$_3$): δ 0.56(3H,d,J=6.9 Hz), 0.75 (3H,d,J=6.9 Hz), 1.80–1.96(1H,m), 2.24(3H,s), 2.27(3H,s), 2.29(3H,s), 2.52(6H,s), 2.71(1H,d,J=4.6 Hz), 3.06–3.30(2H, m), 4.58–4.70(1H,m), 5.29(1H,brs), 6.13(1H,brs), 6.94(2H, s), 7.07(1H,d,J=7.9 Hz), 7.29(1H,s), 7.35(1H,s), 7.68(1H,d, J=7.9 Hz)

(B)

NMR (method a, CDCl$_3$): δ 0.82(3H,d,J=6.9 Hz), 0.91 (3H,d,J=6.9 Hz), 1.89(3H,s), 1.90–2.08(1H,m), 2.25(3H,s), 2.27(3H,s), 2.29(3H,s), 2.50(6H,s), 2.63(1H,d,J=4.0 Hz), 3.04–3.32(2H,m), 4.56–4.70(1H,m), 5.26(1H,brs), 6.27(1H, brs), 6.94(2H,s), 7.07(1H,d,J=7.9 Hz), 7.29(1H,s), 7.36(1H, s), 7.62(1H,d,J=7.9 Hz)

(6) Synthesis of Phe-N-Me-Val-[3-(3-methylindol-5-yl)]Ala-NH$_2$ (A)

To a solution of N-Me-Val-[3-[3-methyl-1-(2,4,6-trimethylbenzenesulfonyl)indol-5-yl]]Ala-NH$_2$ (A) (275 mg, 0.537 mmol) in a mixture of methylene chloride (4 ml) and DMF (1 ml), Boc-Phe-OH (214 mg, 0.806 mmol), BOP (356 mg, 0.806 mmol) and DIEA (0.140 ml, 0.804 mmol) were added under cooling with ice, followed by stirring at room temperature overnight. The reaction mixture was mixed with water and extracted with methylene chloride. The organic layer was washed with water and saturated brine, dried over magnesium sulfate and evaporated under reduced pressure to remove the solvent; the thus obtained residue was subjected to silica gel column chromatography (developing solvent: ethyl acetate:n-hexane=1:1) to give Boc-Phe-N-Me-Val-[3-[3-methyl-1-(2,4,6-trimethylbenzenesulfonyl)indol-5-yl]]Ala-NH$_2$ (A) (185 mg, 45%).

To a solution of the thus obtained compound (153 mg, 0.202 mmol) in TFA (0.5 ml), a solution of thioanisole (0.067 ml, 0.571 mmol) in methanesulfonic acid (0.335 ml) was added, followed by stirring at room temperature for 1 hour. Under cooling with ice, the mixture was mixed with saturated aqueous NaHCO$_3$ and extracted with chloroform. The organic layer was washed with water and saturated brine, dried over magnesium sulfate and evaporated under reduced pressure to remove the solvent; the thus obtained residue was subjected to silica gel column chromatography (developing solvent: chloroform:methanol=10:1) to give the titled compound (55.2 mg, 57%).

EI-MS:477(M$^+$) NMR (method a, CDCl$_3$): δ 0.74(2H,d, J=6.6 Hz), 0.80(1H,d,J=6.6 Hz), 0.92(2H,d,J=6.6 Hz), 0.94 (1H,d,J=6.6 Hz), 2.32(1H,s), 2.34(2H,s), 2.40–2.62(1H,m), 2.72(2H,s), 2.78(1H,s), 3.02–3.28(2H,m), 3.50(2/3H,dd,J= 4.3,8.9 Hz), 3.73(1/3H,dd,J=5.3,8.2 Hz), 3.94(2/3H,d,J= 10.9 Hz), 4.52(1/3H,d,J=10.9 Hz), 4.62–4.80(1H,m), 5.23 (1H,brs), 5.68(1/3H,brs), 5.79(2/3H,brs), 6.90–7.60(9H,m), 7.78(1/3H,brs), 7.98(2/3H,brs), 9.06(2/3H,d,J=7.6 Hz)

(7) Synthesis of Phe-N-Me-Val-[3-(3-methylindol-5-yl)]Ala-NH$_2$ (B)

To a solution of N-Me-Val-[3-[3-methyl-1-(2,4,6-trimethylbenzenesulfonyl)indol-5-yl]]Ala-NH$_2$ (B) (220 mg, 0.430 mmol) in DMF (3 ml), Boc-Phe-OH (171 mg, 0.645 mmol), DIC (99.8 ml, 0.645 mmol) and HOBT (98.8 mg, 0.645 mmol) were added under cooling with ice, followed by stirring at room temperature overnight. The reaction mixture was mixed with water and extracted with ethyl acetate. The organic layer was washed with water and saturated brine, dried over magnesium sulfate and evaporated under reduced pressure to remove the solvent; the thus obtained residue was subjected to silica gel column chromatography (developing solvent: ethyl acetate:n-hexane= 1:1) to give a mixture (204 mg) containing Boc-Phe-N-Me-Val-[3-[3-methyl-1-(2,4,6-trimethylbenzenesulfonyl)indol-5-yl]]Ala-NH$_2$ (B).

To a solution of the thus obtained mixture (204 mg) in TFA (1.5 ml), a solution of thioanisole (0.158 ml, 1.35 mmol) in methanesulfonic acid (0.79 ml) was added, followed by stirring at room temperature for 1 hour. Under cooling with ice, the mixture was mixed with saturated aqueous NaHCO$_3$ and extracted with chloroform. The organic layer was washed with water and saturated brine, dried over magnesium sulfate and evaporated under reduced pressure to remove the solvent; the thus obtained residue was subjected to silica gel column chromatography (developing solvent: chloroform:methanol=10:1) to give the titled compound (25.7 mg, 13%).

EI-MS:477(M$^+$)

NMR (method a, CDCl$_3$): δ 0.75(3/2H,d, J=6.6 Hz), 0.80(3/2H,d,J=6.6 Hz), 0.81(3/2H,d,J=6.6 Hz), 0.88(3/2H, d,J=6.6 Hz), 2.24(3/2H,s), 2.31(3/2H,s), 2.48–2.80(1H,m), 2.80(3/2H,s), 2.92(3/2H,s), 2.90–3.30(2H,m), 3.62(1/2H,dd, J=4.6,8.5 Hz), 3.84(1/2H,dd,J=5.3,8.2 Hz), 3.94(1/2H,d,J= 10.9 Hz), 4.37(1/2H,d,J=10.9 Hz), 4.60–4.76(1H,m), 5.17 (1H,brs), 5.56(1/2H,brs), 5.77(1/2H,brs), 6.50(1/2H,d,J=8.8 Hz), 6.92–7.44(9H,m), 7.85(1H,d,J=6.9 Hz), 9.11(1/2H,d, J=7.9 Hz)

Example 6

Phe-N-Me-Val-N-Me-[3-(3-methylindol-5-yl)]Ala-NH$_2$ (1) Synthesis of N-Me-[3-[3-methyl-1-(2,4,6-trimethylbenzenesulfonyl)Indol-5-yl]]Ala-OEt To a solution of N-[bis(methylthio)methylene]-3-[3-methyl-1-(2,4,6-trimethylbenzenesulfonyl)indol-5-yl]Ala-OEt (1.41 g, 2.65 mmol) in 1,4-dioxane (25 ml), 2N hydrochloric acid (15 ml) was added, followed by stirring at room temperature overnight. Under cooling with ice, the mixture was mixed with a saturated aqueous NaHCO$_3$ solution and extracted with chloroform. The organic layer was washed with water and saturated brine, dried over magnesium sulfate and evaporated under reduced pressure to remove the solvent. The thus obtained residue was dissolved in methylene chloride (20 ml) and under cooling with ice, mixed with TEA (0.407 ml, 2.93 mmol) and benzyl chloroformate (0.418 ml, 2.93 mmol), followed by stirring for 1 hour. The reaction mixture was mixed with a saturated aqueous NaHCO$_3$ solution, extracted with methylene chloride. The organic layer was washed with water and saturated brine, dried over magnesium sulfate and evaporated to remove the solvent under reduced pressure; the thus obtained residue was subjected to silica gel column chromatography (developing solvent: ethyl acetate:n-hexane=1:4) to give Z-[3-[3-methyl-1-(2,4,6-trimethylbenzenesulfonyl)indol-5-yl]]Ala-OEt (880 mg, 64%).

Under cooling with ice, 60% sodium hydride (80.8 mg, 2.02 mmol) and methyl iodide (0.125 ml, 2.02 mmol) were added to a solution of Z-[3-[3-methyl-1-(2,4,6-trimethylbenzenesulfonyl)indol-5-yl]]Ala-OEt (870 mg, 1.55 mmol) in DMF (15 ml), followed by stirring for 30 min. The reaction mixture was mixed with a saturated aqueous NH$_4$Cl solution and extracted with ethyl acetate. The organic layer was washed with water and saturated brine, dried over magnesium sulfate and evaporated to remove the solvent under reduced pressure; the thus obtained residue was subjected to silica gel column chromatography (developing solvent: ethyl acetate:n-hexane=1:4) to give Z-N-Me-[3-[3-methyl-1-(2,4,6-trimethylbenzenesulfonyl)indol-5-yl]]Ala-OEt (771 mg, 86%).

To a solution of the thus obtained compound (770 mg, 1.34 mmol) in methanol (10 ml), 10% palladium carbon (150 mg) was added, followed by stirring in a hydrogen atmosphere overnight at room temperature. The mixture was filtered and the filtrate was evaporated under reduced pressure to remove the solvent, giving the titled compound (592 mg, 100%).

NMR (method a, CDCl$_3$): δ 1.12(3H,t,J=7.2 Hz), 2.24 (3H,s), 2.29(3H,s), 2.35(3H,s), 2.53(6H,s), 3.00(1H,d,J=6.9

Hz), 3.43(1H,t,J=6.9 Hz), 4.10(2H,q,J=7.2 Hz), 6.94(2H,s), 7.01(2H,d,J=8.6 Hz), 7.22–7.32(3H,m)

(2) Synthesis of Z-Phe-N-Me-Val-N-Me-[3-[3-methyl-1-(2,4,6-trimethylbenzenesulfonyl)Indol-5-yl]]Ala-NH$_2$ To a solution of N-Me-[3-[3-methyl-1-(2,4,6-trimethylbenzenesulfonyl)indol-5-yl]]Ala-OEt (0.34 g, 0.77 mmol) in methylene chloride (12 ml), Z-Phe-N-Me-Val-OH (0.48 g, 1.16 mmol), PyClU (0.37 g, 1.16 mmol) and DIEA (0.40 ml, 2.31 mmol) were added under cooling with ice, followed by stirring overnight at room temperature. The reaction mixture was mixed with water and extracted with methylene chloride. The organic layer was washed with water and saturated brine, dried over magnesium sulfate and evaporated under reduced pressure to remove the solvent; the thus obtained residue was subjected to silica gel column chromatography (developing solvent: ethyl acetate:n-hexane=1:2) to give Z-Phe-N-Me-Val-N-Me-[3-[3-methyl-1-(2,4,6-trimethylbenzenesulfonyl)indol-5-yl]]Ala-OEt (491 mg, 76%).

To a solution of the thus obtained compound (568 mg, 0.679 mmol) in 1,4-dioxane (5 ml), a 2N aqueous NaOH solution (1 ml) was added, followed by stirring for 3 hours at 50° C. Under cooling with ice, the mixture was rendered acidic by the addition of a 2N hydrochloric acid solution, extracted with chloroform. The organic layer was washed with water and saturated brine, dried over magnesium sulfate and evaporated under reduced pressure to remove the solvent. The thus obtained residue was dissolved in THF (7 ml) and under cooling with ice, mixed with NMM (0.097 ml, 0.88 mmol) and ethyl chloroformate (0.084 ml, 0.88 mmol), followed by stirring for 30 min. The reaction mixture was stirred for further 30 min. while bubbling gaseous ammonia therein and then left standing at room temperature. Then the reaction mixture was diluted with chloroform and washed with water and saturated brine. The organic layer was dried over magnesium sulfate and evaporated under reduced pressure to remove the solvent; the thus obtained residue was subjected to silica gel column chromatography (developing solvent: ethyl acetate:n-hexane=1:1) to give four diastereoisomers A, B, C and D of the titled compound, a mixture AB (236 mg, 43%) being eluted first and then a mixture CD (260 mg, 47%).

(3) Synthesis of Phe-N-Me-Val-N-Me-[3-[3-methyl-1-(2,4,6-trimethylbenzenesulfonyl)Indol-5-yl]]Ala-NH$_2$ (A) and (B)

To a solution of Z-Phe-N-Me-Val-N-Me-[3-[3-methyl-1-(2,4,6-trimethylbenzenesulfonyl)indol-5-yl]]Ala-NH$_2$ (AB) (230 mg, 0.285 mmol) in methanol (3 ml), 10% palladium-carbon (100 mg) was added, followed by stirring at room temperature overnight in a hydrogen atmosphere. The reaction mixture was filtered and the filtrate was concentrated under reduced pressure. The thus obtained residue was subjected to preparative thin-layer chromatography (developing solvent: chloroform:methanol=10:1) to give two diastereoisomers A and B of Phe-N-Me-Val-N-Me-[3-[3-methyl-1-(2,4,6-trimethylbenzenesulfonyl)indol-5-yl]]Ala-NH$_2$, A (78.7 mg, 41%) being eluted first and then B (82.2 mg, 43%).

(4) Synthesis of Phe-N-Me-Val-N-Me-[3-(3-methylindol-5-yl) ]Ala-NH$_2$ (A)

Under cooling with ice, a solution of thioanisole (0.05 ml) in methanesulfonic acid (0.2 ml) was added to a solution of Phe-N-Me-Val-N-Me-[3-[3-methyl-1-(2,4,6-trimethylbenzenesulfonyl)indol-5-yl]]Ala-NH$_2$ (A) (78.2 mg, 0.116 mmol) in TFA (0.5 ml), followed by stirring for 1 hour. Under cooling with ice, the mixture was mixed with saturated aqueous NaHCO$_3$ and extracted with chloroform. The organic layer was washed with water and saturated brine, dried over magnesium sulfate and evaporated under reduced pressure to remove the solvent; the thus obtained residue was subjected to preparative thin-layer chromatography (developing solvent: chloroform:methanol=10:1) to give the titled compound (34.5 mg, 61%).

EI-MS:491(M$^+$) NMR (method a, CDCl$_3$): δ 0.35(3H,d, J=6.6 Hz), 0.75(3H,d,J=6.6 Hz), 2.04–2.18(1H,m), 2.28(3H, s), 2.62(1H,dd,J=7.3,13.5 Hz), 2.90–3.12(2H,m), 2.94(3H, s), 3.03(3H,s), 3.48(1H,dd,J=6.3,13.5 Hz), 3.90(1H,dd,J= 6.3,7.3 Hz), 4.82(1H,d,J=10.7 Hz), 5.12(1H,brs), 5.51(1H, dd,J=6.0,10.2 Hz), 6.09(1H,brs), 6.92(1H,s), 7.03(1H,d,J= 8.2 Hz), 7.14–7.38(6H,m), 7.79(1H,s)

(5) Synthesis of Phe-N-Me-Val-N-Me-[3-(3-methylindol-5-yl)]Ala-NH$_2$ (B)

To a solution of Phe-N-Me-Val-N-Me-[3-[3-methyl-1-(2,4,6-trimethylbenzenesulfonyl)indol-5-yl]]Ala-NH$_2$ (B) (81.6 mg, 0.121 mmol) in TFA (0.5 ml), thioanisole (0.05 ml) in methanesulfonic acid (0.2 ml) was added under cooling with ice, followed by stirring for 1 hour. The mixture was mixed with saturated aqueous NaHCO$_3$ under cooling with ice and extracted with chloroform. The organic layer was washed with water and saturated brine, dried over magnesium sulfate and evaporated under reduced pressure to remove the solvent; the thus obtained residue was subjected to preparative thin-layer chromatography (developing solvent: chloroform:methanol=10:1) to give the titled compound (35.6 mg, 60%).

EI-MS:491(M$^+$) NMR (method a, CDCl$_3$): δ 0.28(3H,d, J=6.8 Hz), 0.56(3H,d,J=6.6 Hz), 1.96–2.08(1H,m), 2.28(3H, s), 2.64–2.74(1H,m), 2.92–3.24(2H,m), 2.95(3H,s), 3.13 (3H,s), 3.55(1H,dd,J=6.2,14.5 Hz), 3.92(1H,dd,J=6.2,6.6 Hz), 4.76(1H,d,J=10.9 Hz), 5.23(1H,brs), 5.53(1H,dd,J=6.0, 10.2 Hz), 6.25(1H,brs), 6.93(1H,s), 7.04(1H,d,J=8.5 Hz), 7.14–7.40(6H,m), 7.81(1H,s)

(6) Synthesis of Phe-N-Me-Val-N-Me-[3-[3-methyl-1-(2,4,6-trimethylbenzenesulfonyl)Indol-5-yl]]Ala-NH$_2$ (C) and (D)

To a solution of Z-Phe-N-Me-Val-N-Me-[3-[3-methyl-1-(2,4,6-trimethylbenzenesulfonyl)indol-5-yl]]Ala-NH$_2$ (CD) (251 mg, 0.311 mmol) in methanol (3 ml), 10% palladium-carbon (100 mg) was added, followed by stirring at room temperature overnight in a hydrogen atmosphere. The reaction mixture was filtered and the filtrate was concentrated under reduced pressure. The thus obtained residue was subjected to preparative thin-layer chromatography (developing solvent:chloroform:methanol=10:1) to give two diastereoisomers C and D of Phe-N-Me-Val-N-Me-[3-[3-methyl-1-(2,4,6-trimethylbenzenesulfonyl)indol-5-yl]]Ala-NH$_2$, C (91.6 mg, 44%) being eluted first and then D (69.1 mg, 33%).

(7) Synthesis of Phe-N-Me-Val-N-Me-[3-(3-methylindol-5-yl)]Ala-NH$_2$ (C)

Under cooling with ice, a solution of thioanisole (0.05 ml) in methanesulfonic acid (0.2 ml) was added to a solution of Phe-N-Me-Val-N-Me-[3-[3-methyl-1-(2,4,6-trimethylbenzenesulfonyl)indol-5-yl]]Ala-NH$_2$ (C) (78.2 mg, 0.116 mmol) in TFA (0.5 ml), followed by stirring for 1 hour. Under cooling with ice, the mixture was mixed with saturated aqueous NaHCO$_3$ and extracted with chloroform. The organic layer was washed with water and saturated brine, dried over magnesium sulfate and evaporated under reduced pressure to remove the solvent; the thus obtained residue was subjected to preparative thin-layer chromatography (developing solvent:chloroform:methanol=10:1) to give the titled compound (35.1 mg, 53%).

EI-MS:491(M$^+$) NMR (method a, CDCl$_3$): δ 0.38(3/5H, d,J=6.6 Hz), 0.72–0.80(3H,m), 0.94(12/5H,d,J=6.3 Hz), 2.08–2.14(2H,m), 2.18(12/5H,s), 2.28(3/5H,s), 2.39(12/5H, s), 2.56–3.18(2H,m), 2.84(12/5H,s), 3.02(3/5H,s), 3.06(3/5H,s), 3.30–3.42(4/5H,m), 3.50–3.58(1H,m), 3.86–3.92(1/5H,m), 4.99(1/5H,d,J=10.6 Hz), 5.07(4/5H,d,J=10.5 Hz), 5.25(4/5H,brs), 5.64(4/5H,dd,J=6.0,10.8 Hz) 6.04(4/5H, brs), 6.74(1H,s), 6.92–7.52(8H,m)

(8) Synthesis of Phe-N-Me-Val-N-Me-[3-(3-methylindol-5-yl)]Ala-NH$_2$ (D)

Under cooling with ice, thioanisole (0.05 ml) in methanesulfonic acid (0.2 ml) was added to a solution of Phe-N-Me-Val-N-Me-[3-[3-methyl-1-(2,4,6-trimethylbenzenesulfonyl)indol-5-yl]]Ala-NH$_2$ (D) (68.6 mg, 0.102 mmol) in TFA (0.5 ml), followed by stirring for 1 hour. Under cooling with ice, the mixture was mixed with saturated aqueous NaHCO$_3$ and extracted with chloroform. The organic layer was washed with water and saturated brine, dried over magnesium sulfate and evaporated under reduced pressure to remove the solvent; the thus obtained residue was subjected to preparative thin-layer chromatography (developing solvent:chloroform:methanol=10:1) to give the titled compound (38.7 mg, 77%).

EI-MS:491(M$^+$) NMR (method a, CDCl$_3$): δ 0.08(1H,d, J=6.6 Hz), 0.44(1H,d,J=6.6 Hz), 0.53(2H,d,J=6.6 Hz), 0.87 (2H,d,J=6.6 Hz), 2.02–2.26(4/3H,m), 2.21(2H,s), 2.26(2H, s), 2.33(1H,s), 2.47(2/3H,dd,J=8.2,13.8 Hz), 2.64–2.82(1H, m), 2.91(1H,s), 2.97(2H,s), 2.94–3.22(7/3H,m), 3.36(2/3H, dd,J=5.6,15.2 Hz) 3.90–3.98(1/3H,m), 4.78(1/3H,d,J=10.6 Hz), 5.00–5.08(1H,m), 5.20–5.32(1H,m), 5.58(2/3H,dd,J=5.6,11.2 Hz), 6.02(2/3H,brs), 6.94–7.48(9H,m), 7.84(1/3H, brs), 8.04(2/3H,brs)

Example 7

Phe-N-Me-Val-Phe(3-tBu-4-F)-NH$_2$ (1) 3-tert-butyl-4-fluorotoluene

To a solution of aluminum chloride (8.1 g, 60.7 mmol) in carbon disulfide (60 ml), 4-fluorotoluene (6.0 g, 54.5 mmol) was added and then under cooling with ice, tert-butyl chloride (6.0 ml, 54.5 mmol) was added, followed by stirring for 10 min. The reaction mixture was poured into ice water and extracted with methylene chloride. The organic layer was washed with saturated brine, dried over sodium sulfate and evaporated under reduced pressure to remove the solvent. The thus obtained residue was subjected to silica gel column chromatography (developing solvent: n-hexane) to give the titled compound (5.92 g, 63%).

NMR (method a, CDCl$_3$): δ 1.36(9H,s), 2.30(3H,s), 6.87 (1H,dd,J=12.2,8.3 Hz), 6.93–7.08(2H,m)

(2) Synthesis of 3-tert-butyl-4-fluorobenzyl bromide

To a solution of 3-tert-butyl-4-fluorotoluene (5.92 g, 34.4 mmol) in carbon tetrachloride (60 ml), N-bromosuccinimide (6.1 g, 34.4 mmol) and benzoyl peroxide (containing 25% of water) (1.1 g, 3.44 mmol) were added, followed by stirring for 30 min. while heating under reflux. The mixture was evaporated to remove the solvent; the thus obtained residue was mixed with n-hexane and filtered to remove the insoluble matter. The filtrate was evaporated to remove the solvent; the thus obtained residue was subjected to silica gel column chromatography (developing solvent: n-hexane) to give the titled compound (7.01 g, 83%).

NMR (method a, CDCl$_3$): δ 1.38(9H,s), 4.48(2H,s), 6.96 (1H,dd,J=12.2,8.3 Hz), 7.17–7.24(1H,m), 7.30(1H,dd,J=7.6, 2.3 Hz)

(3) Synthesis of 3-tert-butyl-4-fluorobenzyl Iodide

To a solution of 3-tert-butyl-4-fluorobenzyl bromide (1.49 g, 6.08 mmol) in acetone (50 ml), sodium iodide (9.1 g, 60.8 mmol) was added, followed by stirring at room temperature overnight. The reaction mixture was mixed with water and extracted with n-hexane. The organic layer was washed with an aqueous sodium thiosulfate solution and saturated brine, dried over sodium sulfate and evaporated under reduced pressure to remove the solvent. The thus obtained residue was subjected to silica gel column chromatography (developing solvent: n-hexane) to give the titled compound (1.18 g, 66%).

NMR (method a, CDCl$_3$): δ 1.37(9H,s), 4.44(2H,s), 6.91 (1H,dd,J=12.2,8.3 Hz), 7.16–7.23(1H,m), 7.29(1H,dd,J=7.9, 2.3 Hz)

(4) Synthesis of Ethyl Ester of N-[Bis(methylthio) methylene]-3-(3-tert-butyl-4-fluorophenyl)Alanine Potassium tert-butoxide (544 mg, 4.40 mmol) was dissolved in THF (10 ml) and cooled to −78° C. in a nitrogen atmosphere. To this solution, a solution of ethyl ester of N-[bis(methylthio)methylene]glycine (840 mg, 4.04 mmol) in THF (10 ml) was added dropwise, stirred at −78° C. for 45 min. and then a solution of 3-tert-butyl-4-fluorobenzyl iodide (1.18 g, 4.85 mmol) in THF (15 ml) was added dropwise, followed by stirring at −78° C. for 2 hours. The reaction mixture was mixed with water and extracted with ethyl acetate. The organic layer was washed with saturated brine, dried over sodium sulfate and evaporated under reduced pressure to remove the solvent. The thus obtained residue was subjected to silica gel column chromatography (developing solvent: n-hexane:ethyl acetate=10:1) to give the titled compound (1.18 g, 79%).

NMR (method a, CDCl$_3$): δ 1.22(3H,t,J=6.9 Hz), 1.35 (9H,s), 2.40(3H,s), 2.44(3H,s), 3.04–3.22(2H,m), 4.15(2H, q,J=6.9 Hz), 4.55–4.60(1H,m), 6.87(1H,dd,J=12.1,8.3 Hz), 6.97–7.04(1H,m), 7.09(1H,dd,J=8.3,2.0 Hz)

(5) Synthesis of D,L-Phe(3-tBu-4-F)-OEt

To a solution of ethyl ester of N-[bis(methylthio) methylene]-3-(3-tert-butyl-4-fluorophenyl)alanine (1.08 g, 2.91 mmol) in dioxane (25 ml), 2N hydrochloric acid (12 ml) was added, followed by stirring for 1 day at room temperature. The reaction mixture was mixed with a 2N aqueous sodium hydroxide solution and extracted with ethyl acetate. The organic layer was washed with saturated brine, dried over sodium sulfate and evaporated under reduced pressure to remove the solvent. The thus obtained residue was subjected to silica gel column chromatography (developing solvent: n-hexane:ethyl acetate=5:1) to give the titled compound (740 mg, 85%).

NMR (method a, CDCl$_3$): δ 1.24(3H,t,J=6.9 Hz), 1.36 (9H,s), 2.81–3.06(2H,m), 3.66–3.71(1H,m), 4.16(2H,q,J= 6.9 Hz), 6.92(1H,dd,J=12.2,8.3 Hz), 6.97–7.03(1H,m), 7.09 (1H,dd,J=7.9,2.0 Hz)

(6) Synthesis of Z-N-Me-Val-Phe(3-tBu-4-F)-OEt

To a solution of Z-N-Me-Val-OH (790 mg, 2.97 mmol) in DMF (25 ml), D,L-Phe(3-tBu-4-F)-OEt (740 mg, 2.47 mmol) and HOBT (454 mg, 2.97 mmol) were added under cooling with ice. To the mixture, DIC (0.46 ml, 2.97 mmol) was added dropwise, followed by stirring under cooling with ice for 13.5 hours. The reaction mixture was mixed with water and extracted with ethyl acetate. The organic layer was washed with saturated brine, dried over sodium sulfate and evaporated under reduced pressure to remove the solvent. The thus obtained residue was subjected to silica gel column chromatography (developing solvent: methanol:methylene chloride=3:100) to give the titled compound (1.49 g, quant.).

NMR (method a, CDCl$_3$): δ 0.84(4.5H,d,J=6.6 Hz), 0.90 (1.5H,d,J=6.6 Hz), 1.17–1.29(3H,m), 1.34(5.5H,s), 1.35 (3.5H,s), 2.15–2.33(1H,m), 2.77(1.5H,s), 2.84(1.5H,s), 2.84–3.15(2H,m), 4.02–4.20(3H,m), 4.71–4.84(1H,m), 5.13 (2H,s), 6.40–6.60(1H,m), 6.67–7.07(3H,m), 7.17–7.44(5H, m)

(7) Synthesis of Z-N-Me-Val-Phe(3-tBu-4-F)-OH

To a solution of Z-N-Me-Val-Phe(3-tBu-4-F)-OEt (1.44 g, 2.64 mmol) in dioxane (25 ml), a 2N aqueous sodium hydroxide solution (25 ml) was added, followed by stirring at room temperature overnight. The reaction mixture was mixed with 2N hydrochloric acid and extracted with chloroform. The organic layer was washed with saturated brine, dried over sodium sulfate and evaporated under reduced pressure to remove the solvent. The thus obtained residue was subjected to silica gel column chromatography (developing solvent:methanol:acetic acid:methylene chloride=3:0.1:100) to give the titled compound (1.17 g, 86%).

NMR (method a, CDCl$_3$): δ 0.76–0.89(6H,m), 1.33(6H, s), 1.35(3H,s), 2.13–2.29(1H,m), 2.74(1.5H,s), 2.87(1H,s), 2.80–3.24(2H,m), 4.09(1H,d,J=10.9 Hz), 4.73–4.85(1H,m), 5.04–5.24(2H,m), 6.69–7.13(3H,m), 7.04–7.40(5H,m)

(8) Synthesis of N-Me-Val-Phe(3-tBu-4-F)-NH$_2$

A solution of Z-N-Me-Val-Phe(3-tBu-4-F)-OH (1.17 g, 2.26 mmol) and NMM (0.25 ml, 2.26 mmol) in DMF (22 ml) was cooled to −15° C. and ethyl chloroformate (0.22 ml, 2.26 mmol) was added dropwise, followed by stirring for 5 min. Into the mixture, gaseous ammonia was blown at −15° C., followed by stirring for 1 hour. The mixture was warmed to room temperature, mixed with water and extracted with ethyl acetate. The organic layer was washed with saturated brine, dried over sodium sulfate and evaporated under reduced pressure to remove the solvent, giving a crude product of Z-N-Me-Val-Phe(3-tBu-4-F)-NH$_2$ (1.25 g).

NMR (method a, CDCl$_3$): δ 0.66(2H,d,J=6.6 Hz), 0.85 (4H,d,J=5.9 Hz), 1.35(9H,s),2.07–2.29(1H,m), 2.74(1H,s), 2.93(2H,s), 2.80–3.04(2H,m), 3.84(0.2H,d,J=11.2 Hz), 3.98 (0.8H,d,J=10.9 Hz), 4.51–4.75(1H,m), 5.04–5.20(2H,m), 6.80–7.16(3H,m), 7.27–7.42(5H,m)

A solution of the thus obtained crude product (1.25 g) and 10% palladium-carbon (380 mg) in methanol (70 ml) was stirred for 16 hours in a hydrogen atmosphere. After removing the catalyst by filtration, the filtrate was evaporated under reduced pressure to remove the solvent. The thus obtained residue was subjected to silica gel column chromatography (developing solvent: methanol:aqueous ammonia:methylene chloride=3:0.1:100) to give the diastereoisomers A and B of the titled compound, A (370 mg, 47%, in 2 steps) being eluted first and then B (360 mg, 45%, in 2 steps).

(A)

NMR (method a, CDCl$_3$): δ 0.63(3H,d,J=6.9 Hz), 0.80 (3H,d,J=6.9 Hz), 1.35(9H,s), 1.84–2.20(1H,m), 2.30(3H,s), 2.73(1H,d,J=4.3 Hz), 2.96–3.19(2H,m), 4.59–4.67(1H,m), 6.90(1H,dd,J=12.2,8.3 Hz), 7.01–7.07(1H,m), 7.13(1H,dd, J=7.9,2.0 Hz)

(B)

NMR (method a, CDCl$_3$): δ 0.84(3H,d,J=6.9 Hz), 0.94 (3H,d,J=6.9 Hz), 1.35(9H,s), 1.98–2.13(1H,m), 2.05(3H,s), 2.68(1H,d,J=4.3 Hz), 2.95–3.24(2H,m), 4.61–4.70(1H,m), 6.91(1H,dd,J=12.2,8.3 Hz), 7.02–7.08(1H,m), 7.14(1H,dd, J=7.9,2.0 Hz)

(9) Synthesis of Phe- N-Me-Val-Phe(3-tBu-4-F)-NH$_2$ (A)

N-Me-Val-Phe(3-tBu-4-F)-NH$_2$ (A) (370 mg, 1.05 mmol) was dissolved in methylene chloride (30 ml), cooled with ice and then mixed with Boc-Phe-OH (420 mg, 1.58 mmol), BOP (700 mg, 1.58 mmol) and DIEA (0.28 ml, 1.58 mmol). The mixture was stirred for 22 hours while gradually being warmed from cooling with ice to room temperature. The reaction mixture was mixed with water and extracted with chloroform. The organic layer was washed with saturated brine, dried over sodium sulfate and evaporated under reduced pressure to remove the solvent. The thus obtained residue was subjected to silica gel column chromatography (developing solvent: methanol:methylene chloride=3:100) to give Boc-Phe-N-Me-Val-Phe(3-tBu-4-F)-NH$_2$ (A) (690 mg).

NMR (method a, CDCl$_3$): δ 0.77(1.7H,d,J=6.3 Hz), 0.78 (1.7H,d,J=6.6 Hz), 0.87(1.7H,d,J=6.3 Hz), 1.02(0.9H,d,J= 6.3 Hz), 1.34(7H,s), 1.36(2H,s), 1.38(6H,s), 1.41(3H,s), 2.16–2.40(1H,m), 2.34(0.7H,s), 2.76(2.3H,s), 2.70–3.30 (4H,m), 4.18(0.2H,d,J=9.9 Hz), 4.45(0.8H,d,J=10.9 Hz), 4.50–4.58(0.5H,m), 4.72–4.81(0.5H,m), 5.20–5.50(2H,m), 6.88–7.35(8H,m)

A mixture of the thus obtained compound (690 mg) and TFA (10 ml) was stirred for 5 hours at room temperature. The reaction mixture was evaporated to remove TFA under reduced pressure. The thus obtained residue was mixed with water and a saturated aqueous sodium bicarbonate solution and extracted with chloroform. The organic layer was washed with saturated brine, dried over sodium sulfate and evaporated under reduced pressure to remove the solvent. The thus obtained residue was subjected to silica gel column chromatography (developing solvent: methanol:methylene chloride=3:100) to give the titled compound (300 mg, 57%, in 2 steps).

EI-MS:498(M$^+$) NMR (method a, CDCl$_3$): δ 0.73(1.9H, d,J=6.6 Hz), 0.80(1.1H,d,J=6.6 Hz), 0.89(1.1H,d,J=6.6 Hz), 0.93(1.9H,d,J=6.3 Hz), 1.34(3.3H,s), 1.36(5.7H,s), 2.24–2.37(1H,m), 2.65(1.9H,s), 2.82(1.1H,s), 2.52–3.23(4H, m), 3.65–3.80(0.6H,m), 3.82–3.85(0.4H,m), 3.94(0.7H,d,J= 10.9 Hz), 4.40(0.3H,d,J=10.9 Hz), 4.54–4.71(1H,m), 6.86–7.34(8H,m)

(10) Synthesis of Phe-N-Me-Val-Phe(3-tBu-4-F)-NH$_2$ (B)

N-Me-Val-Phe(3-tBu-4-F)-NH$_2$ (B) (360 mg, 1.03 mmol) was dissolved in methylene chloride (30 ml), cooled with ice and mixed with Boc-Phe-OH (410 mg, 1.54 mmol), BOP (680 mg, 1.54 mmol) and DIEA (0.27 ml, 1.54 mmol). The mixture was stirred for 14.5 hours while being gradually warmed from cooling with ice to room temperature. The reaction mixture was mixed with water and extracted with chloroform. The organic layer was washed with saturated brine, dried over sodium sulfate and evaporated under reduced pressure to remove the solvent. The thus obtained residue was subjected to silica gel column chromatography (developing solvent:methanol:methylene chloride=3:100) to give Boc-Phe-N-Me-Val-Phe(3-tBu-4-F)—NH$_2$ (B) (690 mg).

NMR (method a, CDCl$_3$): δ 0.56(1.0H,d,J=6.3 Hz), 0.65 (1.3H,d,J=7.3 Hz), 0.68(1.7H,d,J=7.3 Hz) 0.78(2.0H,d,J= 6.3 Hz), 1.33(3H,s), 1.36(6H,s), 1.38(5H,s), 1.41(4H,s), 2.10–2.35(1H,m), 2.83(1.5H,s), 2.86(1.5H,s), 2.78–3.38 (4H,m), 3.99(0.3H,d,J=10.9 Hz), 4.28(0.7H,d,J=10.9 Hz), 4.56–4.65(1H,m), 4.75–4.90(1H,m), 6.87–7.40(8H,m)

A mixture of the thus obtained compound (690 mg) and TFA (10 ml) was stirred for 5 hours at room temperature. The reaction mixture was evaporated to remove TFA under reduced pressure. The thus obtained residue was mixed with water and a saturated aqueous sodium bicarbonate solution and extracted with chloroform. The organic layer was washed with saturated brine, dried over sodium sulfate and evaporated under reduced pressure to remove the solvent. The thus obtained residue was subjected to silica gel column chromatography (developing solvent: methanol:methylene chloride=3:100) to give the titled compound (210 mg, 41%, in 2 steps).

EI-MS:498(M$^+$)

NMR (method a, CDCl$_3$): δ 0.68(1.5H,d,J=6.3 Hz), 0.75 (1.7H,d,J=6.6 Hz), 0.82(2.8H,d,J=6.3 Hz), 1.30(4.5H,s), 1.36(4.5H,s), 2.10–2.40(1H,m), 2.78(1.5H,s), 2.94(1.5H,s), 2.54–3.24(4H,m), 3.64–3.91(1H,m), 3.89(0.5H,d,J=10.2 Hz), 4.32(0.5H,d,J=10.2 Hz), 4.61–4.71(1H,m), 6.81–7.36 (8H,m)

Example 8
Phe-N-Me-Val-N-Me-Phe(3-tBu-4-F)-NH$_2$ (1) Synthesis of Z-D,L-Phe(3-tBu-4-F)-OEt To a solution of D,L-Phe(3-tBu-4-F)-OEt (380 mg, 1.27 mmol) in dioxane (4 ml), an aqueous sodium carbonate (150 mg, 1.40 mmol) solution (3 ml) was added and then benzyl chloroformate (0.20 mg, 1.40 mmol) was added dropwise under cooling with ice, followed by stirring for 3 hours under cooling with ice. The reaction mixture was mixed with water and extracted with chloroform. The organic layer was washed with saturated brine, dried over sodium sulfate and evaporated under reduced pressure to remove the solvent. The thus obtained residue was subjected to silica gel column chromatography (developing solvent: n-hexane:methylene chloride=2:3) to give the titled compound (610 mg, quant.).

NMR (method a, CDCl$_3$): δ 1.23(3H,t,J=6.9 Hz), 1.33 (9H,s), 3.07(2H,d,J=5.6 Hz), 4.11–4.17(2H,m), 4.55–4.67 (1H,m), 5.11(2H,s),6.87–7.02(3H,m), 7.30–7.45(5H,m)

(2) Synthesis of Z-N-Me-D,L-Phe(3-tBu-4-F)-OEt

To a solution of Z-D,L-Phe(3-tBu-4-F)-OEt (610 mg, 1.41 mmol) in DMF (14 ml), sodium hydride (60%, 68 mg, 1.69 mmol) and methyl iodide (0.13 ml, 2.12 mmol) were added under cooling with ice, followed by stirring for 3 hours under cooling with ice. The reaction mixture was mixed with water and extracted with ethyl acetate. The organic layer was washed with saturated brine, dried over sodium sulfate and evaporated under reduced pressure to remove the solvent. The thus obtained residue was subjected to silica gel column chromatography (developing solvent: hexane:methylene chloride=1:2) to give the titled compound (520 mg, 83%).

NMR (method a, CDCl$_3$): δ 1.19–1.27(3H,m), 1.33(9H, s), 2.80(1.7H,s), 2.84(1.3H,s), 2.90–3.35(2H,m), 4.10–4.20 (2H,m), 4.55–5.30(1H,m), 5.09(2H,s), 6.80–7.40(8H,m)

(3) Synthesis of N-Me-D,L-Phe(3-tBu-4-F)-NH$_2$

To a solution of Z-N-Me-D,L-Phe(3-tBu-4-F)-OEt (520 mg, 1.16 mmol) in dioxane (12 ml), a 2N aqueous sodium hydroxide solution (12 ml) was added, followed by stirring for 2 hours. The reaction mixture was mixed with 2N hydrochloric acid and extracted with chloroform. The organic layer was washed with saturated brine, dried over sodium sulfate and evaporated under reduced pressure to remove the solvent, giving a crude product of Z-N-Me-D, L-Phe(3-tBu-4-F)-OH (480 mg, 99%).

A solution of the thus obtained crude product (480 mg, 1.15 mmol) and NMM (0.13 ml, 1.15 mmol) in DMF (3 ml) was cooled to −15° C. To the solution, ethyl chloroformate (0.11 ml, 1.15 mmol) was added dropwise and stirred for 10 min. Gaseous ammonia was blown into the resulting mixture at −15° C., followed by stirring for 30 min. The mixture was warmed to room temperature, mixed with water and extracted with ethyl acetate. The organic layer was washed with saturated brine, dried over sodium sulfate and evaporated under reduced pressure to remove the solvent. The thus obtained residue was subjected to silica gel column chromatography (developing solvent: methanol:methylene chloride=2:100) to give Z-N-Me-D,L-Phe(3-tBu-4-F)-NH$_2$ (320 mg, 67%).

NMR (method a, CDCl$_3$): δ 1.34(9H,s), 2.85(3H,s), 2.80–3.40(3H,m), 5.10(2H,s), 6.80–7.40(8H,m)

A solution of the thus obtained compound (320 mg) and 10% palladium-carbon (150 mg) in methanol (15 ml) was stirred for 13 hours in a hydrogen atmosphere. After removing the catalyst by filtration, the filtrate was evaporated under reduced pressure to remove the solvent. The thus obtained residue was subjected to silica gel column chromatography (developing solvent: methanol:aqueous ammonia:methylene chloride=2:0.1:100) to give the titled compound (150 mg, 69%).

NMR (method a, CDCl$_3$): δ 1.37(9H,s), 2.32(3H,s), 2.60–2.80(1H,m), 3.10–3.30(2H,m), 6.90–7.30(8H,m)

(4) Synthesis of Z-Phe-N-Me-Val-N-Me-Phe(3-tBu-4-F)-NH$_2$

To a solution of Z-Phe-N-Me-Val-OH (240 mg, 0.581 mmol) in methylene chloride (10 ml), N-Me-D,L-Phe(3-tBu-4-F)-NH$_2$(110 mg, 0.387 mmol) and BOP (257 mg, 0.581 mmol) and DIEA (0.10 ml, 0.581 mmol) were added under cooling with ice, followed by stirring for 23 hours while the mixture was warmed gradually from cooling with ice to room temperature. The reaction mixture was mixed with methylene chloride, washed with 2N hydrochloric acid, dried over sodium sulfate and evaporated under reduced pressure to remove the solvent. The thus obtained residue was subjected to silica gel column chromatography (developing solvent: ethyl acetate:n-hexane=1:2) to give four diastereoisomers A, B, C and D of the titled compound, a mixture AB being eluted first (80 mg, 32%) and then a mixture CD (61 mg, 24%).

(AB)

NMR (method a, CDCl$_3$): δ 0.20(1.1H,d,J=6.3 Hz), 0.32 (2H,d,J=6.3 Hz), 0.50(0.9H,d,J=6.9 Hz), 0.73(2H,d,J=6.6 Hz), 1.33(9H,s), 1.90–2.20(1H,m), 2.94(3H,s), 2.70–3.60 (4H,m), 4.60–5.70(3H,m), 5.07(2H,s), 6.80–7.40(8H,m)

(CD)

NMR (method a, CDCl$_3$):δ 0.20–0.90(6H,m), 1.20–1.40 (9H,s), 2.10–2.35(1H,m), 2.50–3.50(7H,m), 4.50–5.50(5H, m), 6.70–7.40(8H,m)

(5) Synthesis of Phe-N-Me-Val-N-Me-Phe(3-tBu-4-F)-NH$_2$ (A) and (B)

A solution of Z-Phe-N-Me-Val-N-Me-Phe(3-tBu-4-F)-NH$_2$ (AB) (104 mg, 0.161 mmol) and 10% palladium-carbon (100 mg) in methanol (70 ml) was stirred at room temperature for 22 hours in a hydrogen atmosphere. After removing the catalyst by filtration, the filtrate was concentrated under reduced pressure. The thus obtained residue was subjected to silica gel column chromatography (developing solvent:methanol:aqueous ammonia:methylene chloride= 5:0.1:100) to give two diastereoisomers A and B of Phe-N-Me-Val-N-Me-Phe(3-tBu-4-F)-NH$_2$, A (57 mg, 57%) being eluted first and then B (24 mg, 29%).

(A)

EI-MS:512(M$^+$) NMR (method a, CDCl$_3$): δ 0.34(3H,d, J=6.6 Hz), 0.81(3H,d,J=6.6 Hz), 1.34(9H,s), 2.00–2.20(1H, m), 2.50–3.45(3H,m), 2.98(1.5H,s), 3.01(1.5H,s), 3.89–3.94 (1H,m), 4.76(1H,d,J=10.6 Hz), 5.52–5.58(1H,m), 6.80–7.40 (8H,m)

(B)

EI-MS:512(M$^+$) NMR (method a, CDCl$_3$): δ 0.20(0.4H, d,J=6.6 Hz), 0.26(2.6H,d,J=6.6 Hz), 0.42(0.4H,d,J=6.3 Hz), 0.59(2.6H,d,J=6.6 Hz), 1.33(9H,s), 1.80–2.10(1H,m), 2.70–3.50(1H,m), 2.97(1.5H,s), 3.10(1.5H,s), 4.59(0.1H,d, J=11.2 Hz), 4.67(0.9H,d,J=10.9 Hz), 5.58–5.64(1H,m), 6.80–7.40(8H,m)

Example 9
Phe-N-Me-Val-N-Me-Phe(4-hydroxy-3-isobutyryl)-NH$_2$ (1) Synthesis of N-benzyloxycarbonyl-N-Me-L-3-(4-hydroxy-3-isobutyrylphenyl)Alaninamide To a solution of N-Me-L-tyrosine hydrochloride (1.48 g, 6.37 mmol) in nitrobenzene (35 ml), anhydrous aluminum chloride (3.40 g, 25.5 mmol) was added, followed by stirring at room temperature for 30 min. The mixture was mixed with isobutyryl chloride (0.80 ml, 7.64 mmol) and stirred at 100° C. for 6 hours. The reaction mixture was returned to room temperature and then poured into a mixture of ice water (50 ml) and concentrated hydrochloric acid (8 ml) under stirring. The aqueous layer was separated from the organic layer, washed with ethyl acetate and concentrated under reduced pressure. The residue was mixed with hydrochloric acid and left standing at 4° C. overnight, filtered to collect the thus formed precipitate and dried, giving N-Me-L-3-(4-hydroxy-3-isobutyrylphenyl)alanine hydrochloride (0.90 g).

To a mixture of the thus obtained compound (0.90 g, 3.39 mmol), sodium carbonate (1.80 g, 17.0 mmol), 1,4-dioxane (10 ml) and water (10 ml), benzyl chloroformate (0.58 ml, 4.07 mmol) was added under cooling with ice, followed by stirring for 2.5 hours at room temperature. The mixture was mixed with water and washed with ether; the aqueous layer was acidified by adding 2N hydrochloric acid and extracted with chloroform. The organic layer was dried over anhydrous magnesium sulfate and evaporated to remove the solvent under reduced pressure, giving N-benzyloxycarbonyl-N-Me-L-3-(4-hydroxy-3-isobutyrylphenyl)alanine (0.76 g).

Under cooling with ice, NMM (0.25 ml, 2.26 mmol) was added to a solution of the thus obtained compound (0.75 g, 1.88 mmol) in DMF (8 ml), followed by the addition of ethyl chloroformate (0.22 ml, 2.26 mmol). After stirring for 30 min., gaseous ammonia was blown into the mixture for 30 min. The mixture was returned to room temperature, left standing for a while, mixed with water and extracted with ethyl acetate. The organic layer was washed with water and saturated brine, dried over anhydrous magnesium sulfate and evaporated to remove the solvent under reduced pressure; the thus obtained residue was subjected to silica gel column chromatography (developing solvent: ethyl acetate:n-hexane=2:1) to give the titled compound (188 mg, 7%, in 3 steps).

NMR (method a, CDCl$_3$): δ 1.20(6H,d, J=6.9 Hz), 2.8–3.0 (1H,m), 2.88(3H,s), 3.3–3.4(1H,m), 3.4–3.6(1H,m), 4.75(3/10H,brs), 4.97(1H,dd,J=8.6,16.2 Hz), 5.10(2H,dd,J=−7.9, 20.6 Hz), 5.40(7/10H,brs), 5.78(3/10H,brs), 6.10(7/10H, brs), 6.91(1H,d,J=8.6 Hz), 7.2–7.4(6H,m), 7.64(1H,s), 12.4 (1H,s)

(2) Synthesis of N-Me-Val-N-Me-Phe(4-hydroxy-3-isobutyryl)-NH$_2$

To a solution of N-benzyloxycarbonyl-N-Me-L-3-(4-hydroxy-3-isobutyrylphenyl)alaninamide (184 mg, 0.462 mmol) in methanol (3 ml), 10% palladium carbon (30 mg) was added, followed by stirring for 4 hours in a hydrogen atmosphere. After removing the catalyst by filtration, the filtrate was evaporated under reduced pressure to give crude N-Me-L-3-(4-hydroxy-3-isobutyrylphenyl)alaninamide (124 mg).

To a solution of Fmoc-N-Me-Val-OH (146 mg, 0.414 mmol) in THF (0.6 ml)/ether (2.4 ml), under cooling with ice, oxalyl chloride (0.043 ml) and then a droplet of DMF were added, followed by stirring for 2 hours and then at room temperature for further 1 hour. The reaction mixture was concentrated. A solution of the thus obtained residue in methylene chloride (0.8 ml) was added to a solution of the above crude compound (73 mg, 0.276 mmol) and DIEA (0.15 ml, 0.828 mmol) in methylene chloride (1.5 ml) under cooling with ice, followed by stirring for 10 min. The reaction mixture was mixed with a saturated aqueous NaHCO$_3$ solution and extracted with methylene chloride. The organic layer was dried over anhydrous magnesium sulfate and evaporated to remove the solvent under reduced pressure. The thus obtained residue was subjected to silica gel column chromatography (developing solvent: chloroform:methanol=150:1) to give Fmoc-N-Me-Val-N-Me-Phe(4-hydroxy-3-isobutyryl)-NH$_2$ (145 mg, 87%).

To a solution of the thus obtained compound (145 mg, 0.242 mmol) in methylene chloride (2.5 ml), diethylamine (2 ml) was added, followed by stirring for 2 hours at room temperature. The mixture was evaporated to remove the solvent under reduced pressure. The thus obtained residue was subjected to silica gel column chromatography (developing solvent:chloroform:methanol:concentrated aqueous ammonia=40:1:0.1) to give two diastereoisomers A and B of the titled compound, A (43 mg, 47%) being eluted first and then B (28 mg, 31%).

(3) Synthesis of Phe-N-Me-Val-N-Me-Phe(4-hydroxy-3-isobutyryl)-NH$_2$ (A)

To a solution of N-Me-Val-N-Me-Phe(4-hydroxy-3-isobutyryl)-NH$_2$ (A) (43 mg, 0.114 mmol), Z-Phe-OH (51 mg, 0.171 mmol) and PyClU (68 mg, 0.205 mmol) in methylene chloride (1 ml), DIEA (0.060 ml, 0.342 mmol) was added under cooling with ice, followed by stirring at the same temperature for 2 hours and then at room temperature for 1 hour. The reaction mixture was mixed with water and extracted with methylene chloride. The organic layer was dried over anhydrous magnesium sulfate and evaporated to remove the solvent under reduced pressure. The thus obtained residue was subjected to silica gel column chromatography (developing solvent: chloroform:methanol=150:1) to give Z-Phe-N-Me-Val-N-Me-Phe(4-hydroxy-3-isobutyryl)-NH$_2$ (A) (64 mg, 85%).

To a solution of the thus obtained compound (64 mg, 0.097 mmol) in methanol (2 ml), 10% palladium carbon (10 mg) was added, followed by stirring for 6 hours in a hydrogen atmosphere. After removing the catalyst by filtration, the filtrate was evaporated under reduced pressure; the thus obtained residue was subjected to silica gel column chromatography (developing solvent:chloroform:methanol:aqueous ammonia=50:1:0.1) to give the titled compound (42 mg, 82%).

EI-MS:524(M$^+$) NMR (method a, CDCl$_3$): δ 0.68–0.93 (6H,m), 1.15–1.27(6H,m), 2.27–2.40(1H,m), 2.48–2.95(3H, m), 2.59(9/5H,s), 2.83(9/5H,s), 3.01(6/5H,s), 3.05(6/5H,s), 3.26(3/5H,dd,J=6.8,14.7 Hz), 3.45–3.71(7/5H,m), 3.74 H (3/5H,dd,J=5.7,8.1 Hz), 3.93(2/5H,dd,J=5.7,8.1 Hz), 4.98(2/5H,d,J=10.9 Hz), 5.10(3/5H,d,J=10.6 Hz), 5.0–5.2(2/5H,m), 5.30(1H,brs), 5.44(3/5H,dd,J=6.7,9.4 Hz), 5.90(1H,brs), 6.84(3/5H,d,J=8.6 Hz), 6.97(2/5H,d,J=8.6 Hz), 7.1–7.4(6H, m), 7.65(3/5H,d,J=1.7 Hz), 7.72(2/5H,d,J=1.7 Hz), 12.3(3/5H,s), 12.4(2/5H,s)

(4) Synthesis of Phe-N-Me-Val-N-Me-Phe(4-hydroxy-3-isobutyryl)-NH$_2$ (B)

To a solution of N-Me-Val-N-Me-Phe(4-hydroxy-3-isobutyryl)-NH$_2$ (B) (14 mg, 0.037 mmol), Z-Phe-OH (17 mg, 0.056 mmol) and PyClU (22 mg, 0.067 mmol) in methylene chloride (0.3 ml), DIEA (0.019 ml, 0.111 mmol) was added under cooling with ice, followed by stirring at the same temperature for 1 hour and then at room temperature for 3 hours. The reaction mixture was mixed with water and extracted with methylene chloride. The organic layer was dried over anhydrous magnesium sulfate and evaporated to remove the solvent under reduced pressure. The thus obtained residue was subjected to silica gel column chromatography (developing solvent:chloroform:methanol=150:1) to give Z-Phe-N-Me-Val-N-Me-Phe(4-hydroxy-3-isobutyryl)-NH$_2$ (B) (22 mg, 91%).

To a solution of the thus obtained compound (20 mg, 0.030 mmol) in methanol (1.5 ml), a catalytic amount of 10% palladium carbon was added, followed by stirring for 4 hours in a hydrogen atmosphere. After removing the catalyst by filtration, the filtrate was evaporated under reduced pressure; the thus obtained residue was subjected to silica gel column chromatography (developing solvent: chloroform:methanol:aqueous ammonia=50:1:0.1) to give the titled compound (12 mg, 75%).

EI-MS:524($M^+$) NMR (method a, $CDCl_3$): δ 0.44(3H,d, J=6.3 Hz), 0.82(3H,d,J=6.6 Hz), 1.24(6H,d,J=6.6 Hz), 2.0–2.2(1H,m), 2.64(1H,dd,J=7.6,13.5 Hz), 2.82–3.07(2H, m), 2.97(3H,s), 3.02(3H,s), 3.40(1H,dd,J=5.9,14.8 Hz), 3.5–3.7(1H,m), 3.93(1H,dd,J=1.0,6.3 Hz), 4.80(1H,d,J=10.9 Hz), 5.30(1H,brs), 5.52(1H,dd,J=6.1,10.1 Hz), 6.16(1H, brs), 6.91(1H,d,J=8.6 Hz), 7.14–7.36(6H,m), 7.64(1H,s), 12.4(1H,s)

Example 10

Phe-N-Me-Val-N-Me-[3-(5-tert-butyl-4-hydroxymethylfuran-2-yl)]Ala-$NH_2$ (1) Synthesis of methyl Ester of 4-Acetoxymethyl-5-tert-butylfuran-2-carboxylic Acid To a solution of 5-tert-butylfuran-2-carboxylic acid (4.10 g, 22.5 mmol) in acetic acid (40 ml), paraformaldehyde (3.38 g, 112 mmol) was added, followed by stirring at 80° C. Two hours after that, concentrated sulfuric acid (0.5 ml) was added followed by stirring for 4 days. Under cooling with ice, the reaction mixture was neutralized by the addition of saturated aqueous $NaHCO_3$ and extracted with methylene chloride. The organic layer was washed with water and saturated brine, dried over magnesium sulfate and evaporated to remove the solvent under reduced pressure; the thus obtained residue was subjected to silica gel column chromatography (developing solvent: ethyl acetate:n-hexane=1:10) to give the titled compound (3.16 g, 55%).

NMR (method a, $CDCl_3$): δ 1.39(9H,s), 2.08(3H,s), 3.86 (3H,s), 5.05(2H,s), 7.11(1H,s)

(2) Synthesis of methyl Ester of 5-tert-butyl-4-hydroxymethylfuran-2-carboxylic Acid To a solution of methyl ester of 4-acetoxymethyl-5-tert-butylfuran-2-carboxylic acid (3.16 g, 12.4 mmol) in methanol (15 ml), potassium carbonate (3.08 g, 22.3 mmol) was added, followed by stirring for 2 hours under cooling with ice. Under cooling with ice, the reaction mixture was mixed with a saturated aqueous $NH_4Cl$ solution and extracted with ethyl acetate. The organic layer was washed with water and saturated brine, dried over magnesium sulfate and evaporated to remove the solvent under reduced pressure; the thus obtained residue was subjected to silica gel column chromatography (developing solvent: ethyl acetate:n-hexane= 1:2) to give the titled compound (2.51 g, 95%).

NMR (method a, $CDCl_3$): δ 1.40(9H,s), 3.86(3H,s), 4.63 (2H,s), 7.15(1H,s)

(3) Synthesis of methyl Ester of 5-tert-butyl-4-Methoxymethoxymethylfuran-2-carboxylic Acid To the solution of methyl ester of 5-tert-butyl-4-hydroxymethylfuran-2-carboxylic acid (515 mg, 2.43 mmol) in methylene chloride (20 ml), N,N-diisopropylethylamine (0.677 ml, 3.89 mmol) and chlorodimethyl ether (0.277 ml, 3.65 mmol) were added under cooling with ice. The mixture was warmed to room temperature and stirred overnight. Under cooling with ice, the reaction mixture was mixed with saturated $NaHCO_3$ and extracted with methylene chloride. The organic layer was washed with water and saturated brine, dried over magnesium sulfate and evaporated to remove the solvent under reduced pressure; the thus obtained residue was subjected to silica gel column chromatography (developing solvent: ethyl acetate:n-hexane=1:5) to give the titled compound (495 mg, 80%).

NMR (method a, $CDCl_3$): δ 1.39(9H,s), 3.40(3H,s), 3.85 (3H,s), 4.53(2H,s), 4.66(2H,s), 7.13(1H,s)

(4) Synthesis of 5-tert-butyl-4-Methoxymethoxymethylfuran-2-carboaldehyde

Under cooling with ice, a solution of methyl ester of 5-tert-butyl-4-methoxymethoxymethylfuran-2-carboxylic acid (490 mg, 1.91 mmol) in THF (10 ml) was added to a suspension of lithium aluminum hydride (145 mg, 3.82 mmol) in THF (10 ml), followed by stirring for 1 hour. Under cooling with ice, the mixture was mixed with ethyl acetate and saturated aqueous $NH_4Cl$, filtered and the filtrate was extracted with ethyl acetate. The organic layer was washed with water and saturated brine, dried over magnesium sulfate and evaporated to remove the solvent. The thus obtained residue was dissolved in methylene chloride (20 ml) and mixed with manganese dioxide (2.49 g, 28.7 mmol), followed by stirring for 1 day. The reaction mixture was filtered and the filtrate was evaporated to remove the solvent; the thus obtained residue was subjected to silica gel column chromatography (developing solvent: ethyl acetate:n-hexane=1:4) to give the titled compound (379 mg, 88%).

NMR (method a, $CDCl_3$): δ 1.41(9H,s), 3.40(3H,s), 4.56 (2H,s), 4.68(2H,s), 7.22(1H,s), 9.52(1H,s)

(5) Synthesis of methyl Ester of 2-benzyloxycarbonylamino-3-(5-tert-butyl-4-Methoxymethoxymethylfuran-2-yl)Acrylic Acid To a suspension of potassium tert-butoxide (242 mg, 2.16 mmol) in methylene chloride (6 ml), a solution of (±)-Z-α-phosphonoglycine trimethyl ester (716 mg, 2.16 mmol) in methylene chloride (6 ml) was added at −78° C. in a nitrogen atmosphere, stirred for 15 min. and then further mixed with a solution of 5-tert-butyl-4-methoxymethoxymethylfuran-2-carboaldehyde (375 mg, 1.66 mmol) in methylene chloride (6 ml), followed by stirring for 4 hours at room temperature. The mixture was mixed with a saturated aqueous $NH_4Cl$ solution under cooling with ice and extracted with methylene chloride. The organic layer was washed with water and saturated brine, dried over magnesium sulfate and evaporated to remove the solvent under reduced pressure; the thus obtained residue was subjected to silica gel column chromatography (developing solvent: ethyl acetate:n-hexane= 1:2) to give the titled compound (664 mg, 93%).

NMR (method a, $CDCl_3$): δ 1.34(9H,s), 3.39(3H,s), 3.79 (3H,s), 4.49(2H,s), 4.65(2H,s), 5.16(2H,s), 6.58(1H,s), 6.66 (1H,brs), 6.98(1H,s), 7.30–7.40(5H,m)

(6) Synthesis of Z-N-Me-[3-(5-tert-butyl-4-Methoxymethoxymethylfuran-2-yl)]Ala-OMe To a solution of methyl ester of 2-benzyloxycarbonylamino-3-(5-tert-butyl-4-methoxymethoxymethylfuran-2-yl)acrylic acid (640 mg, 1.48 mmol) in methanol (15 ml), nickel chloride/hexahydrate (176 mg, 0.740 mmol) and sodium borohydride (336 mg, 8.88 mmol) were added, followed by stirring for 30 min. The reaction mixture was mixed with water and extracted with chloroform. The organic layer was washed with saturated brine, dried over magnesium sulfate and evaporated to remove the solvent under reduced pressure; under cooling with ice, to a solution of the thus obtained residue in DMF (10 ml) 60% sodium hydride (67.2 mg, 1.68 mmol) and methyl iodide (0.105 ml, 1.68 mmol) were added, followed by stirring for 30 min. Under cooling with ice, the reaction mixture was neutralized by the addition of a saturated aqueous $NH_4Cl$, extracted with ethyl acetate. The organic layer was washed with water and saturated brine, dried over magnesium sulfate and evaporated to remove the solvent under reduced pressure; the thus obtained residue was subjected to silica gel column chromatography (developing solvent: ethyl acetate:n-hexane=1:4) to give the titled compound (546 mg, 83%).

NMR (method a, CDCl$_3$): δ 1.29(9H,s), 2.86(39/23H,s), 2.87(30/23H,s), 3.00–3.30(3H,m), 3.38(3H,s), 3.65(30/23H, s), 3.75(39/23H,s), 4.44(2H,s), 4.63(2H,s), 4.70–4.95(1H, m), 5.09(2H,s), 5.96(10/23H,s), 5.99(13/23H,s), 7.30–7.40 (5H,m)

(7) Synthesis of N-Me-[3-(5-tert-butyl-4-Methoxymethoxymethylfuran-2-yl)]Ala-OMe To a solution of Z-N-Me-[3-(5-tert-butyl-4-methoxymethoxymethylfuran-2-yl)]Ala-OMe (536 mg, 1.20 mmol) in methanol (10 ml), 10% palladium carbon (150 mg) was added, followed by stirring for 3 hours at room temperature in a hydrogen atmosphere. The mixture was filtered and then the filtrate was concentrated under reduced pressure; the thus obtained residue was subjected to silica gel column chromatography (developing solvent: chloroform:methanol=10:1) to give the titled compound (295 mg, 79%).

NMR (method a, CDCl$_3$): δ 1.29(9H,s), 2.39(3H,s), 2.95 (2H,d,J=6.3 Hz), 3.39(3H,s), 3.46(1H,t,J=6.3 Hz), 3.73(3H, s), 4.46(2H,s), 4.65(2H,s), 6.01(1H,s)

(8) Synthesis of Z-Phe-N-Me-Val-N-Me-[3-(5-tert-butyl-4-Methoxymethoxymethylfuran-2-yl)]Ala-OMe To a solution of N-Me-[3-(5-tert-butyl-4-methoxymethoxymethylfuran-2-yl)]Ala-OMe (285 mg, 0.911 mmol) in methylene chloride (12 ml), Z-Phe-N-Me-Val-OH (564 mg, 1.37 mmol), PyClU (442 mg, 1.37 mmol) and DIEA (0.476 ml, 2.73 mmol) were added under cooling with ice, followed by stirring at room temperature overnight. The reaction mixture was mixed with water and extracted with methylene chloride. The organic layer was washed with water and saturated brine, dried over magnesium sulfate and evaporated to remove the solvent under reduced pressure; the thus obtained residue was subjected to silica gel column chromatography (developing solvent: ethyl acetate:n-hexane=1:2) to give the titled compound (542 mg, 84%).

NMR (method a, CDCl$_3$): δ 0.48–0.94(6H,m), 1.29(9H, s), 2.16–2.30(1H,m), 2.62–3.30(10H,m), 3.36(1H,s), 3.37 (2H,s), 4.34–4.48(2H,m), 4.56–4.64(2H,m), 4.88–5.04(2H, m), 5.03(2/3H,s), 5.04(4/3H,s), 5.86–6.00(1H,m), 7.16–7.40 (10H,m)

(9) Synthesis of Z-Phe-N-Me-Val-N-Me-[3-(5-tert-butyl-4-methoxymethoxymethylfuran-2-yl)]Ala-NH$_2$ To a solution of Z-Phe-N-Me-Val-N-Me-[3-(5-tert-butyl-4-methoxymethoxymethylfuran-2-yl)]Ala-OMe (632 mg, 0.894 mmol) in dioxane (8 ml), a 2N aqueous NaOH solution (2 ml) was added, followed by stirring at room temperature for 2 hours. Under cooling with ice, the mixture was rendered acidic by the addition of 2N hydrochloric acid, extracted with chloroform. The organic layer was washed with water and saturated brine, dried over magnesium sulfate and evaporated to remove the solvent under reduced pressure. The thus obtained residue was dissolved in THF (10 ml) and under cooling with ice, mixed with NMM (0.128 ml, 1.16 mmol) and ethyl chloroformate (0.111 ml, 1.16 mmol), followed by stirring for 15 min. The reaction mixture was stirred for further 30 min., while bubbling gaseous ammonia therein. After being left standing at room temperature, the reaction mixture was diluted with chloroform and washed with water. The organic layer was washed with saturated brine, dried over magnesium sulfate and evaporated to remove the solvent under reduced pressure; the thus obtained residue was subjected to silica gel column chromatography (developing solvent: ethyl acetate:n-hexane=1:2) to give the titled compound (481 mg, 78%).

NMR (method a, CDCl$_3$): δ 0.48–0.92(6H,m), 1.28(9/2H, s), 1.29(9/2H,s), 2.00–2.30(1H,m), 2.68–3.30(10H,m), 3.38 (3H,s), 4.38–4.48(2H,m), 4.61(8/5H,s), 4.64(2/5H,s), 4.80–5.54 (6H,m), 5.86–6.20(2H,m), 7.16–7.40(10H,m)

(10) Synthesis of Phe-N-Me-Val-N-Me-[3-(5-tert-butyl-4-methoxymethoxymethylfuran-2-yl)]Ala-NH$_2$ To a solution of Z-Phe-N-Me-Val-N-Me-[3-(5-tert-butyl-4-methoxymethoxymethylfuran-2-yl)]Ala-NH$_2$(420 mg, 0.607 mmol) in methanol (5 ml), 10% palladium carbon (150 mg) was added, followed by stirring at room temperature overnight in a hydrogen atmosphere. The mixture was filtered and the filtrate was concentrated under reduced pressure; the thus obtained residue was subjected to silica gel column chromatography (developing solvent: chloroform:methanol=10:1) to give two diastereoisomers A and B of the titled compound, A (97.2 mg, 29%) being eluted first and then B (95.0 mg, 28%).

(11) Synthesis of Phe-N-Me-Val-N-Me-[3-(5-tert-butyl-4-hydroxymethylfuran-2-yl)]Ala-NH$_2$ (A)

To a solution of Phe-N-Me-Val-N-Me-[3-(5-tert-butyl-4-methoxymethoxymethylfuran-2-yl)]Ala-NH$_2$ (A) (97.0 mg, 0.174 mmol) in THF (1 ml), 6N hydrochloric acid (1 ml) was added under cooling with ice, followed by stirring for 3 hours at room temperature. The mixture was mixed with saturated aqueous NaHCO$_3$ under cooling with ice and extracted with chloroform. The organic layer was washed with water and saturated brine, dried over magnesium sulfate and evaporated to remove the solvent under reduced pressure; the thus obtained residue was subjected to preparative thin-layer chromatography (developing solvent: chloroform:methanol=10:1) to give the titled compound (40.7 mg, 46%).

EI-MS: (M$^+$) 514 NMR (method a, CDCl$_3$): δ 0.60–1.02 (6H,m), 1.27(18/5H,s), 1.30(18/5H,s), 1.34(9/5H,s), 2.10–2.26(1H,m), 2.58–3.14(5H,m), 2.69(1H,s), 2.76(1H,s), 2.96(4/7H,s), 2.99(10/7H,s), 3.01(10/7H,s), 3.07(4/7H,s), 3.82–3.98(1H,m), 4.43(1/3H,s), 4.49(10/21H,s), 4.53(4/21H,s), 4.88–5.46(3H,m), 5.85(8/21H,s), 6.02(10/21H,s), 6.09(4/21H,s), 6.10–6.20(1H,m), 7.12–7.40(5H,m)

(12) Synthesis of Phe-N-Me-Val-N-Me-[3-(5-tert-butyl-4-hydroxymethylfuran-2-yl)]Ala-NH$_2$ (B)

To a solution of Phe-N-Me-Val-N-Me-[3-(5-tert-butyl-4-methoxymethoxymethylfuran-2-yl)]Ala-NH$_2$ (B) (94.1 mg, 0.169 mmol) in THF (1 ml), 6N hydrochloric acid (1 ml) was added under cooling with ice, followed by stirring for 2 hours at room temperature. The mixture was mixed with saturated aqueous NaHCO$_3$ under cooling with ice and extracted with chloroform. The organic layer was washed with water and saturated brine, dried over magnesium sulfate and evaporated to remove the solvent under reduced pressure; the thus obtained residue was subjected to preparative thin-layer chromatography (developing solvent: chloroform:methanol=10:1) to give the titled compound (47.8 mg, 55%).

EI-MS: (M$^+$) 514 NMR (method a, CDCl$_3$): δ 0.59–0.99 (6H,m), 1.27(9/2H,s), 1.29(9/2H,s), 2.02–2.15(1H,m), 2.68 (1H,dd,J=8.6,13.3 Hz), 2.80–3.12(4H,m), 3.01(6/5H,s), 3.02(9/5H,s), 3.07(9/5H,s), 3.08(6/5H,s), 3.86–4.02(1H,m), 4.40–4.56(2H,m), 4.88–5.62(3H,m), 5.89(2/7H,s), 5.97(5/21H,s), 5.98(10/21H,s), 6.10–6.40(1H,m), 7.12–7.40(5H,m)

Example 11

Phe-N-Me-Val-Tyr (3-NMe$_2$)-NH$_2$ (1) Synthesis of N-Me-Tyr(Bzl)-NH$_2$

Under cooling with ice, NMM (0.463 ml, 4.21 mmol) and ethyl chloroformate (0.403 ml, 4.21 mmol) were added to a solution of Boc-N-Me-Tyr(Bzl)-OH (1.35 g, 3.51 mmol) in THF (35 ml), followed by stirring for 15 min. The reaction mixture was stirred for further 30 min., while bubbling gaseous ammonia therein. The reaction mixture was then left standing at room temperature, diluted with ethyl acetate and washed with water and saturated brine. The organic layer was dried over magnesium sulfate and evaporated to remove the solvent under reduced pressure; the thus obtained residue was subjected to silica gel column chromatography (developing solvent: ethyl acetate:n-hexane=1:1) to give Boc-N-Me-Tyr(Bzl)-NH$_2$ (1.32 g, 98%).

To a solution of the thus obtained compound (1.32 g, 3.44 mmol) in methylene chloride (10 ml), TFA (5 ml) was added, followed by stirring for 1 hour at room temperature. The reaction mixture was evaporated under reduced pressure and under cooling with ice, neutralized by the addition of saturated aqueous NaHCO$_3$ and extracted with methylene chloride. The organic layer was washed with saturated brine, dried over magnesium sulfate and evaporated to remove the solvent under reduced pressure; the thus obtained residue was subjected to silica gel column chromatography (developing solvent: chloroform:methanol=20:1) to give the titled compound (791 mg, 79%).

NMR (method a, CDCl$_3$): δ 2.31(3H,s), 2.60–2.78(1H, m), 3.10–3.22(2H,m), 5.05(2H,s), 5.30(1H,brs), 6.94(2H,d, J=8.6 Hz), 6.99(1H,brs), 7.15(2H,d,J=8.6 Hz), 7.30–7.56 (5H,m)

(2) Synthesis of Fmoc-N-Me-Val-N-Me-Tyr(Bzl)-NH$_2$

To a solution of N-Me-Tyr(Bzl)-NH$_2$(329 mg, 1.16 mmol) in THF (15 ml), Fmoc-N-Me-Val-OH (533 mg, 1.51 mmol), CMPI (415 mg, 1.62 mmol) and TEA (0.323 ml, 2.32 mmol) were added under cooling with ice, followed by stirring for 4 hours at room temperature. The reaction mixture was mixed with water and extracted with ethyl acetate. The organic layer was washed with saturated brine, dried over magnesium sulfate and evaporated to remove the solvent under reduced pressure; the thus obtained residue was subjected to silica gel column chromatography (developing solvent: ethyl acetate:n-hexane=2:1) to give the titled compound (680 mg, 95%).

NMR (method a, CDCl$_3$): δ 0.17(6/5H,d,J=6.9 Hz), 0.40 (3/5H,d,J=6.9 Hz), 0.42(6/5H,d,J=6.9 Hz), 0.72(3/5H,d,J= 6.6 Hz), 0.77(6/5H,d,J=6.6 Hz), 0.88(6/5H,d,J=6.6 Hz), 2.10–2.30(1H,m), 2.31(3/2H,s), 2.33(3/2H,s), 2.58–3.32 (3H,m), 2.80(3/4H,s), 2.90(3/2H,s), 2.96(3/4H,s), 3.51(2/ 3H,d,J=10.6 Hz), 4.14–4.68(4H,m), 4.74–5.40(5H,m), 5.26 (1/2H,brs), 5.83(1/2H,brs), 5.92(1/2H,brs), 6.10(1/2H,brs), 6.79(1/2H,d,J=6.6 Hz), 6.82(1H,d,J=6.6 Hz), 6.89(1H,d,J= 6.6 Hz), 7.05(1/2H,d,J=6.6 Hz), 7.13(1/2H,d,J=6.6 Hz), 7.22–7.62(8H,m), 7.70–7.80(2H,m)

(3) Synthesis of N-Me-Val-N-Me-Tyr-NH$_2$

Fmoc-N-Me-Val-N-Me-Tyr(Bzl)-NH$_2$(802 mg, 1.29 mmol) was dissolved in a mixed solution of MeOH (6 ml) and ethyl acetate (6 ml), mixed with 20% palladium hydroxide-carbon (150 mg), followed by stirring in a hydrogen atmosphere at room temperature for 2 days. The mixture was filtered and the filtrate was concentrated under reduced pressure; the thus obtained residue was subjected to silica gel column chromatography (developing solvent: chloroform:methanol 10:1) to give the titled compound (216 mg, 55%).

NMR (method a, CDCl$_3$): δ 0.39(1/2H,d,J=6.6 Hz), 0.75 (1/2H,d,J=6.6 Hz), 0.93(5/2H,d,J=6.9 Hz), 0.96(5/2H,d,J= 6.9 Hz), 1.84(5/2H,s), 2.22(1/2H,s), 2.90–3.24(3H,m), 2.98 (2H,s), 3.49(1H,s), 5.27(1H,brs), 5.56(1H,dd,J=6.3,10.2 Hz), 6.10(1H,brs), 6.72(2H,d,J=8.2 Hz), 6.99(1/6H,d,J=8.2 Hz), 7.08(5/6H,d,J=8.2 Hz)

(4) Synthesis of Fmoc-Phe-N-Me-Val-Tyr-NH$_2$

To a solution of N-Me-Val-N-Me-Tyr-NH$_2$(185 mg, 0.603 mmol) in THF (6 ml), Fmoc-Phe-OH (304 mg, 0.784 mmol), CMPI (200 mg, 0.784 mmol) and TEA (0.168 ml, 1.21 mmol) were added under cooling with ice, followed by stirring at room temperature overnight. The reaction mixture was mixed with water and extracted with ethyl acetate. The organic layer was washed with saturated brine, dried over magnesium sulfate and evaporated to remove the solvent under reduced pressure; the thus obtained residue was subjected to silica gel column chromatography (developing solvent: ethyl acetate:n-hexane=2:1) to give the titled compound (197 mg, 48%).

NMR (method a, CDCl$_3$): δ 0.72(2H,d,J=6.6 Hz), 0.90 (2H,d,J=6.6 Hz), 0.94–1.04(2H,m), 2.20–2.40(1H,m), 2.35 (3/2H,s), 2.68(3H,s), 2.60–3.20(4H,m), 2.98(3/2H,s), 4.10–4.40(3H,m), 4.60–5.02(3H,m), 5.20–5.44(3H,m), 5.90 (1H,brs), 6.60–6.98(4H,m), 7.02–7.20(1H,m), 7.28–7.80 (10H,m)

(5) Synthesis of Fmoc-Phe-N-Me-Val-Tyr(3-NO$_2$)-NH$_2$

To a solution of Fmoc-Phe-N-Me-Val-Tyr-NH$_2$(230 mg, 0.340 mmol) in methylene chloride (1 ml) and acetic acid (1 ml), fuming nitric acid (0.03 ml) was added under cooling with ice, followed by stirring at room temperature for 1 hour. The reaction mixture was mixed with water and extracted with methylene chloride. The organic layer was washed with saturated brine, dried over magnesium sulfate and evaporated to remove the solvent under reduced pressure; the thus obtained residue was subjected to silica gel column chromatography (developing solvent: ethyl acetate:n-hexane= 2:1) to give the titled compound (204 mg, 83%).

NMR (method a, CDCl$_3$): δ 0.70–0.92(6H,m), 2.20–2.40 (1H,m), 2.76(2H,s), 2.82(2H,s), 3.00(1H,s),3.04(1H,s), 2.60–3.40(4H,m), 4.10–4.50(3H,m), 4.80–5.50(5H,m), 5.91 (1H,brs), 7.02–8.00(15H,m), 10.39(2/3H,s), 10.49(1/3H,s)

(6) Synthesis of Fmoc-Phe-N-Me-Val-Tyr(3-NMe$_2$)-NH$_2$

To a solution of Fmoc-Phe-N-Me-Val-Tyr(3-NO$_2$)-NH$_2$ (203 mg, 0.282 mmol) in ethanol (3 ml), 10% palladium-carbon (150 mg) was added, followed by stirring in a hydrogen atmosphere at room temperature for 4 hours. The reaction mixture was mixed with formaldehyde (35%) (0.145 mmol, 1.69 mmol), followed by further stirring in a hydrogen atmosphere overnight. After filtering the reaction mixture, the filtrate was concentrated under reduced pressure; the thus obtained residue was mixed with water and extracted with chloroform. The organic layer was washed with saturated brine, dried over magnesium sulfate and evaporated to remove the solvent under reduced pressure; the thus obtained residue was subjected to silica gel column chromatography (developing solvent: chloroform:methanol 10:1) to give the titled compound (165 mg, 81%).

(7) Synthesis of Phe-N-Me-Val-Tyr(3-NMe$_2$)-NH$_2$

To a solution of Fmoc-Phe-N-Me-Val-Tyr(3-NMe$_2$)-NH$_2$ (163 mg, 0.227 mmol) in methylene chloride (1.5 ml), diethylamine (1 ml) was added, followed by stirring at room temperature for 3 hours. The reaction mixture was concentrated under reduced pressure; the thus obtained residue was subjected to silica gel column chromatography (developing solvent: chloroform:methanol:aqueous ammonia=10:1:0.1) to give the titled compound (91.2 mg, 81%).

EI-MS: (M$^+$) 497 NMR (method a, CDCl$_3$): δ 0.52(3/4H, d,J=6.6 Hz), 0.78(3/4H,d,J=6.3 Hz), 0.80(9/4H,d,J=6.6 Hz), 0.92(9/4H,d,J=6.3 Hz), 2.20–2.38(1H,m), 2.46(2H,s), 2.56 (4H,s), 2.64(2H,s), 2.75(2H,s), 2.70–3.04(3H,m), 3.01(1H, s), 3.02(1H,s), 3.17(2/3H,dd,J=5.6,14.8 Hz), 3.33(1/3H,dd, J=7.0,13.8 Hz), 3.73(2/3H,dd,J=6.0,7.6 Hz), 3.02(1/3H,dd, J=6.0,7.6 Hz), 4.88–5.12(1H,m), 5.30(1H,brs), 5.42(1H,dd, J=6.0,10.2 Hz), 5.91(1H,brs), 6.66(2/3H,dd,J=1.7,8.2 Hz), 6.73(2/3H,d,J=8.2 Hz), 6.86(1/3H,d,J=8.2 Hz), 6.93(1/3H, dd,J=1.6,8.2 Hz), 7.01(2/3H,d,J=1.7 Hz), 7.06(1/3H,d,J=1.6 Hz), 7.10–7.40(5H,m)

Example 12
Phe-N-Me-Val-N-Me-[3-(5-tert-butyl-4-carboxyfuran-2-yl)]Ala-NH$_2$ (1) Synthesis of Methyl Ester of 5-tert-butyl-4-tert-butyldimethylsilanyloxymethylfuran-2-carboxylic acid Under cooling with ice, imidazole (2.30 g, 33.8 mmol) and tert-butyldimethylchlorosilane (5.09 g, 33.8 mmol) were added to a solution of methyl ester of 5-tert-butyl-4-hydroxymethylfuran-2-carboxylic acid (7.17 g, 33.8 mmol) in DMF (100 ml), followed by stirring for 2 hours. Under cooling with ice, the reaction mixture was mixed with saturated NaHCO$_3$ and extracted with ethyl acetate. The organic layer was washed with water and saturated brine, dried over magnesium sulfate and evaporated to remove the solvent under reduced pressure; the thus obtained residue was subjected to silica gel column chromatography (developing solvent: ethyl acetate:n-hexane=1:4) to give the titled compound (10.7 g, 97%).

NMR (method a, CDCl$_3$): δ 0.08(6H,s), 0.92(9H,s), 1.36 (9H,s), 3.85(3H,s), 4.62(2H,s), 7.12(1H,s)

(2) Synthesis of 5-tert-butyl-4-tert-butyldimethylsilanyloxymethylfuran-2-carboaldehyde Under cooling with ice, a solution of methyl ester of 5-tert-butyl-4-tert-butyldimethylsilanyloxymethylfuran-2-carboxylic acid (2.16 g, 6.63 mmol) in diethyl ether (20 ml) was added to a suspension of lithium aluminum hydride (503 mg, 13.3 mmol) in diethyl ether (20 ml), followed by stirring for 1 hour. Under cooling with ice, the mixture was mixed with ethyl acetate and saturated aqueous NH$_4$Cl and filtered. The filtrate was extracted with ethyl acetate and the organic layer was washed with water and saturated brine, dried over magnesium sulfate and evaporated to remove the solvent. The thus obtained residue was dissolved in methylene chloride (80 ml), mixed with manganese dioxide (5.76 g, 66.3 mmol) and stirred overnight. After filtering the reaction mixture, the filtrate was evaporated to remove the solvent to give the titled compound (1.58 g, 81%).

NMR (method a, CDCl$_3$): δ 0.10(6H,s), 0.93(9H,s), 1.38 (9H,s), 4.66(2H,s), 7.23(1H,s), 9.50(1H,s)

(3) Synthesis of Methyl Ester 2-benzyloxycarbonylamino-3-(5-tert-butyl-4-tert-butyldimethylsilanyloxymethylfuran-2-yl)acrylic acid In a nitrogen atmosphere at −78° C., a solution of (±)-Z-α-phosphonoglycine trimethyl ester (1.82 g, 5.50 mmol) in methylene chloride (10 ml) was added to a solution of potassium tert-butoxide (645 mg, 5.75 mmol) in methylene chloride (25 ml), followed by stirring for 15 min. To the mixture, a solution of 5-tert-butyl-4-tert-butyldimethylsilanyloxymethylfuran-2-carboaldehyde (1.48 g, 5.00 mmol) in methylene chloride (10 ml) was further added, followed by stirring at room temperature overnight. The mixture was then mixed with saturated aqueous NH$_4$Cl under cooling with ice and extracted with methylene chloride. The organic layer was washed with water and saturated brine, dried over magnesium sulfate and evaporated to remove the solvent under reduced pressure; the thus obtained residue was subjected to silica gel column chromatography (developing solvent: ethyl acetate:n-hexane=1:4) to give the titled compound (1.65 g, 66%).

NMR (method a, CDCl$_3$): δ 0.07(6H,s), 0.91(9H,s), 1.31 (9H,s), 3.79(3H,s), 4.60(2H,s), 5.16(2H,s), 6.60(1H,s), 6.68 (1H,brs), 6.98(1H,s), 7.30–7.40(5H,m)

(4) Synthesis of Z-N-Me-[3-(5-tert-butyl-4-tert-butyldimethylsilanyloxymethylfuran-2-yl)]Ala-OMe To a solution of methyl ester of 2-benzyloxycarbonylamino-3-(5-tert-butyl-4-tert-butyldimethylsilanyloxymethylfuran-2-yl)acrylic acid (1.65 g, 3.29 mmol) in methanol (30 ml), nickel chloride/hexahydrate (782 mg, 3.29 mmol) and sodium borohydride (996 mg, 26.3 mmol) were added under cooling with ice, followed by stirring for overnight at room temperature. The reaction mixture was mixed with water, extracted with chloroform. The organic layer was washed with saturated brine, dried over magnesium sulfate and evaporated to remove the solvent under reduced pressure; the thus obtained residue was subjected to silica gel column chromatography (developing solvent: ethyl acetate:n-hexane=1:4) to give Z-[3-(5-tert-butyl-4-tert-butyldimethylsilanyloxymethylfuran-2-yl)]Ala-OMe (801 mg, 48%).

Under cooling with ice to a solution of the thus obtained compound (800 mg, 1.59 mmol) in DMF (15 ml), 60% sodium hydride (82.7 mg, 2.07 mmol) and methyl iodide (0.198 ml, 3.18 mmol) were added and stirred for 1 hour. Under cooling with ice, the reaction mixture was neutralized by the addition of a saturated aqueous NH$_4$Cl and extracted with ethyl acetate. The organic layer was washed with water and saturated brine, dried over magnesium sulfate and evaporated to remove the solvent under reduced pressure; the thus obtained residue was subjected to silica gel column chromatography (developing solvent: ethyl acetate:n-hexane=1:4) to give the titled compound (697 mg, 85%).

NMR (method a, CDCl$_3$): δ 0.05(36/11H,s), 0.06(30/11H, s), 0.89(54/11H,s), 0.90(45/11H,s), 1.26(45/11H,s), 1.27(54/11H,s), 2.85(15/11H,s), 2.87(18/11H,s), 2.96–3.30(2H,m), 3.64(15/11H,s), 3.74(18/11H,s), 4.55(2H,s), 4.70–5.12(3H, m), 5.96(15/11H,s), 5.99(18/11H,s), 7.30–7.40(5H,m)

(5) Synthesis of Z-N-Me-[3-(5-tert-butyl-4-tert-butyldimethylsilanyloxymethylfuran-2-yl)]Ala-NH$_2$ To a solution of Z-N-Me-[3-(5-tert-butyl-4-tert-butyldimethylsilanyloxymethylfuran-2-yl)]Ala-OMe (697 mg, 1.35 mmol) in dioxane (7 ml), a solution of NaOH (162 mg, 4.05 mmol) in water (7 ml) was added, followed by stirring at room temperature overnight. Under cooling with ice, the mixture was rendered acidic by the addition of 2N hydrochloric acid and extracted with chloroform. The organic layer was washed with water and saturated brine, dried over magnesium sulfate and evaporated to remove the solvent under reduced pressure. The thus obtained residue was dissolved in THF (13 ml) and under cooling with ice, mixed with NMM (0.178 ml, 1.62 mmol) and ethyl chloroformate (0.155 ml, 1.62 mmol), followed by stirring for 10 min. The reaction mixture was stirred for further 30 min. while bubbling gaseous ammonia therein. The reaction mixture was left standing at room temperature, diluted with chloroform washed with water, The organic layer was washed with saturated brine and dried over magnesium sulfate and evaporated to remove the solvent under reduced pressure; the thus obtained residue was subjected to silica gel column chromatography (developing solvent: ethyl acetate:n-hexane=1:4) to give the titled compound (427 mg, 63%).

(6) Synthesis of N-Me-[3-(5-tert-butyl-4-tert-butyldimethylsilanyloxymethylfuran-2-yl)]Ala-NH$_2$ To a solution of Z-N-Me-[3-(5-tert-butyl-4-tert-butyldimethylsilanyloxymethylfuran-2-yl)]Ala-NH$_2$(425 mg, 0.847 mmol) in methanol (8 ml), 10% palladium-carbon (100 mg) was added and stirred at room temperature overnight in a hydrogen atmosphere. After filtering the mixture, the filtrate was concentrated under reduced pressure; the thus obtained residue was subjected to silica gel column chromatography (developing solvent: chloroform:methanol=10:1) to give the titled compound (107 mg, 34%).

NMR (method a, CDCl₃): δ 0.07(6H,s), 0.91(9H,s), 1.30 (9H,s), 2.36(3H,s), 2.73(1H,dd,J=9.9,15.2 Hz), 3.10–3.24 (2H,m), 4.59(2H,s), 5.31(1H,brs), 6.05(1H,s), 7.15(1H,brs)

(7) Synthesis of Z-Phe-N-Me-Val-N-Me-[3-(5-tert-butyl-4-tert-butyldimethylsilanyloxymethylfuran-2-yl)]Ala-NH₂

To a solution of N-Me-[3-(5-tert-butyl-4-tert-butyldimethylsilanyloxymethylfuran-2-yl) ]Ala-NH₂(33.0 mg, 0.0897 mmol) in THF (1 ml), Z-Phe-N-Me-Val-OH (48.2 mg, 0.117 mmol), CMPI (29.9 mg, 0.117 mmol) and TEA (0.038 ml, 0.27 mmol) were added under cooling with ice, followed by stirring at room temperature overnight. The reaction mixture was mixed with water and extracted with ethyl acetate. The organic layer was washed with saturated brine, dried over magnesium sulfate and evaporated to remove the solvent under reduced pressure; the thus obtained residue was subjected to silica gel column chromatography (developing solvent: ethyl acetate:n-hexane=1:2) to give two diastereoisomers A and B of the titled compound, A (15.5 mg, 23%) being eluted first and then B (13.3 mg, 20%).

(8) Synthesis of Z-Phe-N-Me-Val-N-Me-[3-(5-tert-butyl-4-formylfuran-2-yl)]Ala-NH₂ (A)

To a solution of Z-Phe-N-Me-Val-N-Me-[3-(5-tert-butyl-4-tert-butyldimethylsilanyloxymethylfuran-2-yl)]Ala-NH₂ (A) (14.1 mg, 0.0185 mmol) in THF (1 ml), tetrabutylammonium fluoride (as a 1M solution in THF) (0.0925 ml, 0.0925 mmol) was added, followed by stirring at room temperature overnight. The reaction mixture was mixed with a saturated aqueous NH₄Cl solution and extracted with chloroform. The organic layer was washed with saturated brine, dried over magnesium sulfate and evaporated to remove the solvent under reduced pressure; the thus obtained residue was dissolved in methylene chloride (1 ml), mixed with manganese dioxide (32.2 mg, 0.370 mmol) and stirred for 3 hours at room temperature. The reaction mixture was filtered and the filtrate was evaporated under reduced pressure; the thus obtained residue was subjected to preparative thin-layer chromatography (developing solvent: ethyl acetate:n-hexane=1:1) to give the titled compound (8.5 mg, 71%).

(9) Synthesis of Z-Phe-N-Me-Val-N-Me-[3-(5-tert-butyl-4-carboxyfuran-2-yl)]Ala-NH₂ (A)

To a solution of Z-Phe-N-Me-Val-N-Me-[3-(5-tert-butyl-4-formylfuran-2-yl)]Ala-NH₂ (A) (8.0 mg, 0.012 mmol) in tert-butanol (0.4 ml)/2-methyl-2-butene (0.2 ml), a 1.0N sodium chlorite solution (20% sodium dihydrogen phosphate solution) (1.0 ml) was added under cooling with ice, followed by stirring at room temperature for 30 min. The reaction mixture was diluted with chloroform and washed with saturated brine. The organic layer was dried over magnesium sulfate and evaporated to remove the solvent under reduced pressure to give the titled compound (8.0 mg, 98%).

(10) Synthesis of Phe-N-Me-Val-N-Me-[3-(5-tert-butyl-4-carboxyfuran-2-yl)]Ala-NH₂ (A)

To a solution of Z-Phe-N-Me-Val-N-Me-[3-(5-tert-butyl-4-carboxyfuran-2-yl)]Ala-NH₂ (A) (7.0 mg, 0.0106 mmol) in methanol (1 ml), 10% palladium-carbon (5 mg) was added, followed by stirring in a hydrogen atmosphere at room temperature overnight. The mixture was filtered and the filtrate was concentrated under reduced pressure. The thus obtained residue was subjected to preparative thin-layer chromatography (developing solvent: chloroform:methanol=10:1) to give the titled compound (3.0 mg, 54%).

NMR (method a, CD₃OD): δ 0.49(3H,d,J=6.6 Hz), 0.56 (3H,d,J=6.6 Hz), 1.32(9H,s), 1.98–2.10(1H,m), 2.90(3H,s), 3.06(3H,s), 2.80–3.14(4H,m), 4.50–4.60(1H,m), 4.80–4.88 (1H,m), 5.32–5.44(1H,m), 6.36(1H,s), 7.20–7.34(5H,m)

(11) Synthesis of Phe-N-Me-Val-N-Me-[3-(5-tert-butyl-4-carboxyfuran-2-yl)]Ala-NH₂ (B)

Under cooling with ice, tetrabutylammonium fluoride (as a 1M solution in THF) (3.16 ml, 3.16 mmol) was added to a solution of Z-Phe-N-Me-Val-N-Me-[3-(5-tert-butyl-4-tert-butyldimethylsilanyloxymethylfuran-2-yl) ]Ala-NH₂ (B) (481 mg, 0.631 mmol) in THF (6 ml), followed by stirring for 3 hours. The reaction mixture was mixed with a saturated aqueous NH₄Cl solution and extracted with chloroform. The organic layer was washed with saturated brine, dried over magnesium sulfate and evaporated to remove the solvent under reduced pressure; the thus obtained residue was subjected to silica gel column chromatography (ethyl acetate:n-hexane=1:1) to give Z-Phe-N-Me-Val-N-Me-[3-(5-tert-butyl-4-hydroxymethylfuran-2-yl)]Ala-NH₂ (B) (382 mg, 93%).

To a solution of the thus obtained compound (382 mg, 0.589 mmol) in methylene chloride (10 ml), manganese dioxide (512 mg, 5.89 mmol) was added, followed by stirring at room temperature overnight. The reaction mixture was filtered and the filtrate was evaporated under reduced pressure; the thus obtained residue was dissolved in tert-butanol (10 ml)/2-methyl-2-butene (5 ml) and under cooling with ice, mixed with a 1.0N sodium chlorite solution (20% sodium dihydrogen phosphate solution) (10 ml), followed by stirring at room temperature for 3 hours. The reaction mixture was diluted with chloroform and washed with saturated brine. The organic layer was dried over magnesium sulfate and evaporated to remove the solvent under reduced pressure to give the titled compound (274 mg, 70%).

(12) Synthesis of Phe-N-Me-Val-N-Me-[3-(5-tert-butyl-4-carboxyfuran-2-yl)]Ala-NH₂ (B)

To a solution of Z-Phe-N-Me-Val-N-Me-[3-(5-tert-butyl-4-carboxyfuran-2-yl)]Ala-NH₂ (B) (10.2 mg, 0.0154 mmol) in methanol (1 ml), 10% palladium carbon (3 mg) was added, followed by stirring in a hydrogen atmosphere at room temperature overnight. The mixture was filtered and the filtrate was concentrated under reduced pressure. The thus obtained residue was subjected to preparative thin-layer chromatography (developing solvent: chloroform:methanol=10:1) to give the titled compound (5.7 mg, 70%).

NMR (method a, CD₃OD): δ 0.40(1/3H,d,J=6.6 Hz), 0.57(2/3H,d,J=6.0 Hz), 0.64(2H,d,J=6.6 Hz), 0.91(3H,d,J=6.2 Hz), 1.39,1.43,1.44 (total 9H,each s), 2.10–2.24(1H,m), 2.43(3/5H,s), 2.65(3/5H,s), 2.76(12/5H,s), 3.09(12/5H,s), 2.68–3.10(4H,m), 4.40–4.60(1H,m), 5.02–5.14(1H,m), 5.36–5.46(1H,m), 6.12(5/7H,s), 6.16(1/7H,s), 6.47(1/7H,s), 7.20–7.40(5H,m), 7.85(1H,s)

Example 13

Phe-N-Me-Val-N-Me-[3-(5-tert-butyl-4-carbamoylfuran-2-yl) ]Ala-NH₂

(1) Synthesis of Z-Phe-N-Me-Val-N-Me-[3-(5-tert-butyl-4-carbamoylfuran-2-yl)]Ala-NH₂

Under cooling with ice, NMM (0.077 ml, 0.698 mmol) and ethyl chloroformate (0.056 ml, 0.582 mmol) were added to a solution of Z-Phe-N-Me-Val-N-Me-[3-(5-tert-butyl-4-carboxyfuran-2-yl)]Ala-NH₂ (A) (257 mg, 0.388 mmol) in THF (4 ml), followed by stirring for 5 min. The reaction mixture was further stirred for 1 hour while bubbling gaseous ammonia therein. The reaction mixture was left standing at room temperature, diluted with chloroform and washed with water. The organic layer was washed with saturated brine, dried over magnesium sulfate and evaporated to remove the solvent under reduced pressure; the thus obtained residue was subjected to preparative thin-layer chromatography (developing solvent: ethyl acetate) to give the titled compound (59.2 mg, 23%).

(2) Synthesis of Phe-N-Me-Val-N-Me-[3-(5-tert-butyl-4-carbamoylfuran-2-yl)]Ala-NH$_2$ To a solution of Z-Phe-N-Me-Val-N-Me-[3-(5-tert-butyl-4-carbamoylfuran-2-yl)]Ala-NH$_2$(58.0 mg, 0.0877 mmol) in methanol (1 ml), 10% palladium-carbon (20 mg) was added and stirred at room temperature overnight in a hydrogen atmosphere. After filtering the mixture, the filtrate was concentrated under reduced pressure; the thus obtained residue was subjected to preparative thin-layer chromatography (developing solvent: chloroform:methanol=10:1) to give the titled compound (7.5 mg, 16%).

NMR (method a, CD$_3$OD): δ 0.64(18/5H,t,J=6.6 Hz), 0.74(6/5H,d,J=6.6 Hz), 0.89(6/5H,d,J=6.3 Hz), 1.36(27/5H, s), 1.39(18/5H,s), 2.00–2.20(1H,m), 2.68–2.90(1H,m), 2.81 (1H,s), 3.00(2H,s), 3.12(3H,s), 2.94–3.20(2H,m), 3.20–3.40 (1H,m), 3.81(2/7H,dd,J=3.6,10.5 Hz), 3.99(5/7H,t,J=6.9 Hz), 4.84(5/7H,d,J=10.8 Hz), 4.93(2/7H,d,J=10.5 Hz), 5.06–5.18(1H,m), 5.45(1H,dd,J=5.3,10.8 Hz), 5.73(2H,brs), 6.13(5/7H,s), 6.20(2/7H,brs), 6.27(2/7H,s), 6.40(5/7H,brs), 7.18–7.40(5H,m)

Example 14
Phe-N-Me-Val-N-Me-Tyr (3-iso-C$_3$F$_7$)-NH$_2$ (1) Synthesis of 2-heptafluoroisopropyl-4-methylanisole To a solution of 2-iodo-4-methylanisole (4.57 g, 18.43 mol) in DMF (3.3 ml), copper powder (4.68 g, 73.71 mmol) and heptafluoroisopropyl iodide (5.43 ml, 37.60 mmol) were added, followed by stirring at 140° C. for 14 hours. The reaction mixture was cooled to room temperature, mixed with water and ether and filtered on Celite. The filtrate was extracted with ether; the organic layer was washed with saturated brine, dried over sodium sulfate and evaporated under reduced pressure. The thus obtained residue was subjected to silica gel column chromatography (developing solvent: n-hexane) to give the titled compound (3.64 g, 68%).

NMR (method a, CDCl$_3$): δ 2.33(3H,s), 3.81(3H,s), 6.90 (1H,d,J=8.6 Hz), 7.27(1H,dd,J=8.2,2.0 Hz), 7.36(1H,d,J= 2.0 Hz)

(2) Synthesis of 3-heptafluoroisopropyl-4-methoxybenzyl bromide

To a solution of 2-heptafluoroisopropyl-4-methylanisole (3.44 g, 11.86 mmol) in carbon tetrachloride (60 ml), N-bromosuccinimide (2.2 g, 12.22 mmol) and benzoyl peroxide (containing 25% water) (384 mg, 1.19 mmol) were added, followed by stirring for 30 min. while heating under reflux. The reaction mixture was cooled to room temperature, washed with water, dried over sodium sulfate and evaporated under reduced pressure to remove the solvent. The thus obtained residue was subjected to silica gel column chromatography (developing solvent: n-hexane) to give the titled compound (2.95 g, 67%).

NMR (method a, CDCl$_3$): δ 3.86(3H,s), 4.50(2H,s), 6.98 (1H,d,J=8.6 Hz), 7.53(1H,dd,J=8.6,2.0 Hz), 7.59(1H,d,J= 2.0 Hz)

(3) Synthesis of 3-heptafluoroisopropyl-4-methoxybenzyl iodide

To a solution of 3-heptafluoroisopropyl-4-methoxybenzyl bromide (2.95 g, 7.99 mmol) in acetone (90 ml), sodium iodide (12.0 g, 79.9 mmol) was added, followed by stirring at room temperature overnight. The reaction mixture was mixed with water and extracted with n-hexane. The organic layer was washed with an aqueous sodium thiosulfate solution and saturated brine, dried over magnesium sulfate and evaporated under reduced pressure to remove the solvent, giving the titled compound (3.12 g, 94%).

NMR (method a, CDCl$_3$): δ 3.84(3H,s), 4.46(2H,s), 6.93 (1H,d,J=8.6 Hz), 7.51(1H,dd,J=8.6,2.0 Hz), 7.58(1H,d,J= 2.0 Hz)

(4) Synthesis of N-[Bis(methylthio)methylene]-D,L-Phe (3-iso-C$_3$H$_7$-4-methoxy)-OEt Potassium tert-butoxide (1.01 g, 9.00 mmol) was dissolved in THF (17 ml) and cooled to −78° C. in a nitrogen atmosphere. To the resulting solution, a solution of ethyl ester of N-[bis(methylthio)methylene]glycine (1.55 g, 7.50 mmol) in THF (17 ml) was added dropwise, stirred for 35 min. and then a solution of 3-heptafluoroisopropyl-4-methoxybenzyl iodide (3.12 g, 7.50 mmol) in THF (25 ml) was added dropwise, followed by stirring for 1 hour. The reaction mixture was mixed with water and extracted with ethyl acetate. The organic layer was washed with saturated brine, dried over magnesium sulfate and evaporated under reduced pressure to remove the solvent. The thus obtained residue was subjected to silica gel column chromatography (developing solvent: n-hexane:ethyl acetate=20:1) to give the titled compound (2.92 g, 79%).

NMR (method a, CDCl$_3$): δ 1.21(3H,t,J=7.3 Hz), 2.39 (3H,s), 2.45(3H,s), 3.07–3.24(2H,m), 3.82(3H,s), 4.13(2H, q,J=7.3 Hz), 4.58(1H,dd,J=7.6,5.3 Hz), 6.90(1H,d,J=8.6 Hz), 7.33(1H,dd,J=8.6,2.0 Hz), 7.43(1H, dd, J=8.3,2.0 Hz)

(5) Synthesis of D,L-Phe(3-iso-C$_3$F$_7$-4-methoxy)-OEt

To a solution of N-[bis(methylthio)methylene]-D,L-Phe (3-iso-C$_3$H$_7$-4-methoxy)-OEt (2.92 g, 5.90 mmol) in dioxane (60 ml), 2N hydrochloric acid (30 ml) was added, followed by stirring for 7 hours at room temperature. The reaction mixture was mixed with a 2N aqueous sodium hydroxide solution and extracted with ethyl acetate. The organic layer was washed with saturated brine, dried over magnesium sulfate and evaporated under reduced pressure to remove the solvent. The thus obtained residue was subjected to silica gel column chromatography (developing solvent: methanol:dichloromethane=5:100) to give the titled compound (1.04 g, 59%).

NMR (method a, CDCl$_3$): δ 1.24(3H,d,J=7.3 Hz), 2.88–3.07(2H,m), 3.66–3.71(1H,m), 3.83(3H,s), 4.15(2H,q, J=7.3 Hz), 6.95(1H, d,J=8.6 Hz), 7.34(1H,dd,J=8.6,2.0 Hz), 7.39(1H,d,J=2.0 Hz)

(6) Synthesis of Z-D,L-Phe(3-iso-C$_3$F$_7$-4-methoxy)-OEt

To a mixture of a solution of D,L-Phe(3-iso-C$_3$F$_7$-4-methoxy)-OEt (1.04 g, 3.48 mmol) in dioxane (12 ml) and an aqueous solution of sodium carbonate (406 mg, 3.83 mmol) (9 ml), benzyl chloroformate (0.59 ml, 4.17 mmol) was added under cooling with ice, followed by stirring for 2 hours under cooling with ice. The reaction mixture was mixed with water and extracted with chloroform. The organic layer was washed with saturated brine, dried over sodium sulfate and evaporated under reduced pressure to remove the solvent. The thus obtained residue was subjected to silica gel column chromatography (developing solvent: n-hexane:dichloromethane=2:3) to give the titled compound (1.39 g, 95%).

NMR (method a, CDCl$_3$): δ 1.23(3H,d, J=7.3 Hz), 3.00–3.20(2H,m), 3.82(3H,s), 4.14(2H,q,J=7.3 Hz), 4.58–4.69(1H,m), 5.10(2H,s), 5.25–5.35(1H,m), 6.90(1H, d,J=8.3 Hz), 7.22–7.35(7H,m)

(7) Synthesis of Z-D,L-N-Me-Phe(3-iso-C$_3$F$_7$-4-methoxy)-OEt

To a solution of Z-D,L-Phe(3-iso-C$_3$F$_7$-4-methoxy)-OEt (1.39 g, 3.32 mmol) in DMF (20 ml), 60% sodium hydride (167 mg, 4.17 mmol) and methyl iodide (0.32 ml, 5.14 mmol) were added under cooling with ice, followed by stirring for 2 hours under cooling with ice. The reaction mixture was mixed with water and extracted with ethyl acetate. The organic layer was washed with saturated brine, dried over sodium sulfate and evaporated under reduced pressure to remove the solvent to give the titled compound (1.43 g, 100%).

NMR (method a, $CDCl_3$): δ 1.18–1.26(3H,m), 2.79(1.9H, s), 2.82(1.1H,s), 2.90–3.40(2H,m), 3.82(3H,s), 4.05–4.25 (2H,m), 4.70–5.00(1H,m), 5.07(2H,s), 6.82–6.91(1H,m), 7.20–7.37(7H,m)

(8) Synthesis of Z-D,L-N-Me-Phe(3-iso-$C_3F_7$-4-methoxy)-$NH_2$

To a solution of Z-D,L-N-Me-Phe(3-iso-$C_3F_7$-4-methoxy)-OEt (1.43 g, 3.30 mmol) in dioxane (40 ml), a 2N aqueous sodium hydroxide solution (40 ml) was added, followed by stirring for 5.5 hours at room temperature. The reaction mixture was mixed with 2N hydrochloric acid and extracted with ethyl acetate. The organic layer was dried over sodium sulfate and evaporated under reduced pressure to remove the solvent, giving crude Z-D,L-N-Me-Phe(3-iso-$C_3F_7$-4-methoxy)-OH (1.74 g).

NMR (method a, $CDCl_3$): δ 2.78(1.9H,s), 2.83(1.1H,s), 3.00–3.40(2H,m), 3.82(3H,s), 4.70–4.90(1H,m), 5.08(2H,s), 6.85–6.91(1H,m), 7.10–7.40(7H,m)

To a solution of the thus obtained crude compound (1.74 g) in DMF 13 ml, NMM (0.46 ml, 4.15 mmol) was added. The mixture was cooled to −15° C., mixed with ethyl chloroformate (0.40 ml, 4.15 mmol), stirred for 15 min. and then further 30 min. at −15° C. while blowing gaseous ammonia to the mixture. The reaction mixture was mixed with water and extracted with ethyl acetate. The organic layer was washed with saturated brine, dried over sodium sulfate and evaporated under reduced pressure to remove the solvent. The thus obtained residue was subjected to silica gel column chromatography (developing solvent: methanol:dichloromethane=3:100) to give the titled compound (1.58 g, 91%).

NMR (method a, $CDCl_3$): δ 2.84(3H,s), 2.80–3.40(2H, m), 3.82(3H,s), 4.50–5.00(1H,m), 5.07(2H,m), 5.40–6.20 (2H,m), 6.89(1H,d,J=7.9 Hz), 7.10–7.40(7H,m)

(9) Synthesis of D,L-N-Me-Tyr(3-iso-$C_3F_7$)-$NH_2$

A mixture of Z-D,L-N-Me-Phe(3-iso-$C_3F_7$-4-methoxy)-$NH_2$ (1.58 g, 3.78 mmol) and 10% palladium carbon (500 mg) in methanol (50 ml) was stirred for 13 hours in a hydrogen atmosphere. After removing the catalyst by filtration, the filtrate was evaporated under reduced pressure to give crude D,L-N-Me-Tyr(OMe-3-iso-$C_3F_7$) (780 mg, 73%).

NMR (method a, $CDCl_3$): δ 2.33(3H,s), 2.77(1H,dd,J= 14.8,9.9 Hz), 3.13–3.22(2H,m), 3.84(3H,s), 5.40–5.60(1H, m), 6.97(1H,d,J=8.3 Hz), 7.36(1H,dd,J=8.3,2.0 Hz), 7.41 (1H,d,J=2.0 Hz)

To the thus obtained crude compound (660 mg, 1.75 mmol), a boron tribromide solution (1.0M) in dichloromethane (50 ml) was added, followed by stirring for 13.5 hours at room temperature. The reaction mixture was poured into an ice-cooled saturated aqueous sodium bicarbonate solution and extracted with ethyl acetate. The organic layer was dried over magnesium sulfate to give the titled compound (600 mg, 95%).

NMR (method a, $CDCl_3$): δ 2.20(3H,s), 2.63–2.83(2H, m), 3.10(1H,t,J=6.9 Hz), 6.89(1H,d,J=8.3 Hz), 7.26(1H,dd, J=8.3,2.0 Hz), 7.37(1H,d,J=2.0 Hz)

(10) Synthesis of Z-Phe-N-Me-Val-N-Me-Tyr(3-iso-$C_3F_7$)-$NH_2$

To a solution of Z-Phe-N-Me-Val-OH (730 mg, 1.77 mmol) and D,L-N-Me-Tyr(3-iso-$C_3F_7$)-$NH_2$(640 mg, 1.77 mmol) in THF (20 ml), CMPI (543 mg, 2.12 mmol) and TEA (0.37 ml, 2.66 mmol) were added under cooling with ice and stirred under cooling with ice for 1 hour and then at room temperature overnight. The reaction mixture was mixed with water and extracted with ethyl acetate. The organic layer was dried over magnesium sulfate and evaporated to remove the solvent under reduced pressure; the thus obtained residue was subjected to silica gel column chromatography (developing solvent: methanol:dichloromethane=2:100) to give two diastereoisomers A and B of the titled compound, A (330 mg, 25%) being eluted first and then B (390 mg, 29%).

(A)

NMR (method a, $CDCl_3$): δ 0.41(0.5H,d,J=6.6 Hz), 0.47 (0.5H,d,J=6.6 Hz), 0.71(2.5H,d,J=6.6 Hz), 0.85(2.5H,d,J= 6.6 Hz), 2.10–2.30(1H,m), 2.47(3H,s), 2.60–3.20(4H,m), 2.98(3H,s), 4.60–4.70(1H,m), 5.00–5.20(2H,m), 5.74(1H,d, J=9.2 Hz), 6.88(1H,d,J=8.3 Hz), 7.12–7.40(12H,m)

(B)

NMR (method a, $CDCl_3$): δ 0.16(1.5H,d,J=6.6 Hz), 0.50 (1.5H,d,J=6.6 Hz), 0.68–0.88(3H,m), 2.15–2.35(1H,m), 2.75–3.10(4H,m), 2.90(3H,s), 2.99(3H,s), 3.40–3.60(1H,m), 4.65(1H,d,J=10.5 Hz), 4.70–5.65(3H,m), 5.00–5.10(2H,m), 6.81(1H,d, J=8.2 Hz), 7.10–7.40(12H,m)

(11) Synthesis of Phe-N-Me-Val-N-Me-Tyr(3-iso-$C_3F_7$)-$NH_2$ (A)

A mixture of Z-Phe-N-Me-Val-N-Me-Tyr(3-iso-$C3F_7$)-$NH_2$ (A) (330 mg, 0.437 mmol) and 10% palladium carbon (150 mg) in methanol (40 ml) was stirred in a hydrogen atmosphere for 13 hours. After removing the catalyst by filtration on Celite, the filtrate was evaporated under reduced pressure to remove the solvent. The thus obtained residue was subjected to silica gel column chromatography (developing solvent: methanol:aqueous ammonia:dichloromethane=2:0.1:100) to give the titled compound (204 mg, 75%).

EI-MS: 622 ($M^+$) NMR (method a, $CDCl_3$): δ 0.46(0.5H, d,J=6.9 Hz), 0.52(0.5H,d,J=6.9 Hz), 0.77(2.5H,d,J=6.6 Hz), 0.89(2.5H,d,J=6.6 Hz), 2.15–2.35(1H,m), 2.40–3.40(4H,m), 2.95(3H,s), 2.96(3H,s), 3.80–3.85(1H,m), 5.00(1H,d,J=10.9 Hz), 5.35–5.45(1H,m), 5.45–5.55(1H,m), 6.70(1H,d,J=8.2 Hz), 7.00–7.40(7H,m)

(12) Synthesis of Phe-N-Me-Val-N-Me-Tyr(3-iso-$C_3F_7$)-$NH_2$ (B)

A mixture of Z-Phe-N-Me-Val-N-Me-Tyr(3-iso-$C_3F_7$)-$NH_2$ (B) (390 mg, 0.516 mmol) and 10% palladium carbon (200 mg) in methanol (50 ml) was stirred in a hydrogen atmosphere for 13 hours. After removing the catalyst by filtration on Celite, the filtrate was evaporated under reduced pressure to remove the solvent. The thus obtained residue was subjected to silica gel column chromatography (developing solvent: methanol:aqueous ammonia:dichloromethane=4:0.1:100) to give the titled compound (174 mg, 54%).

EI-MS: 622 ($M^+$) NMR (method a, $CDCl_3$): δ 0.34(3H,d, J=6.3 Hz), 0.64(3H,d,J=6.3 Hz), 1.90–2.10(1H,m), 2.60–3.10(4H,m), 3.01(3H,s), 3.11(3H,s), 3.42–3.49(1H,m), 3.98(1H,t,J=5.9 Hz), 4.65(1H,d,J=10.9 Hz), 5.20–5.40(2H, m), 6.80(1H,d,J=8.6 Hz), 7.10–7.40(7H,m)

Test 1

Motilin Receptor Binding Test

A motilin receptor binding test was conducted in the following manner [Vantrappen et al., Regul. Peptides, 15, 143 (1986)]. The duodenum was extracted from a slaughtered rabbit, had the mucous membrane separated and homogenized in 50 mM Tris buffer to prepare a protein sample. The protein sample was incubated together with $^{125}I$ motilin 25 pM and thereafter the radioactivity bound to the protein was measured. Specific binding was defined as the difference between the radioactivity in the case of no adding and that in the case of adding a great excess amount of motilin ($10^{-7}$ M). The activity of the compound was expressed by $IC_{50}$ (in nM), as the concentration sufficient to reduce the specific binding by 50%. The result is shown in Table B-1.

Test 2
Action on the Contraction of a Specimen of Longitudinal Muscle in the Duodenum Extracted from a Rabbit The action on the motilin-induced contraction of a specimen of longitudinal muscle in the duodenum extracted from a rabbit was investigated by the following method. A duodenum specimen extracted from a slaughtered rabbit (5×15 mm) was suspended in an organ bath (10 ml) such that the longitudinal muscle would run vertically; the bath was filled with a Krebs solution kept at 28° C. A mixed gas (95% $O_2$ and 5% $CO_2$) was continuously bubbled into the Krebs solution and the contraction of the duodenum specimen was recorded isotonically (with a 1-g load) via an isotonic transducer (ME-3407, ME Commercial, Tokyo, Japan). The degree of contraction was expressed in relative values, with the contraction by acetylcholine at a dose of $10^{-4}$ M being taken as 100%. The activity of the compound was calculated as $pA_2$ value indicating its effect on the dose-dependent muscle contraction by the motilin put into the organ bath. The result is shown in Table B-1.

TABLE B-1

| Example No. | Motilin receptor binding test, $IC_{50}$ (nM) | Contraction suppressing test, $pA_2$ |
|---|---|---|
| 7 (A) | 3.5 | 7.58 |

INDUSTRIAL APPLICABILITY

The compounds of the present invention function as a motilin receptor antagonist and are useful as medicines including therapeutics of irritable bowel syndrome.

What is claimed is:

1. A compound represented by the formula (1):

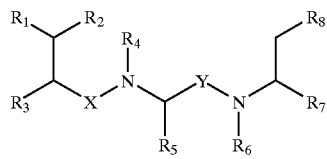

wherein $R_1$ is an optionally substituted aromatic ring;

$R_2$ is a hydrogen atom, an optionally substituted straight-chained or branched alkyl group having 1–3 carbon atoms, an amino group or a hydroxy group;

$R_3$ is a hydrogen atom, an optionally substituted straight-chained or branched alkyl group having 1–3 carbon atoms, an optionally substituted amino group or a hydroxy group;

$R_4$ is a hydrogen atom, a methyl group or an ethyl group;

$R_5$ is an optionally substituted straight-chained or branched alkyl group having 1–6 carbon atoms, a cycloalkyl group having 3–7 carbon atoms or an optionally substituted phenyl group;

$R_6$ is a hydrogen atom, a methyl group or an ethyl group;

$R_7$ is a hydrogen atom, an optionally substituted straight-chained or branched alkyl group having 1–3 carbon atoms or —CO—N($R_9$)$R_{10}$;

$R_8$ is an optionally substituted 5-membered heterocyclic ring or an optionally substituted bicyclic ring system comprising a 5-membered heterocyclic ring;

$R_{11}$ is a hydroxy group or a halogen atom;

$R_{12}$, when $R_{11}$ is a hydroxy group, represents a substituted straight-chained or branched alkyl group having 1–6 carbon atoms, a substituted straight-chained or branched alkenyl group having 2–6 carbon atoms, a substituted straight-chained or branched alkynyl group having 2–6 carbon atoms, a straight-chained or branched acyl group having 2–6 carbon atoms, a straight-chained or branched alkylsulfonyl group having 1–5 carbon atoms or an amino group mono- or di-substituted with a straight-chained or branched alkyl group having 1–5 carbon atoms, and $R_{12}$, when $R_{11}$ is a halogen atom, represents an optionally substituted straight-chained or branched alkyl group having 1–6 carbon atoms, an optionally substituted straight-chained or branched alkenyl group having 2–6 carbon atoms, an optionally substituted straight-chained or branched alkynyl group having 2–6 carbon atoms, a straight-chained or branched acyl group having 2–6 carbon atoms, a straight-chained or branched alkylsulfonyl group having 1–5 carbon atoms or an amino group mono- or di-substituted with a straight-chained or branched alkyl group having 1–5 carbon atoms;

X is a carbonyl group or a methylene group; and

Y is a carbonyl group or a methylene group; or a hydrate or pharmaceutically acceptable salt thereof.

2. The compound according to claim 1 wherein $R_1$ in the general formula (1) is a phenyl group, a para-fluorophenyl group, a para-hydroxyphenyl group; or a hydrate or pharmaceutically acceptable salt thereof.

3. The compound according to claim 1 wherein $R_2$ in formula (1) is a hydrogen atom or a methyl group; or a hydrate or pharmaceutically acceptable salt thereof.

4. The compound according to claim 1 wherein $R_3$ in formula (1) is a hydrogen atom or an amino group; or a hydrate or pharmaceutically acceptable salt thereof.

5. The compound according to claim 1 wherein $R_4$ in formula (1) is a hydrogen atom or a methyl group; or a hydrate or pharmaceutically acceptable salt thereof.

6. The compound according to claim 1 wherein $R_5$ is a methyl group, an isopropyl group, an isobutyl group, a sec-butyl group, a tert-butyl group, a 3-pentyl group, a neopentyl group, a 1,1,1,3,3,3,-hexafluoro-2-propyl group, a cyclohexyl group, a phenyl group, a benzyl group, a para-hydroxybenzyl group or a cyclohexylmethyl group; or a hydrate or pharmaceutically acceptable salt thereof.

7. The compound according to claim 1 wherein $R_6$ in the general formula (1) is a hydrogen atom or a methyl group; or a hydrate or pharmaceutically acceptable salt thereof.

8. The compound according to claims 1 wherein $R_7$ in formula (1) is a methyl group, a carbamoyl group, a methylcarbamoyl group or a dimethylcarbamoyl group; or a hydrate or pharmaceutically acceptable salt thereof.

9. The compound according to claim 2 wherein $R_8$ in formula (1) is a 3-methylindol-5-yl group, a 3,3-dimethylIndolin-5-yl group, a 3,3-dimethylindolinon-5-yl group, a 5-tert-butyl-4-carbamoylfuran-2-yl group, a 5-tertbutyl-4-sulfamoylfuran-2-yl group, a 5-tert-butyl-4-hydroxymethylfuran-2-yl group, a 2-tert-butyl-pyridin-4-yl group or a 5-tert-butyl-4-carboxyfran-2-yl group; or a hydrate or pharmaceutically acceptable salt thereof.

10. The compound according to claim 1 selected from the group consisting of Phe-N-Me-Val-[3-(3-methylindol-5-yl)]Ala-NH$_2$, and hydrates or pharmaceutically acceptable salts thereof.

11. A pharmaceutical composition containing the compound according to claim 1 as an active ingredient.

12. A motilin receptor antagonist containing the compound according to claim 1.

13. A therapeutic of hypermotilinemia containing the compound according to claim 1 as an active ingredient.

14. The compound of claim 1 wherein $R_8$ is an optionally substituted 5-membered heterocyclic ring or an optionally substituted bicyclic ring system comprising a 5-membered heterocyclic ring fused to an aromatic ring; or a hydrate or pharmaceutically acceptable salt thereof.

15. A method for suppressing gastrointestinal motility comprising administering to a patient in need thereof a compound according to claim 1.

* * * * *